(12) United States Patent
Bader et al.

(10) Patent No.: US 9,212,136 B2
(45) Date of Patent: Dec. 15, 2015

(54) METHODS FOR PRODUCING PARICALCITOL

(75) Inventors: Thomas Bader, Zürich (CH); Alfred Stutz, Zürich (CH); Hans-Ulrich Bichsel, Hörhausen (CH); Changchun Fu, Zürich (CH)

(73) Assignees: AZAD PHARMACEUTICALS INGREDIENTS AG, Schaffhausen (CH); UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 13/055,182

(22) PCT Filed: Jul. 22, 2009

(86) PCT No.: PCT/EP2009/005328
§ 371 (c)(1),
(2), (4) Date: Apr. 8, 2011

(87) PCT Pub. No.: WO2010/009879
PCT Pub. Date: Jan. 28, 2010

(65) Prior Publication Data
US 2011/0184199 A1 Jul. 28, 2011

Related U.S. Application Data

(60) Provisional application No. 61/082,605, filed on Jul. 22, 2008.

(51) Int. Cl.
C07C 401/00 (2006.01)
C07C 317/18 (2006.01)
C07C 323/12 (2006.01)

(52) U.S. Cl.
CPC .............. *C07C 401/00* (2013.01); *C07C 317/18* (2013.01); *C07C 323/12* (2013.01)

(58) Field of Classification Search
USPC .......................................... 514/167; 552/652
See application file for complete search history.

(56) References Cited

U.S. PATENT DOCUMENTS

| 4,195,027 A | 3/1980 | DeLuca et al. |
| 4,448,721 A | 5/1984 | DeLuca et al. |

FOREIGN PATENT DOCUMENTS

| EP | 0387077 A1 | 12/1990 |
| EP | 0516441 A1 | 12/1992 |
| EP | 05164102 A2 | 12/1992 |
| EP | 0582481 A1 | 2/1994 |
| WO | 9010620 | 9/1990 |
| WO | 9112240 | 8/1991 |
| WO | 2007011951 | 1/2007 |

OTHER PUBLICATIONS

"International Search Report", PCT/EP2009/005328, Dec. 2, 2010.
Graul, A. et al., "Vitamin D Analog Treatment for Hyperparathyroidism", Drugs of the Future, 1998, 23(6): 602-606.
Takahashi, Minokazu et al., "Convenient Synthesis of 1α, 25-Dihydroxyvitamin $D_3$ from Vitamin$_{D2}$", Bull. Chem. Soc. Jpn., 1994, vol. 67, No. 9, pp. 2494-2499.
Yamada, Sachiko et al., "Facile and Stereoselective Synthesis of 25-Hydroxyvitamin $D_2$", Tetrahedron Letters, 1984, vol. 25, No. 31, pp. 3347-3350.
Alonso, 3,5-Bis(trifluoromethyl)phenyl sulfones in the modified Julia olefination: application to the synthesis of resveratrol, Tetrahedron Letters, 2004, 45, 573-577.
Blakemore, et al., Ethyl(benzothiazol-2-ylsulfonyl)acetate: a new reagent for the stereoselective synthesis of α,62 -unsaturated esters from aldehydes, Org. Biomol. Chem., 2005, vol. 3, 1365-1368.
Blakemore, The modified Julia olefination: alkene synthesis via the condensation of metallated heteroarylalkylsulfones with carbonyl compounds, J. Chem. Soc., Perkin Trans. 1, 2002, 2563-2585.
Handbook of Reagents for Organic Synthesis, Oxidizing and Reducing Agents, John Wiley & Sons, LTD, 1999, p. 1.
Hanekamp, et al., 25-Hydroxydihydrotachysterol$_2$ an Innovative Synthesis of a Key Metabolite of Dihydrotachysterol$_2$, Tetrahedron, 1992, vol. 48, 9283-9294.
Hanekamp, et al., A Short and Efficient Synthesis of DE-A,B(22E,24S)-8β-(benzoyloxy)-25-hydroxyergost-22-ene. A Valuable Intermediate in the Total Synthesis of 25-Hydroxylated Vitamin $D_2$-Metabolites, Tetrahedron Letters, 1991, vol. 32, 5397-5400.
Hanekamp, Phosphorus Ylide Chemistry Investigated for Dihydrotachysterol$_2$-Metabolite Side-Chain Synthesis. The Wittig Approach, Tetrahedron, 1992, vol. 48(24), 5151-5162.
Kutner, et al., Novel Convergent Synthesis of Side-Chain-Modified Analogues of 1α,25-Dihydroxycholecalciferol and 1α,25-Dihydroxyergocalciferol, J. Org. Chem., 1988, vol. 53(15), 3450-3457.
J. March, March's Advanced Organic Chemistry, Reactions, Mechanisms, and Structure, $5^{th}$ Ed., 2001, John Wiley & Sons, Inc., pp. 1506-1569.
Mincione, et al., Improved conversion of vitamin D2 into the Windaus ketone and its regioselective hydroxylation via organoboranes at $C_{26}$, Synthetic Communications, 1989, vol. 19, 5&6, 723-735.
Morzycki, et al., Synthesis of 25-Hydroxyvitamin D2 and Its 24-Epimer, J. Org. Chem, 1984, vol. 49, 2148-2151.
Paaren, et al., Direct C(1) Hydroxylation of Vitamin $D_3$ and Related Compounds, J. Org. Chem., 1980, vol. 45, 3252-3258.
Perlman, et al., 1α,25-Dihydroxy-19-Nor-Vitamin $D_3$, a novel vitamin D-related compound with potential therapeutic activity, Tetrahedron Letters, 1990, vol. 31(13) 1823-1824.

(Continued)

*Primary Examiner* — Sabiha N Qazi
(74) *Attorney, Agent, or Firm* — Kilpatrick Townsend & Stockton LLP

(57) ABSTRACT

The present invention is directed to novel processes for the preparation of paricalcitol to novel intermediates used in these processes, and to processes for preparation of the novel intermediates.

33 Claims, 13 Drawing Sheets

(56) References Cited

OTHER PUBLICATIONS

Perlman, and DeLuca, α-Hydroxy-19-Nor-Vitamin D C-22 Aldehyde. A Valuable Intermediate in the Synthesis of Side Chain Modified 1α,25-Dihydroxy-19-Nor-Vitamin $D_3$, Tetrahedron Letters, 1992, vol. 21, 2937-2940.

Robinson and Scott: Paricalcitol. A Review of its Use in the Management of Secondary Hyperparathyroidism, Drugs, 2005, 65(4), 559-576.

Sardina, et al., Studies on the Synthesis of Side-Chain Hydroxylated Metabolites of Vitamin D2. Stereocontrolled Synthesis of 25-Hydroxyvitamin D21, J. Org. Chem., 1986, vol. 51, 1264-1269.

Wuts and Greene, Greene's Protective Groups in Organic Synthesis, $4^{th}$ Ed., 2007, John Wiley & Sons, Inc., pp. 16-299.

Zhu and Okamura, Synthesis of Vitamin D (Calciferol), Chem. Rev. 1995, vol. 95, 1877-1952.

Fig. 1: Compound IM-10

Fig. 2: Compound IM-A4

Fig. 3: Detailed example for synthesis of paricalcitol according to route A1

Fig. 5: Detailed example for synthesis of paricalcitol according to route B1

Fig. 7: General synthesis of paricalcitol using Julia olefination (Julia-Lythgoe olefination) for installation of the side chain: Route B2

Fig. 8: Detailed example for synthesis of paricalcitol according to route C1

Fig. 9: General synthesis of paricalcitol: Route C1

Fig. 10: General synthesis of paricalcitol using Julia olefination (Julia-Lythgoe olefination) for installation of the side chain: Route C2

Fig 12(a): Crystallographic Data

| | |
|---|---|
| Crystallised from | $CH_2Cl_2$ / MeOH |
| Empirical formula | $C_{35}H_{60}O_2Si$ |
| Formula weight [g mol$^{-1}$] | 540.94 |
| Crystal colour, habit | colourless, prism |
| Crystal dimensions [mm] | 0.15 × 0.20 × 0.25 |
| Temperature [K] | 160(1) |
| Crystal system | orthorhombic |
| Space group | $P2_12_12_1$ (#19) |
| Z | 4 |
| Reflections for cell determination | 97123 |
| $2\theta$ range for cell determination [°] | 4 – 50 |
| Unit cell parameters $a$ [Å] | 7.1648(1) |
| $b$ [Å] | 19.8120(1) |
| $c$ [Å] | 24.3095(2) |
| $\alpha$ [°] | 90 |
| $\beta$ [°] | 90 |
| $\gamma$ [°] | 90 |
| $V$ [Å$^3$] | 3450.71(6) |
| $F(000)$ | 1200 |
| $D_x$ [g cm$^{-3}$] | 1.041 |
| $\mu$(Mo $K\alpha$) [mm$^{-1}$] | 0.0943 |
| Scan type | $\phi$ and $\omega$ |
| $2\theta_{(max)}$ [°] | 50 |
| Transmission factors (min; max) | 0.672; 0.989 |
| Total reflections measured | 41124 |
| Symmetry independent reflections | 6062 |
| $R_{int}$ | 0.083 |
| Reflections with $I > 2\sigma(I)$ | 5303 |
| Reflections used in refinement | 6061 |

Fig 12(b): Crystallographic Data (contd.)

| | |
|---|---|
| Parameters refined | 355 |
| Final $R(F)$ [$I > 2\sigma(I)$ reflections] | 0.0589 |
| $wR(F^2)$ (all data) | 0.1590 |
| Weights: | $w = [\sigma^2(F_o^2) + (0.0855P)^2 + 1.8535P]^{-1}$ where $P = (F_o^2 + 2F_c^2)/3$ |
| Goodness of fit | 1.050 |
| Secondary extinction coefficient | 0.007(2) |
| Final $\Delta_{max}/\sigma$ | 0.001 |
| $\Delta\rho$ (max; min) [e Å$^{-3}$] | 1.33; -0.39 |
| $\sigma(d_{(C-C)})$ [Å] | 0.004 – 0.007 |

METHODS FOR PRODUCING PARICALCITOL

PRIOR RELATED APPLICATIONS

This application is a National Phase application of PCT/EP2009/005328 filed Jul. 22, 2009 which claims priority to U.S. Provisional Patent Application No. 61/082,605 filed Jul. 22, 2008, both of which are incorporated by reference herein in their entirety.

BACKGROUND OF THE INVENTION

1. Field of the Invention

The present invention is directed to novel processes for the preparation of paricalcitol to novel intermediates used in these processes, and to processes for preparation of the novel intermediates.

2. Background and Related Art

Paricalcitol (chemical name: 19-nor-1α,3β,25-trihydroxy-9,10-secoergosta-5(Z),7(Z),22(E)-triene; Synonyms: 19-nor-1,25-dihydroxyvitamin $D_2$, Paracalcin) is a synthetic, biologically active vitamin D analog of calcitriol with modifications to the side chain (D2) and the A (19-nor) ring. Paricalcitol inhibits the secretion of parathyroids hormone (PTH) through binding to the vitamin D receptor (D. M. Robinson, L. J. Scott, *Drugs*, 2005, 65 (4), 559-576) and it is indicated for the prevention and treatment of secondary hyperparathyroidism (SHPT) in patients with chronic kidney disease (CKD).

Paricalcitol is marketed under the name Zemplar®, which is available as a sterile, clear, colorless, aqueous solution for intravenous injection (each mL contains 2 microgram (2 μg) or 5 μg paricalcitol as active ingredient) or as soft gelatin capsules for oral administration containing 1 μg, 2 μg or 4 μg paricalcitol.

The molecular formula of paricalcitol is $C_{27}H_{44}O_3$ which corresponds to a molecular weight of 416.65. It is a white, crystalline powder and has the following structural formula:

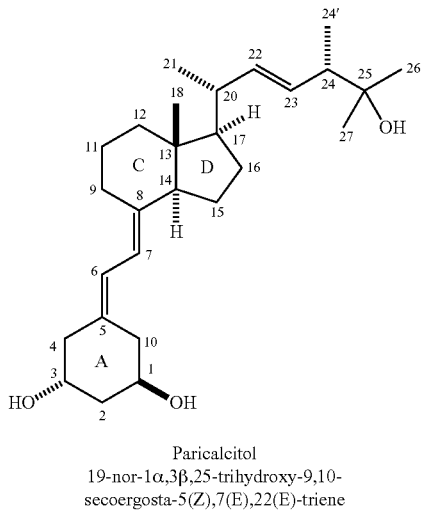

Paricalcitol
19-nor-1α,3β,25-trihydroxy-9,10-secoergosta-5(Z),7(E),22(E)-triene

Historically, nor-vitamin D compounds were described in 1990 as a new class of vitamin D analogs wherein the exocyclic methylene group C(19) in ring A has been removed and replaced by two hydrogen atoms (see e.g. WO 90/10620). So far, two different routes have been discovered for the synthesis of such 19-nor-vitamin analogs which specifically may be used for the preparation of paricalcitol.

The first synthesis of paricalcitol is disclosed in WO 90/10620 (additional patents from patent family: EP patent no. 0 387 077, U.S. Pat. No. 5,237,110, U.S. Pat. No. 5,342,975, U.S. Pat. No. 5,587,497, U.S. Pat. No. 5,710,294 and U.S. Pat. No. 5,880,113) and generally described in *Drugs of the Future*, 1998, 23, 602-606.

Example 3 of WO 90/10620 provides the preparation of 1α,25-dihydroxy-19-nor-vitamin $D_2$ (Scheme 1) by using experimental conditions analogous to the preparation of 1α,25-dihydroxy-19-nor-vitamin $D_3$. According to this description the starting material 25-hydroxyvitamin D2 is first converted to 1α,25-dihydroxy-3,5-cyclovitamin $D_2$ (a2) using the procedures published by DeLuca et al. in U.S. Pat. No. 4,195,027 and Paaren et al. published in *J. Org. Chem.*, 1980, 45, 3252. Acetylation of compound a2 followed by dihydroxylation of the exocyclic methylene group using osmium tetroxide in pyridine gives the 10,19-dihydroxy compound a4 which is converted with sodium metaperiodate (diol cleavage) to the 10-oxo-intermediate a5. Reduction of the 10-oxo group in a5 is carried out by treatment with sodium borohydride in a mixture of ethanol and water giving the corresponding 10-hydroxy derivative a6. Mesylation of the 10-hydroxy group in a6 (→a7) followed by reduction with lithium aluminium hydride in THF gives the 10-deoxy intermediate a8 wherein the 1-OAcyl group was simultaneously cleaved during the reduction step. Solvolysis (cycloreversion) of a8 by treatment with hot (55° C.) acetic acid results in the formation of two monoacetates (a9 and a10) which are separated and purified by using HPLC. Finally both monoacetates are saponified with aqueous potassium hydroxide in methanol yielding paricalcitol which is purified by HPLC.

The preparation of paricalcitol according to the method provided in WO 90/10620 has several drawbacks:

(1) the starting material 25-hydroxyvitamin D2 is one of the major metabolites of vitamin D2 and not readily available in larger amounts. Additional efforts have to be made in order to synthesize the starting material in sufficient amounts resulting in a protractive and unattractive total synthesis of paricalcitol. Examples for the preparation of 25-hydroxyvitamin D2 are described e.g. in U.S. Pat. No. 4,448,721; WO 91/12240; *Tetrahedron Letters*, 1984, 25, 3347-3350; *J. Org. Chem*, 1984, 49, 2148-2151 and *J. Org. Chem.*, 1986, 51, 1264-1269;

(2) the use of highly toxic osmium tetroxide which requires special precaution for its handling;

(3) use of HPLC for separation of isomers and purification of the final compound.

As leached in WO 2007/011951 paricalcitol is difficult to purify by HPLC and as a preparative method HPLC is generally not applicable for use on industrial scale;

(4) the yields for the preparation of paricalcitol are not described in WO 90/10620. Generally, the provided yields for the preparation of the analogue compound 1α,25-dihydroxy-19-nor-vitamin D3 are very low especially for the corresponding steps 7 to 11 (yield starting from 1α,25-dihydroxy-10-oxo-3,5-cyclo-19-nor-vitamin D3 1-acetate which is the vitamin D3 analogue to a5 in Scheme 1: step 7: 63.4%, steps 8-10: 10.7%, step 11: 51.7%; overall yield starting with step 7: 3.5%).

Scheme 1:
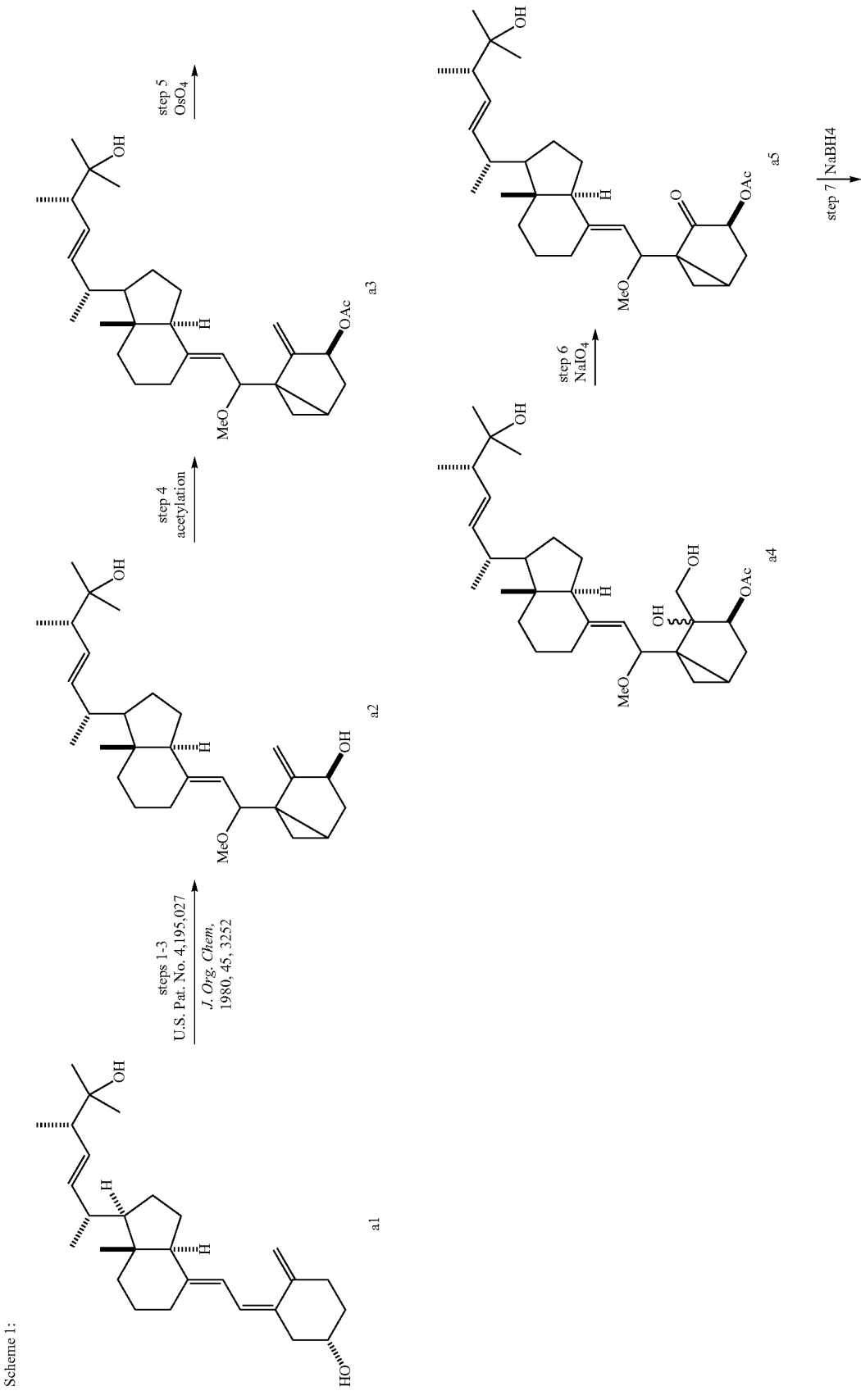

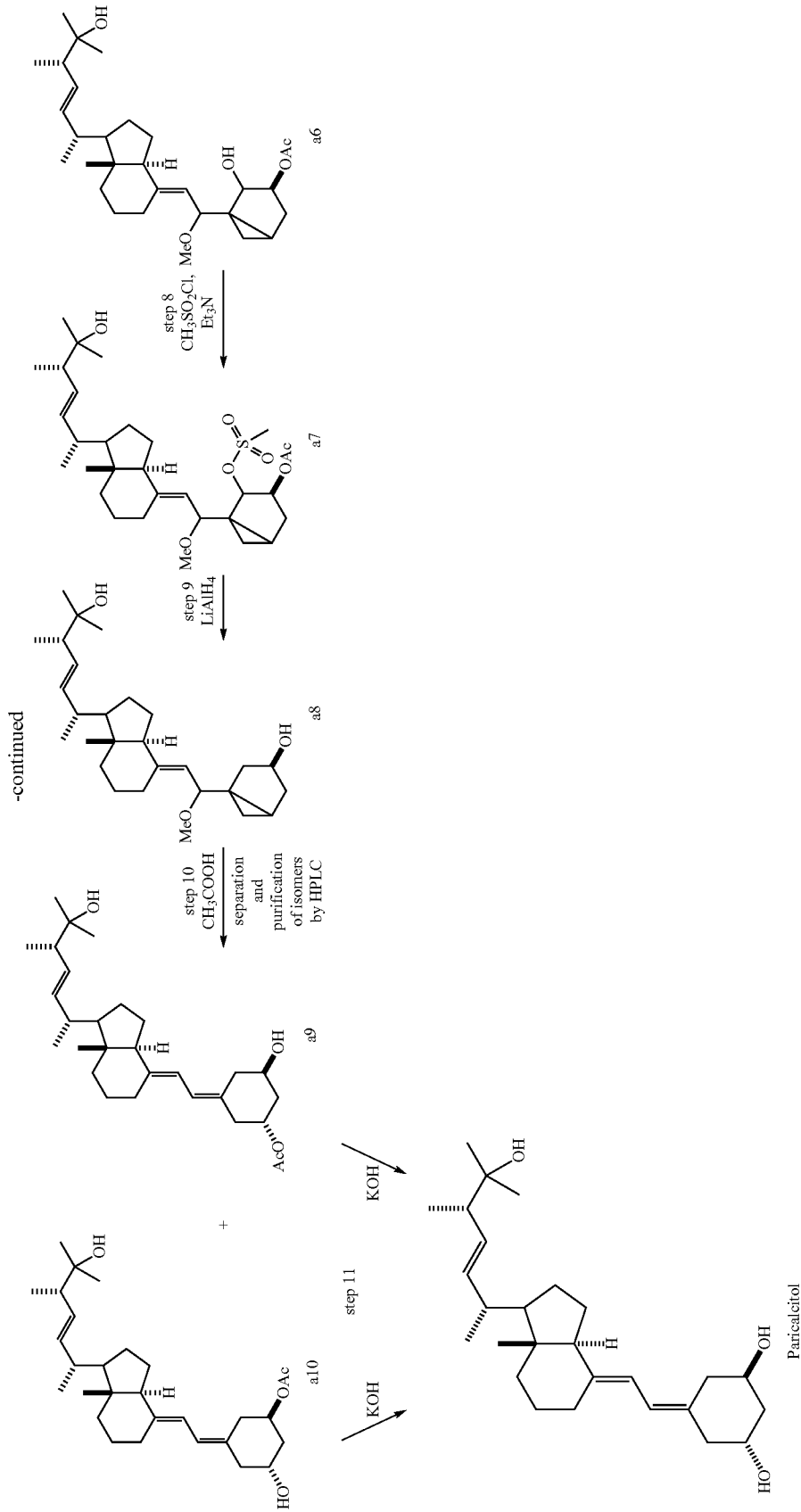

Another strategy for synthesizing 19-nor vitamin D compounds is disclosed in EP 0 516 410 (and corresponding U.S. Pat. No. 5,281,731, U.S. Pat. No. 5,391,755, U.S. Pat. No. 5,486,636, U.S. Pat. No. 5,581,006, U.S. Pat. No. 5,597,932 and U.S. Pat. No. 5,616,759). The concept is based on condensing of a ring-A unit, as represented by structure b1 (Scheme 2), with a bicyclic ketone of the Windaus-Grundmann type, structure b2, to obtain 19-nor-vitamin D compound (b3).

Scheme 2:

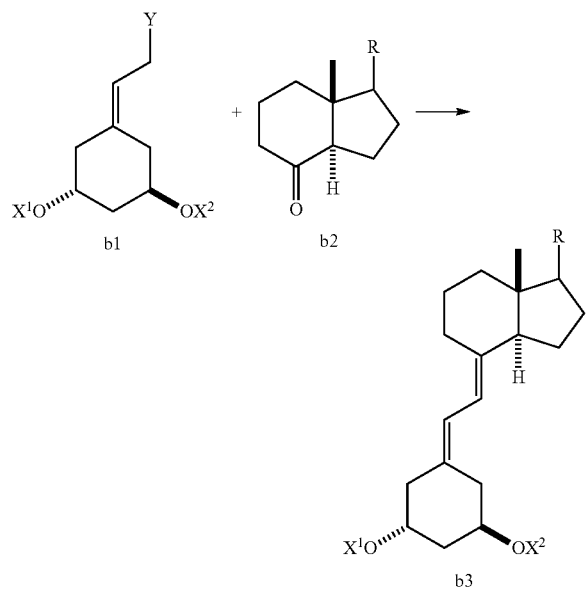

$X^1, X^2$ = hydroxy-protecting group
R = H, side chain of a vitamin D compound
Y= ——POPh$_2$, PO(OAlkyl)$_2$, SO$_2$AR, Si(Alkyl)$_3$ Specific methods for synthesizing compounds of formula b1 are shown in Schemes 3, 4 and 5. According to Scheme 3, the route starts with the commercially available (1R, 3R, 4R, 5R) (−) quinic acid (b4). Esterification of b4 with methanol followed by protection of the 1- and 3-hydroxygroup using tert-butyldimethylsilyl chloride (TBDMSCl) gives compound b5. Reduction of the ethyl ester in b5 yields b6 which is subjected to a diol cleavage giving compound b7. The 4-hydroxy group is protected as trimethylsilylether resulting in the formation of b8 which is further converted in a Peterson reaction with ethyl(trimethylsilyl) acetate before being deprotected with dilute acetic acid in tetrahydrofurane (THF). The resulting compound b9 is treated with 1,1-thiocarbonyldiimidazole to obtain b10. Subsequent reaction with tributyltin hydride in the presence of a radical initiator (AIBN) gives b11. Compound b11 is then reduced with DIBAH to the allylalcohol b12 which is then reacted with NCS and dimethyl sulfide giving the allylchloride b13. Finally the ring A synthon b14 is prepared by treatment of the allychloride b13 with lithium diphenylphosphide followed by oxidation with hydrogen peroxide.

In an alternative method for synthesizing the ring A unit (Scheme 3), the intermediate b5 can be also subjected to radical deoxygenation using analogues conditions as previously described, resulting in the formation of b16. Reduction of the ester (→b17), followed by diol cleavage (→b18) and Peterson reaction gives intermediate b11 which can be further processed to b14 as outlined in Scheme 3.

Another modification for the preparation is shown in Scheme 5. As described, b7 can be also subjected to the radical deoxygenation yielding intermediate b18 which can be further processed to b14 as depicted in Schemes 3 and 4.

Scheme 3:
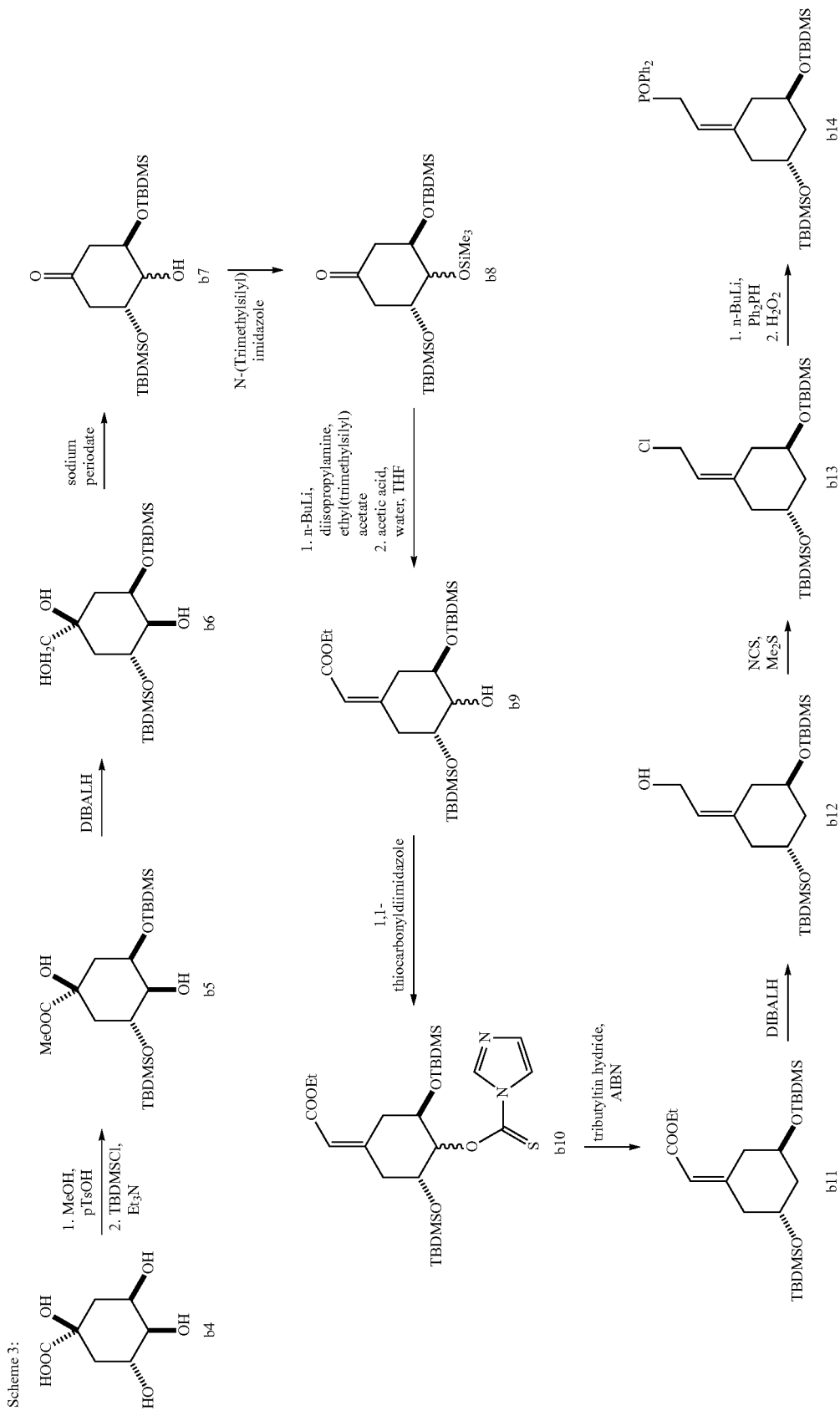

Scheme 4:

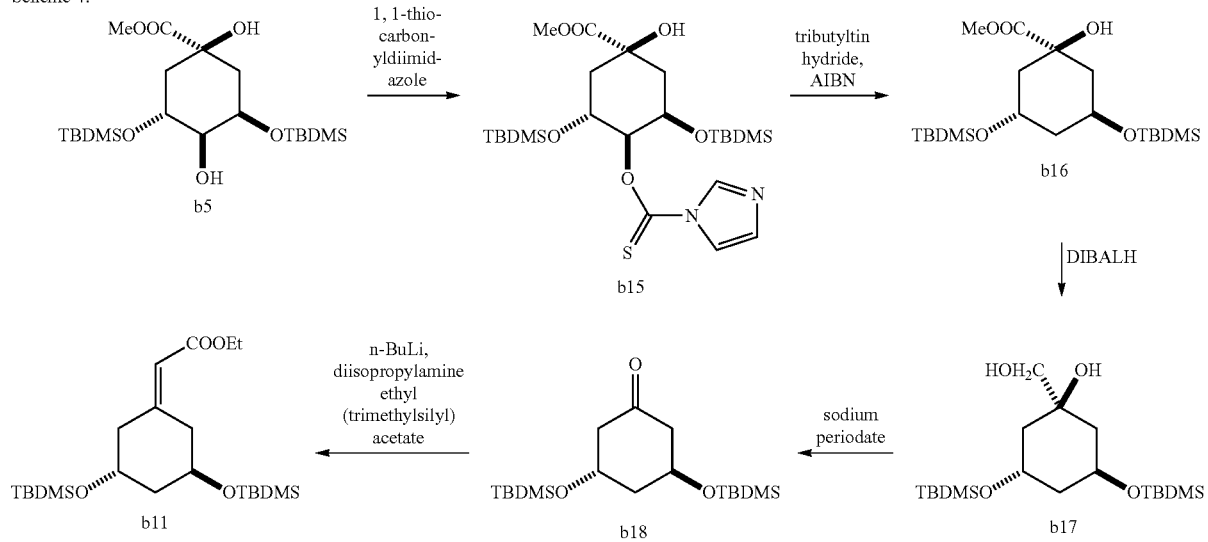

Scheme 5:

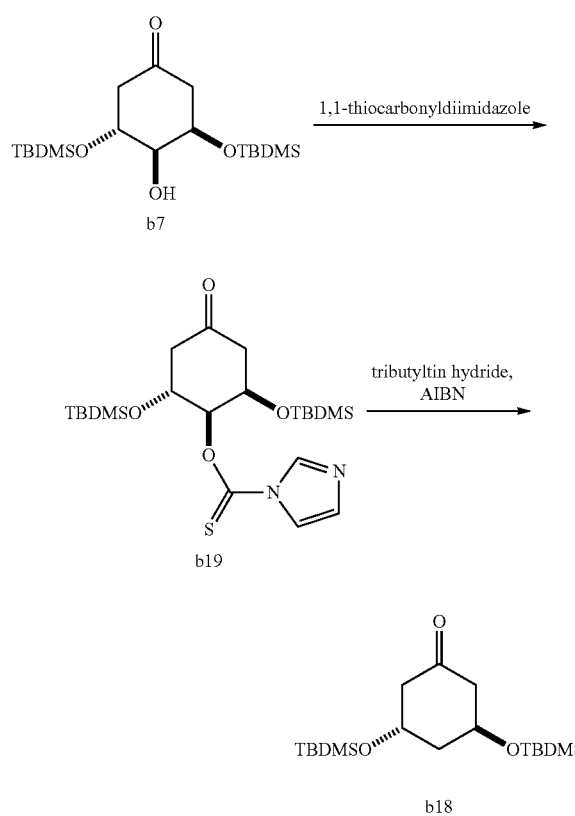

Scheme 6:

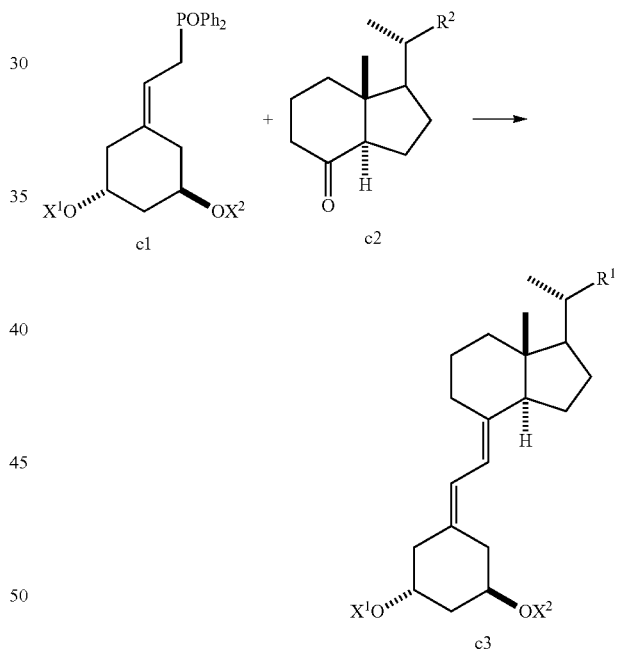

$X^1$, $X^2$ = hydroxy-protecting group (and hydrogen in c3)
$R^1$ = hydroxymethyl (—$CH_2OH$), hydroxy-protected hydroxymethyl, carboxaldehyde (—CHO), carboxy ester (—COOAlkyl)
$R^2$ = hydroxy-protected hydroxymethyl, protected carboxaldehyde such as carboxaldehyde diethyl- or ethylene acetal, carboxylalkyl In EP 0 516 411 (and its counterpart, U.S. Pat. No. 5,086, 191) is disclosed the preparation of intermediates useful for the synthesis of 19-nor vitamin D compounds (Scheme 6). The key step is the condensation of compounds c1 which can be prepared in an analogous manner as previously described for e.g. b14 (Scheme 3) with compounds c2, resulting in compounds of formula c3.

EP 0 516 411 discloses that Grignard coupling of hydroxy-protected 3-hydroxy-3-methylbutylmagnesium bromide with compound c5 (Scheme 7) can give hydroxy-protected 1α,25-dihydroxy-19-nor vitamin D3 or coupling of the corresponding 22-aldehyde c3 ($X^1=X^2$=TBDMS, $R^1$=—CHO) with 2,3-dimethylbutyl phenylsulphone can give after desulfonylation, 1α-hydroxy-19-norvitamin d2 in hydroxy-protected form.

Scheme 7:

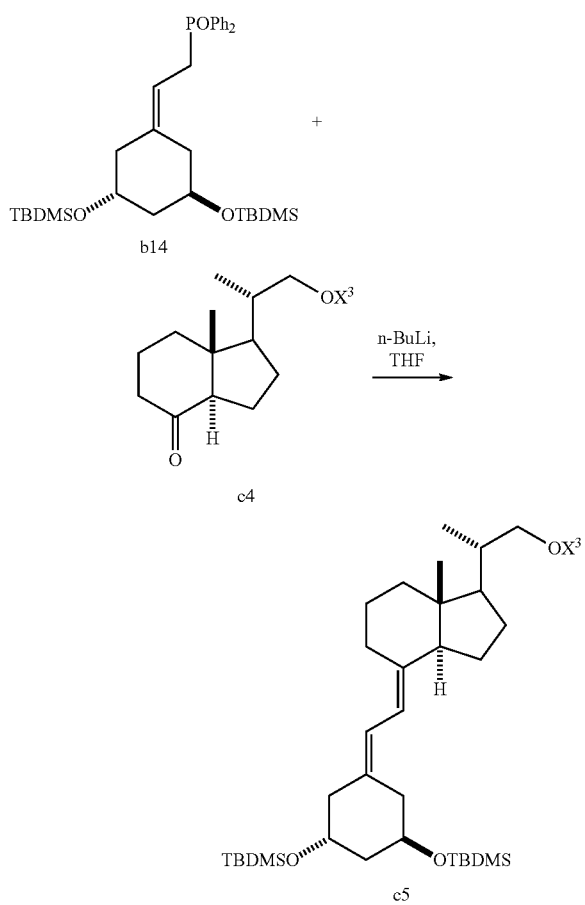

$X^3 = SO_2PhMe$

Scheme 8:

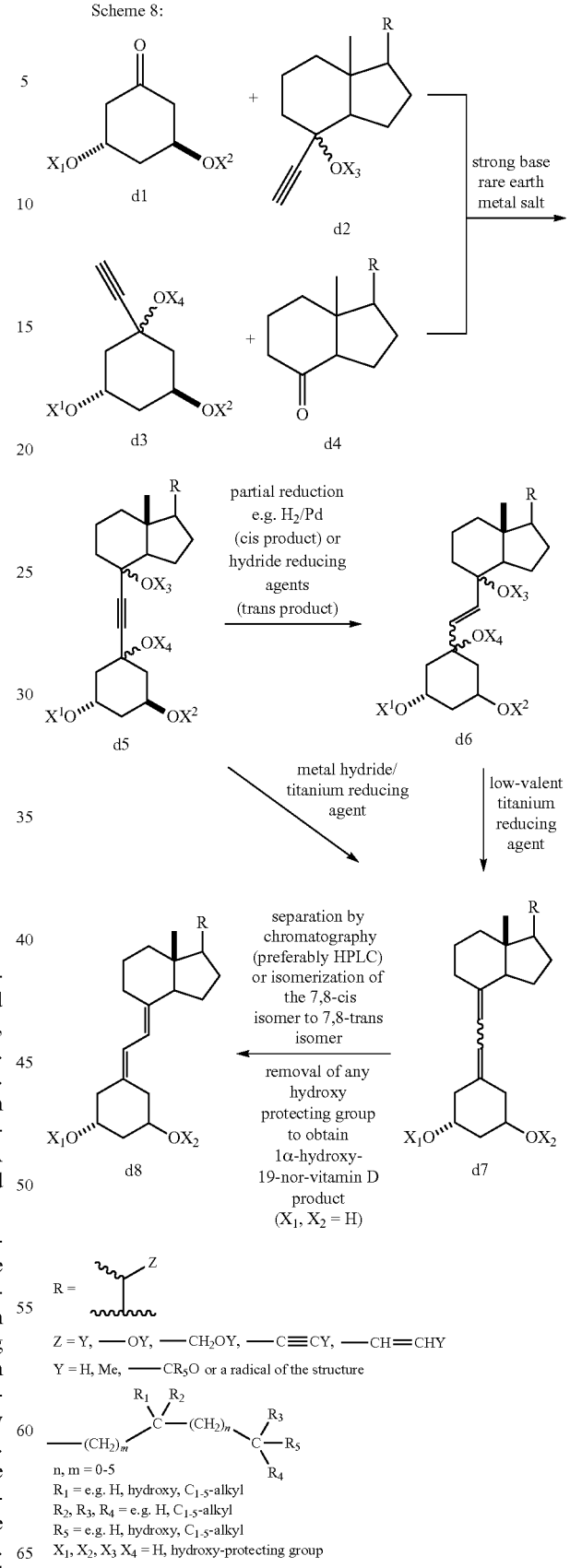

An additional method for preparation of 1α-hydroxy-19-nor-vitamin D compounds is provided in EP 0 582 481 (and corresponding U.S. Pat. No. 5,430,196, U.S. Pat. No. 5,488,183, U.S. Pat. No. 5,525,745, U.S. Pat. No. 5,599,958, U.S. Pat. No. 5,616,744 and U.S. Pat. No. 5,856,536) (Scheme 8). Similar to the strategy as described above and shown in schemes 3 to 7, the basis for preparing 1α-hydroxy-19-nor-vitamin D compounds is an independent synthesis of ring A synthon and ring C/D synthon which are finally coupled resulting in vitamin analogs.

Thus the synthesis of 1α-hydroxy-19-nor-vitamin D compounds comprises the coupling of either the ketone d1 with the acetylenic derivatives d2 or ketone d4 with acetylenic derivatives d3, yielding compounds of formula d5. Partial reduction of the triple bond giving d6 followed by reduction using low-valent titanium reducing agents results in the formation of 7,8-cis and 7,8-trans-double bond isomers (d7). Compounds of formula d7 can be also obtained directly from d5 by reaction of d5 with a metal hydride/titanium reducing agent. The isomeric mixture of compounds of formula d7 may be separated by chromatography to obtain separately the 7,8-trans-isomer. The 7,8-cis-isomer of structure d7 can be isomerized to yield the corresponding 7,8-trans-isomer. Finally any protecting groups, if present, can be then removed to obtain 1α-hydroxy-19-nor-vitamin D compounds.

The main disadvantage of the strategies as shown in Schemes 3 to 8 is the fact that ring A as well as ring C/D of the vitamin D derivative has to be separately synthesized before coupling them to compounds like 1α-hydroxy-nor-vitamin D or a protected precursor thereof. According to literature procedure, the ring fragment C/D can be prepared from vitamin D2 by ozonolysis (see e.g. J. C. Hanekamp et al., Tetrahedron, 1992, 48, 9283-9294) from which the ring A is cleaved (and disposed). This fragment has then to be separately synthesized e.g. by using other sources or starting materials like quinic acid in up to 10 steps or more. Therefore such strategies for the total synthesis of 1α-hydroxy-nor-vitamin D compounds become protractive and unattractive for large scale and according to the procedures provided in these patents, the final compounds are obtained only in amounts of <10 mg and in most cases even <1 mg.

BRIEF SUMMARY OF THE INVENTION

The present invention provides novel intermediates and processes for their preparation as well as novel processes for the synthesis of 1α-hydroxy-nor-vitamin D compounds, preferably paricalcitol, represented by the formula

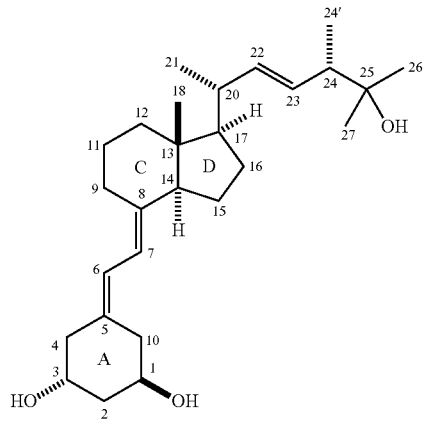

Paricalcitol
19-nor-1α,3β,25-trihydroxy-9,10-secoergosta-5(Z),7(E),22(E)-triene

The novel and convenient methods provided herein are suitable for the synthesis of paricalcitol in larger amounts of >1 g even >10 g with the possibility for further scale up. The readily available vitamin D2 can be used as starting material. Latter is transformed in appropriate steps and reactions without the cleavage of the ring A fragment from ring C/D fragment having the additional advantage of reducing the number of steps.

Thus in one aspect, the present invention provides a process for preparing 19-nor-1α,3β,25-trihydroxy-9,10-secoergosta-5(Z),7(Z),22(E)-triene (paricalcitol) of the formula

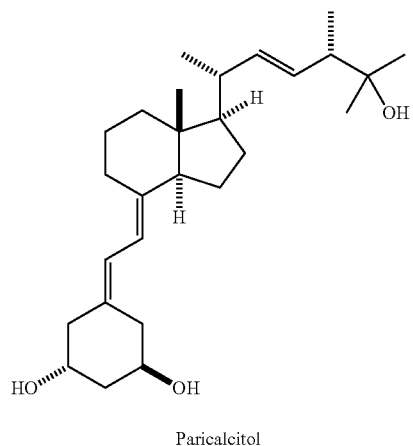 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Paricalcitol wherein vitamin D2 is used as starting material and wherein a compound of the formula

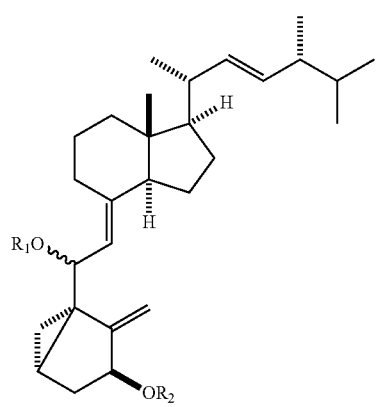

IM-A4 wherein
R₁ represents a $C_1$-$C_4$ alkyl group and
R₂ represents a hydroxyl protecting group
is used as an intermediate.

BRIEF DESCRIPTION OF THE FIGURES

A better understanding of the present invention will now be held upon reference to the following detailed description, when read in conjunction with the accompanying figures and in which:

FIG. 12(a) is a table showing the crystallographic data.

FIG. 12(b) is a continuation of the table showing the crystallographic data.

DETAILED DESCRIPTION OF THE PREFERRED EMBODIMENTS

Figure 1:
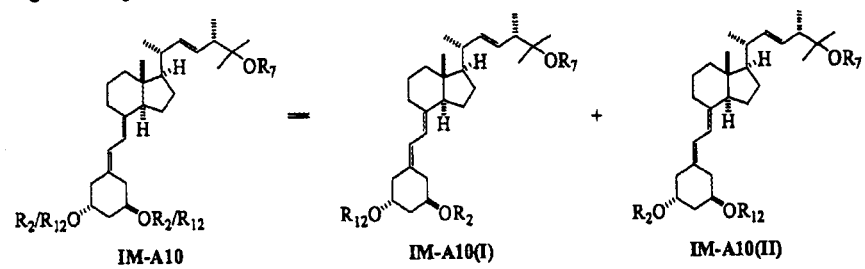
FIG. 1 shows that the compound IM-10 consists of a mixture of the 5,6-diastereomers IM-A10 (I) and IM-A10 (II).

The present invention may be understood more readily by reference to the following detailed description of the preferred embodiments of the invention, and to the examples included herein.

Definitions

For purposes of clarity, various terms and phrases used throughout this specification and the claims are defined as set forth below. If a term or phrase used in this specification, or in the claims, is not defined below, or otherwise in this specification, the term or phrase should be given its ordinary meaning.

The phrase "room temperature" as used herein means a temperature ranging from 20° C. to 25° C.

The abbreviation "Ac" as used herein means an acetyl ($CH_3CO$) group.

The abbreviation "AcCl" as used herein means acetyl chloride.

The abbreviation "AcOH" as used herein means acetic acid.

The abbreviation "AIBN" as used herein means azo-bis-isobutyronitrile.

The abbreviation "BOM" as used herein means benzyloxymethyl.

The abbreviation "BT" as used herein means benzothiazol-2-yl.

The abbreviation "BTFP" as used herein means 3,5-bis(trifluoromethyl)phenyl.

The abbreviation "BzCl" as used herein means a benzoyl ($C_6H_5CO$) group.

The abbreviation "BzCl" as used herein means a benzoyl chloride.

The abbreviation "DABCO" as used herein means 1,4-diazabicyclo[2,2,2]octane.

The abbreviation "DCC" as used herein means N,N'-dicyclohexyl-carbodiimide.

The abbreviation "DIBALH" as used herein means diisobutylaluminium hydride.

The abbreviation "DMAP" as used herein means 4-dimethylamino pyridine.

The abbreviation "DME" as used herein means dimethoxyethane.

The abbreviation "DMSO" as used herein means dimethyl sulfoxide.

The abbreviation "EtOAc" or "AcOEt" as used herein means ethyl acetate.

The abbreviation "Eq." as used herein means equivalent.

The abbreviation "Et" as used herein means an ethyl group.

The abbreviation "EtOH" as used herein means ethanol.

The abbreviation "h" as used herein means hour.

The abbreviation "HPLC" as used herein means high performance liquid chromatography.

The abbreviation "IM" as used herein means intermediate.

The abbreviation "IT" as used herein means internal temperature. The internal temperature is the temperature in the respective reaction mixture.

The abbreviation "i-Pr" as used herein means an iso-propyl group.

The abbreviation "i-PrOAc" as used herein means iso-propyl acetate.

The abbreviation "JR" as used herein means Julia reagent. Julia reagents are known chemicals for synthesis and are known to the skilled person (e.g. Brückner, "Reaktionsmechanismen", Spektrum akademischer Verlag, $2^{nd}$ edition, 2002, 480-482 and P. R. Blakemore, J. Chem. Soc., Perkin Trans. 1, 2002, 2563-2585).

The abbreviation "KHMDS" as used herein means potassium hexamethyldisilazane.

The abbreviation "MeCN" as used herein means acetonitrile.

The abbreviation "MeLi" as used herein means methyllithium.

The abbreviation "Ms" as used herein means an mesyl ($CH_3SO_2$) group.

The abbreviation "MTBE" as used herein means methyl tea-butyl ether.

The abbreviation "NCS" as used herein means N-chlorosuccinimide.

The abbreviation "n-BuLi" as used herein means n-butyllithium.

The abbreviation "PG" as used herein means protection group.

The abbreviation "PT" as used herein means 1-phenyl-1H-tetrazol-5-yl.

The abbreviation "Py" as used herein means pyridine.

The abbreviation "TBAF" as used herein means tetra-n-butylammonium fluoride.

The abbreviation "TBS" or "TBDMS" as used herein means a tert.-butyldimethylsilyl group.

The abbreviation "TBSCl" or "TBDMSCl" as used herein means tert.-Butyldimethylsilyl chloride.

The abbreviation "TEMPO" as used herein means 2,2,6,6-tetramethylpiperidin-1-oxyl.

The abbreviation "TBT" as used herein means 1-tert.butyl-1H-tetrazol-5-yl.

The abbreviation "THF" as used herein means tetrahydrofurane.

The abbreviation "TLC" as used herein means thin layer chromatography.

The abbreviation "WR" as used herein means Wittig reagent. Wittig reagents are known chemicals for synthesis and well-known to the skilled person.

The phrase "one-pot process" as used herein means that chemical steps are combined without isolation of intermediates.

The abbreviation "v" as used herein means volume, and the abbreviation "v/v" as used herein means the ratio of volumes.

The abbreviation "m" as used herein means mass, and the abbreviation "v/m" as used herein means the ratio of volume to mass.

In the definitions of the radicals given in the formulae below, collective terms were used which are generally representative of the following substituents:

halogen: fluorine (F), chlorine (Cl), bromine (Br) and iodine (I);

$C_{1-4}$ alkyl: saturated, straight-chain or branched hydrocarbon radicals having 1-4 carbon atoms, e.g. methyl, ethyl, propyl, 1-methylethyl, butyl, 1-methylpropyl, 2-methylpropyl and 1,1-dimethylethyl; particular preference is given to methyl;

$C_1$-$C_4$ carboxylic acid: formic acid, acetic acid, propionic acid and butyric acid, $C_1$-$C_4$ alkanoic acids are $C_1$-$C_4$ carboxylic acids, aryl: phenyl, naphthyl and phenanthryl, particular preference is given to phenyl.

Depending on the substitution pattern, the compounds according to the invention can, if appropriate, be present as mixtures of different possible isomeric forms, in particular of stereoisomers, such as enantiomers, diastereomers, E- and Z-isomers.

The drawing as exemplary shown for IM-A10 in FIG. 1 means a mixture of 5,6 diastereomers IM-A10(I) and IM-A10 (II).

Figure 2:
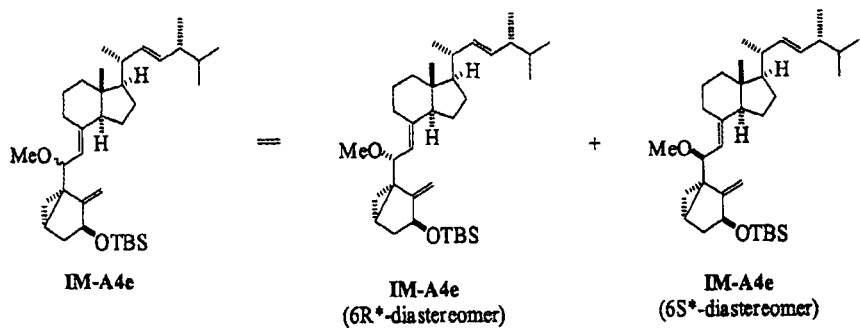
FIG. 2 shows that the compound IM-A4e consists of a mixture of 6R* and 6S* diastereomers.

The drawing as exemplary shown for IM-A4e in FIG. 2 means a mixture of 6R*- and 6S*-diastereomers. In all drawings for the 6R*/S*-diastereomers, the numbering of the compounds still remains IM-A4e while the structure indicates the presence of a single 6-diastereomer or a mixture thereof.

General Description and Utility

The problem underlying the present invention was to provide processes as well as intermediates for preparing 1α-hydroxy-nor-vitamin-D compounds, in particular for preparing paricalcitol, on a large scale, which allow the use of cheap starting materials being available in larger amounts, which can be carried out without the use of expensive or highly toxic reagents and which avoid extensive purification of the final products. A further problem underlying the present invention was to provide processes for the preparation of the intermediates used in these processes in pure form.

This problem is solved by a process for the preparation of 19-nor-1α-3β,25-trihydroxy-9,10-secoergosta-5(Z),7(Z)-22 (E)-triene(paricalcitol) of the formula

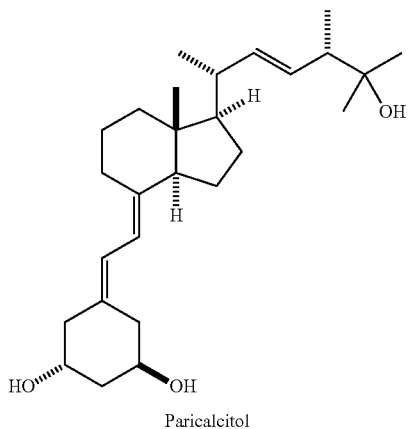

Paricalcitol wherein vitamin-D2 is used as starting material and wherein a compound of the formula

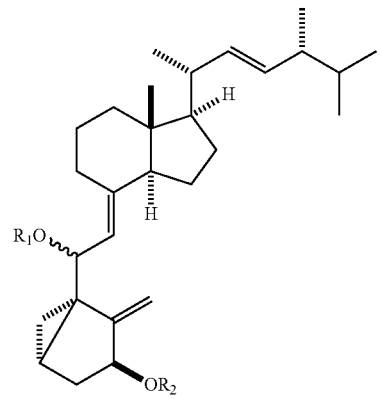

IM-A4 wherein $R_1$ represents a $C_1$-$C_4$ alkyl group and $R_2$ represents a hydroxy protecting group is used as an intermediate.

In the compounds of the formula IM-A4, $R_2$ preferably represents a tert-butyldimethylsilyl group (TBS group). Further preferred meanings of the radicals $R_1$ and $R_2$ in the compounds of the formula IM-A4 are given below. Particular preference is given to processes, wherein the compound of the formula IM-A4 is the compound of the formula IM-A4e.

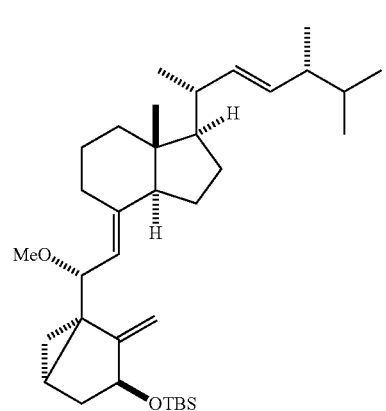

IM-A4e

The process according to the invention enjoys a number of advantages. Thus, it makes possible the transformation of vitamin D2 without cleavage of the A-fragment from C/D core followed by its reconnection according to the strategies as described above. The transformations include a side chain modification, the removal of the exocyclic methylene group and the introduction of a 1α-hydroxyl group. More specifically the side chain modifications include a formal introduction of a hydroxyl group into position 25 resulting in the formation of paricalcitol (Scheme 9).

Scheme 9:

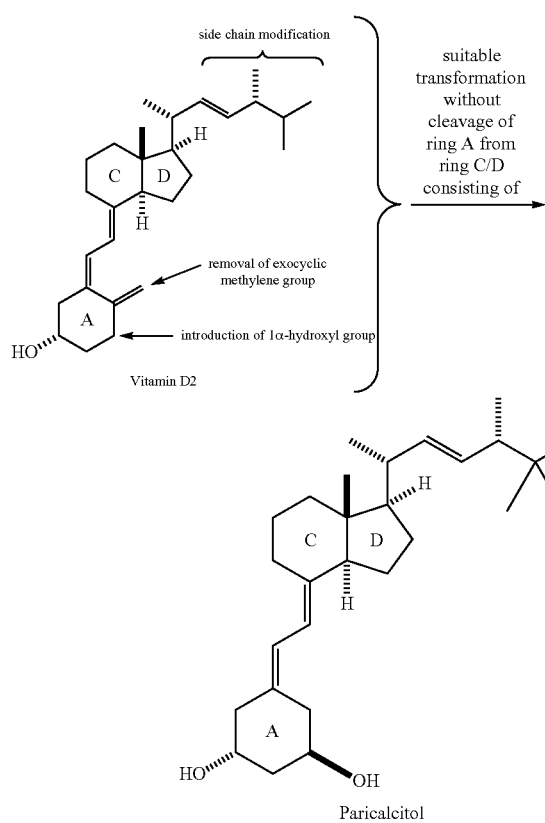

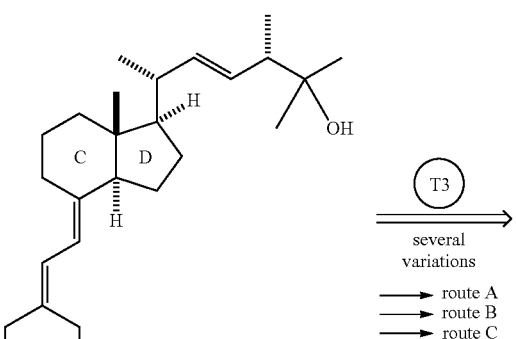

The new processes for preparation of 1α-hydroxy-nor-vitamin D compounds, preferably paricalcitol, according to routes A1, B1, B2, C1 and C2 are characterized in that the core structure of vitamin D2 consisting of the rings A, C and D remains during the transformation while the cleavage of the side chain and the exocyclic methylene group are carried out simultaneously (Scheme 10, transformation step T2). Thus, the processes according to routes A1, B1, B2, C1 and C2 make possible the preparation of 1α-hydroxy-nor-vitamin D compounds, preferably of paracalcitol in less transformation steps.

Scheme 10

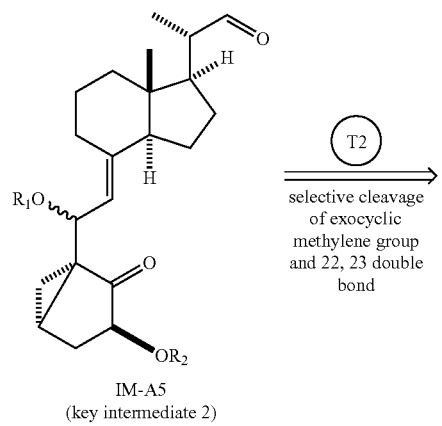

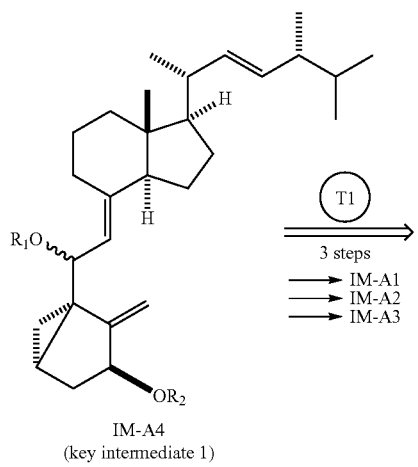

Figure 4:
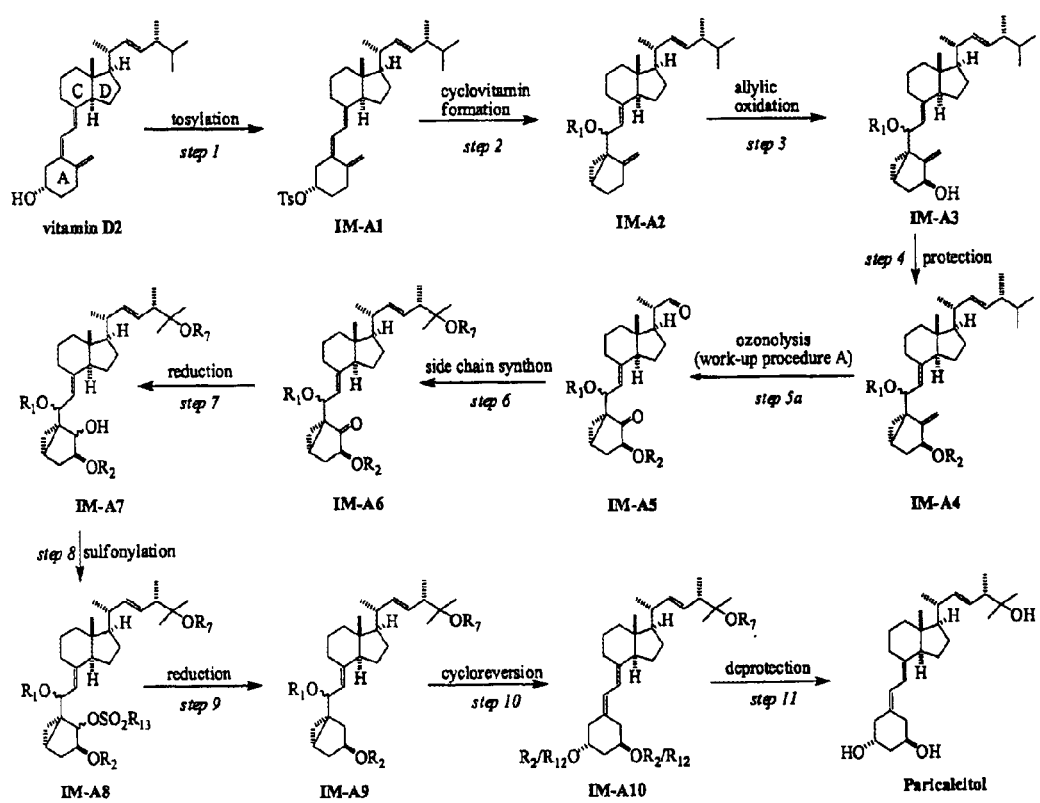
FIG. 4 is a flow chart showing the general synthesis of paracalcitol according to route A1.
Figure 6:
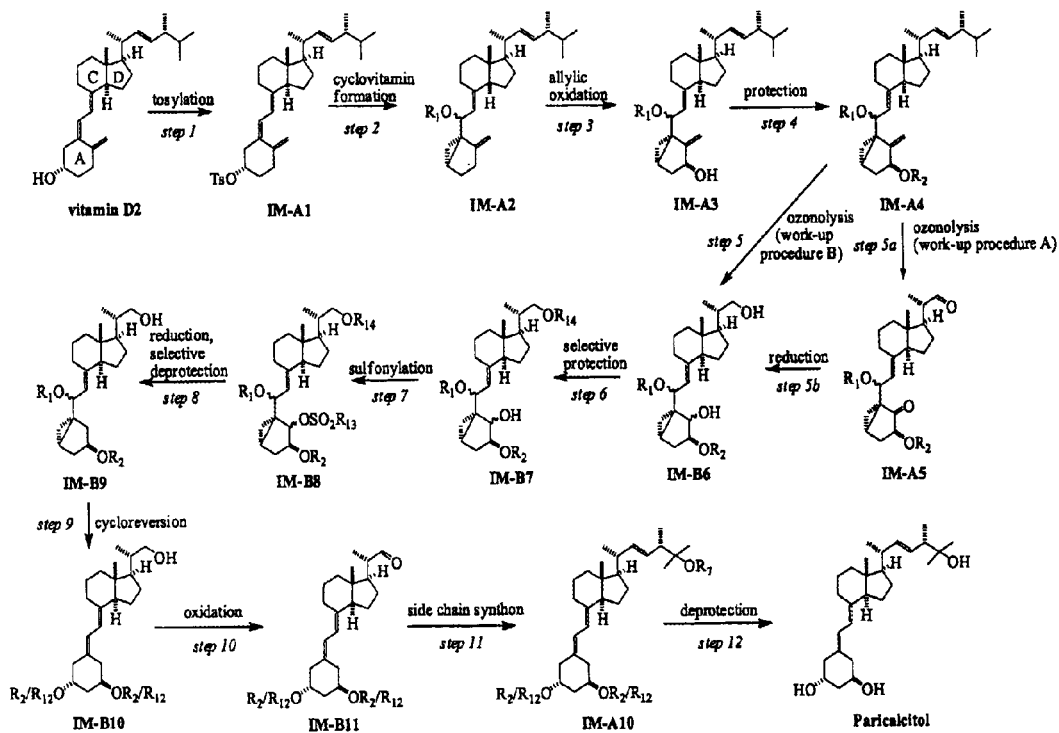
FIG. 6 is a flow chart showing the general synthesis of paricalcitol according to route B1.
Figure 7:
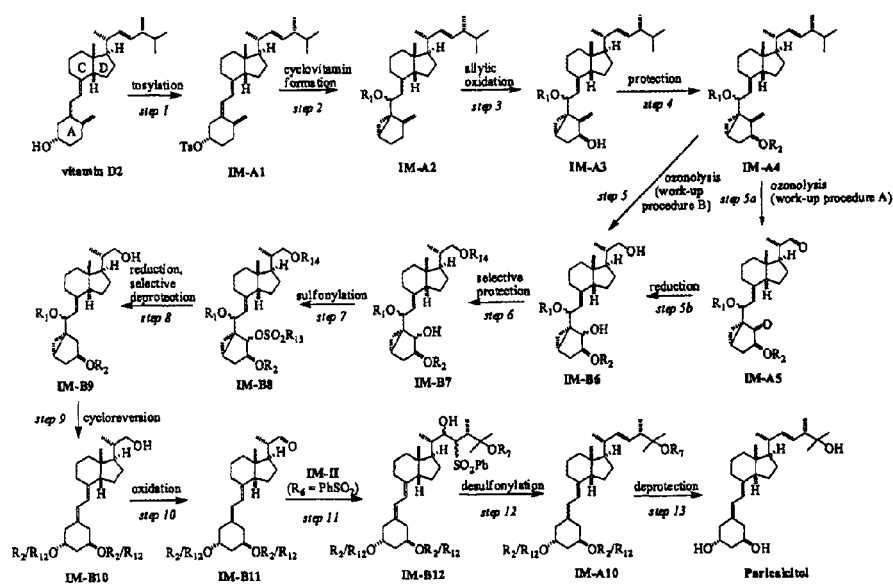
FIG. 7 is a flow chart showing the general synthesis of paricalcitol using Julia olefination for installation of the side chain according to route B2.
Figure 9:
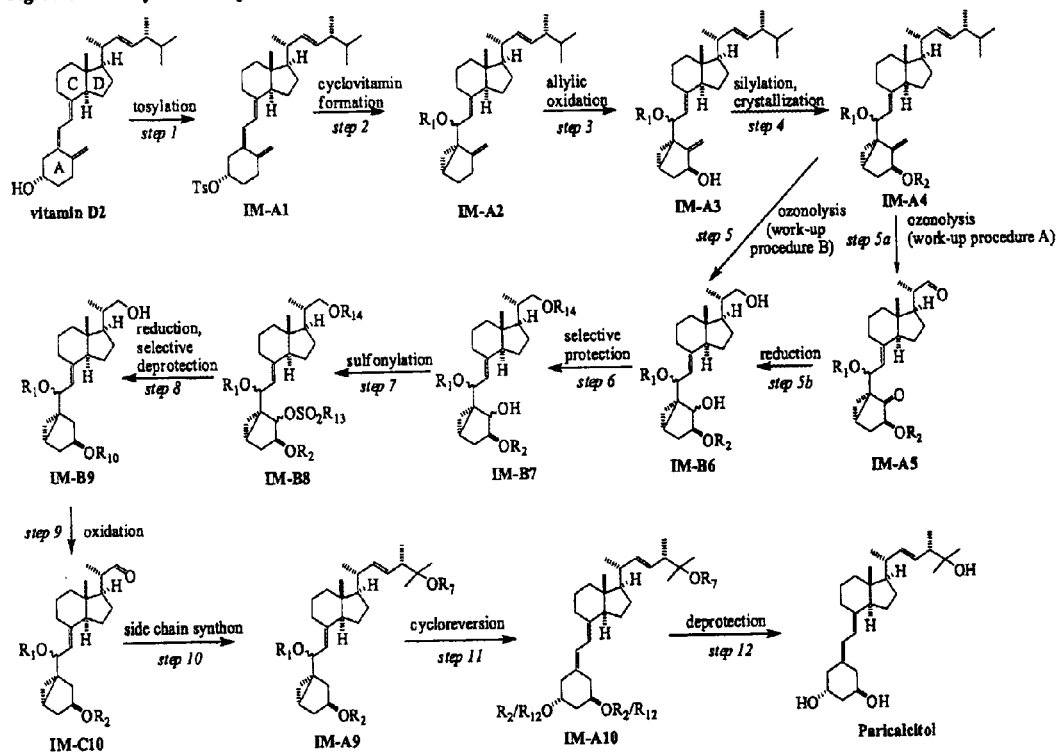
FIG. 9 is a flow chart showing the general synthesis of paricalcitol according to route C1.
Figure 10:
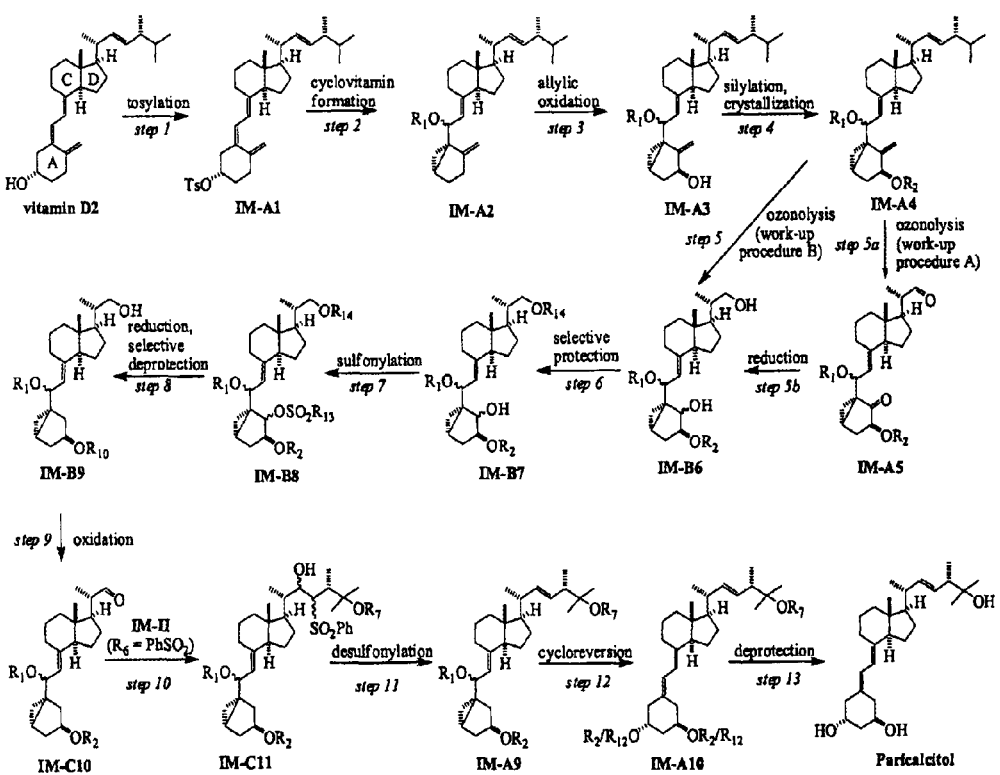
FIG. 10 is a flow chart showing the general synthesis of paricalcitol using Julia olefination for installation of the side chain according to route C2.
Figure 11:
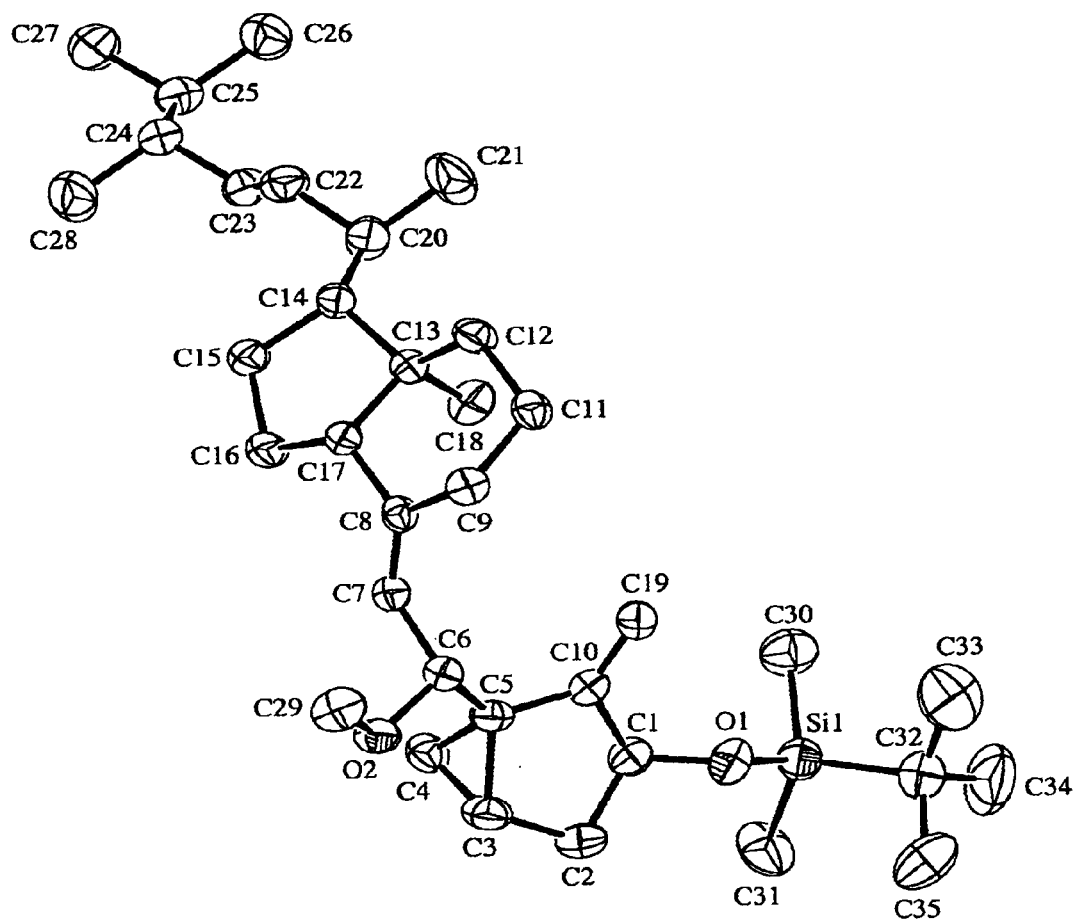
FIG. 11 is the crystal structure of the intermediate IM-A4e.

Particular embodiments of this process solving the problem underlying the present invention are the process according to route A1 as depicted in FIG. 4, the process according to route B1 as depicted in FIG. 6, the process according to route B2 as depicted in FIG. 7, the process according to route C1 as depicted in FIG. 9 and the process according to route C2 as depicted in FIG. 10 as well as the intermediates disclosed in these figures, which can be directly used for the synthesis of 1α-hydroxy-nor-vitamin-D compounds, in particular for the preparation of paricalcitol.

Methods for the Synthesis of Paricalcitol Starting from Vitamin D2

Surprisingly, vitamin D2 as readily available starting material can be used for the preparation of 1α-19-nor-vitamin D compounds preserving the core ring structure (A, C and D) during the transformation steps.

As shown in Scheme 9, the preparation of paricalcitol starting from vitamin D2 consists generally of three main transformations steps:

1. introduction of the 1α-hydroxyl group;
2. removal of the exocyclic methylene group (formal replacement of the methylene group by two hydrogen atoms);
3. side chain modification which is a formal substitution of the hydrogen in position C25 by a hydroxyl group.

Since a direct and selective chemical hydroxylation of the position C25 in vitamin D2 is difficult, the side chain modification has to be carried out by cleavage of the double bond in position 22/23 followed by reformation using a suitable side chain precursor bearing the desired substituents. General methods for the side chain construction are e.g. described by Gui-Dong Zhu and William H. Okamura, *Chem. Rev.* 1995, 95, 1727-1952.

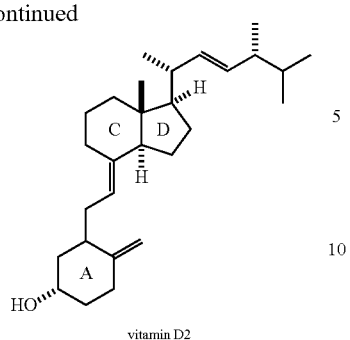

vitamin D2

Thus according to Scheme 10 the transformation sequence for preparation of paricalcitol consists of:

T1: Transformation of vitamin D2 to the key intermediate 1 (IM-A4) which involves the formation of a cyclovitamin derivative (IM-A1), an alpha hydroxylation at C1 next to the exocyclic methylene group (IM-A2) and protection of the 1α-hydroxyl group (IM-A3). Such transformations are well known and described e.g. by DeLuca (U.S. Pat. No. 4,195,027) or by Gui-Dong Zhu and William H. Okamura, *Chem. Rev.* 1995, 95, 1727-1952. $R_1$ may be a $C_1$ to $C_4$ alkyl group and $R_2$ a suitable hydroxyl protection group.

T2: Simultaneous and selective cleavage of the exocyclic methylene group (C(19)) and the side chain (22,23-double bond) in one step results in the formation of the key intermediate 2 (IM-A5) wherein the core structure consisting of rings A, and C/D remains. Well known is the selective ozonolytic cleavage of the vitamin side chain (22,23-double bond) after triene protection (for triene protection, see e.g. Gui-Dong Zhu and William H. Okamura, *Chem. Rev.* 1995, 95, 1727-1952). Ozonolysis of vitamin D2 without any double bond protection gives simultaneously cleavage of the side chain (22,23-double bond) and cleavage of the ring A fragment (7,8-double bond) from the ring C/D fragment (see e.g. E. Mincione et al., *Synthetic Communications,* 1989, 19, 723-735, F. J. Sardina et al, *J. Org. Chem,* 1986, 51, 1264-1269, K. L. Pearlman, H. F. DeLuca, *Tetrahedron Letters,* 1992, 33, 2937-2940). Thus obtained C/D ring fragment is a well known starting material for the synthesis of different vitamin D analogs including the synthesis of 1α-19-nor-vitamin compounds (see schemes 2 and 6-8).

Since the triene protection methods include in most cases the direct protection of the exocyclic methylene group another protection strategy is necessary which allows the simultaneous cleavage of the side chain and the exocyclic methylene group without affecting the 7,8-double bond. A useful protection method is Mazur's cyclovitamin approach, in which the exocyclic methylene group is still present.

Less is known and investigated for a simultaneous cleavage of the cyclovitamin D2 side chain and the exocyclic methylene group in compounds like the key intermediate 1 without simultaneous cleavage of the 7,8-double bond. There is only one example is described in the literature (M. Takahashi, Y Sakakibara, *Bull. Chem. Soc. Jpn.,* 1994, 67, 2492-2499) in which (1S,6R)-1-acetoxy-6-methoxy-3,5-cyclovitamin D2 (e1a, Scheme 11) was treated with ozone, followed by addition of dimethyl sulfide to give the aldehyde e2a and the aldehyde e3a in 24% and 42% yield, respectively. In order to suppress the formation of the undesired dicarbonyl compound (e3a) the 6-methoxy group was replaced by 6-BDT (6-(1,3-benzodithiol-2-yloxy)) group.

Scheme 11:

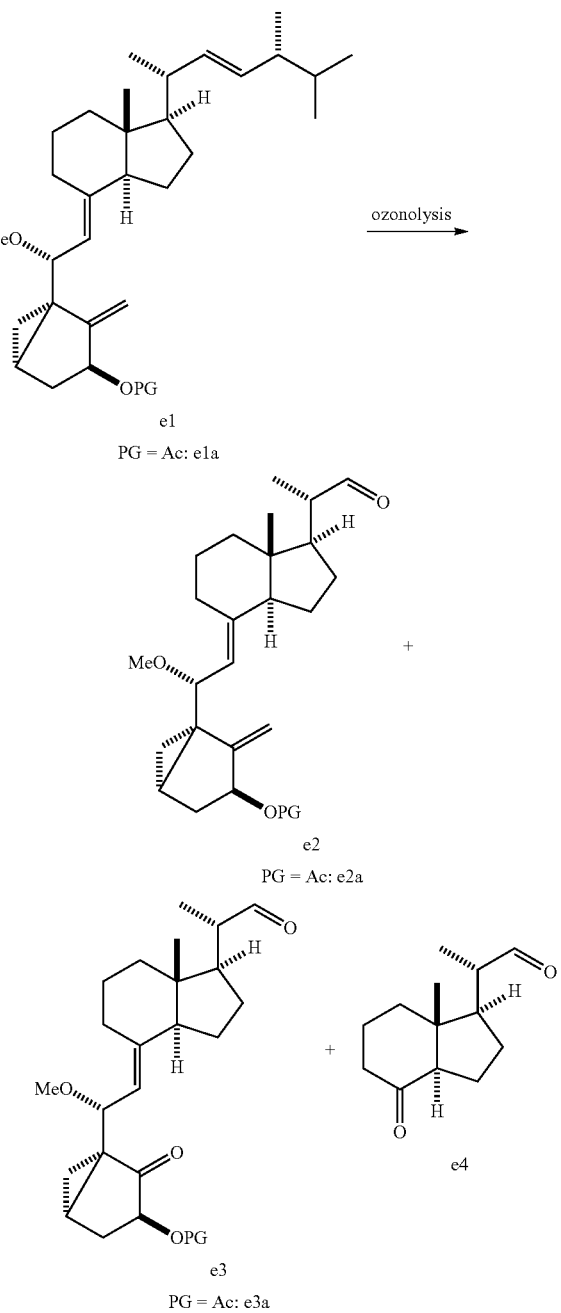

By repeating of the ozonolysis of compound e1a it has been found that beside e2a and e3a an additional undesired dicarbonyl compound (e4) was formed resulted by a cleavage of ring A from fragment C/D. This indicates generally the difficulty for a differentiation of the double bond cleavage in position 7,8 from the double bond cleavages in positions 10,19 and 22,23 during the ozonolysis.

It is surprising that prior to this invention the "undesired" dicarbonyl compound e3a was not appreciated as a suitable intermediate for the preparation of 1α-19-nor-vitamin D compounds.

Surprisingly, it has been now found that by variation of the 1-hydroxy-protection group (PG) in e1, the simultaneous and selective cleavage of the cyclovitamin D2 side chain and the exocyclic methylene group yielding compounds like e3 can be significantly improved while the formation of e4 can be almost avoided. For the selective oxidative cleavage of the double bonds in position 10,19 and 22,23, 1α-hydroxyl protection groups selected from silyl protecting groups are preferred.

Thus for the simultaneous cleavage of the side chain and the exocyclic methylene group in key intermediate 1 resulting in the formation of key intermediate 2 (Scheme 10), $R_1$ may be selected from lower alkyl groups, preferably from linear $C_1$ to $C_4$ alkyl groups and is most preferably a methyl group. Suitable protecting groups $R_2$ may be selected from typical silyl-protection groups as described e.g. by P. G. M. Wuts and T. W. Greene in *Greene's Protective Groups In Organic Synthesis*, fourth edition 2007, published by John Wiley & Sons, Inc., Hoboken, N.J. (ISBN-13: 978-0-471-69754-1, ISBN-10: 0-471-69754-0) and is preferably selected from —Si($R_3$)($R_4$)($R_5$), wherein $R_3$, $R_4$ and $R_5$ are independently $C_1$-$C_4$ alkyl groups or phenyl groups and is most preferably a TBS (tert.-butyldimethylsilyl) or TES (triethylsilyl) group.

T3: Starting with the key intermediate 2 (IM-A5) paricalcitol can be prepared by formation of the corresponding side chain via the C(22)-aldehyde function in a Wittig reaction or Julia olefination using suitable side chain synthons followed by deoxygenation of the C(10)-keto group (replacement of the oxygen by two hydrogen atoms) and cycloreversion (cyclovitamin-vitamin rearrangement) (see also FIG. 3-10).

While each of the transformation is generally known, the use of key intermediate 2 (IM-A5) prepared from readily available vitamin D2 and combining the approaches for the preparation of paricalcitol is novel. It is an advantage that via the aldehyde function different modified side chains may be introduced, resulting in the formation of 1α-hydroxy-nor-vitamin D derivatives after deoxygenation of the C(10)-keto group to the corresponding methylene group and cycloreversion. Further, the order of side chain formation, deoxygenation and cycloreversions is variable (compare also routes A1, B1, B2, C1 and C2, FIG. 3-10) and several additionally possibilities exist by variation of protecting groups and the order of the reaction steps starting from key intermediate 2 (IM-A5). During the variations, the compatibility of the functional groups with the conversions have to be taken into account. For instance, it has been found that in cases wherein the deoxygenation of the C(10)-keto group in compounds like key intermediate 2 is carried out first, the C(22)-aldehyde function should be transformed to a functional group which is compatible with the deoxygenation approaches. Such transformations may be either the conversion of the C(22)-aldehyde group simultaneously with the C(10)-keto group to the corresponding hydroxyl groups followed by selective protection of the primary C(22)-hydroxyl group or the protection of the aldehyde group first, before the deoxygenation of the C(10)-keto group is carried out. Suitable protection groups for hydroxyl groups or aldehyde groups are described e.g. by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0).

Preferred side chain formation uses synthons like compounds IM-II (Scheme 12) and result in the formation of protected or non-protected paricalcitol side chain (25-hydroxyvitamin D2 side chain, $R_7$=H or $R_8$). The side chain construction may include such approaches as described by Gui-Dong Zhu and William H. Okamura, *Chem. Rev.* 1995, 95, 1727-1952 or any other approaches which preferably form the $\Delta^{22,23}$-E double bond. Typical methods are e.g. the Wittig reaction or Julia olefination.

Scheme 12:

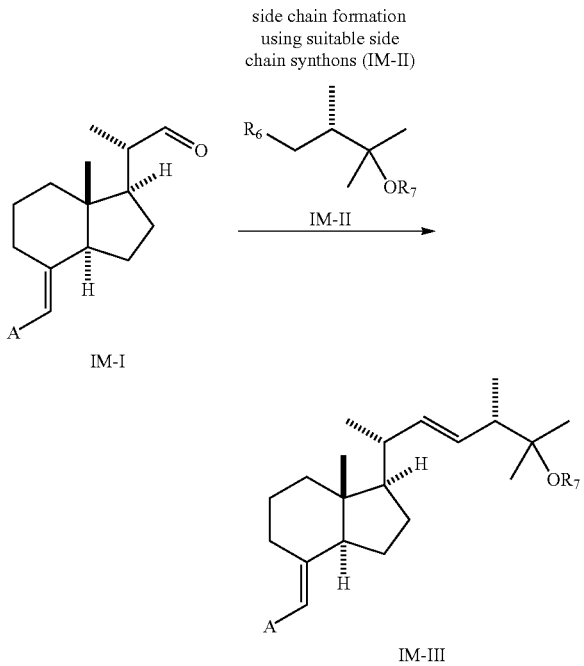

A = ring A fragment of a vitamin D derivative selected from:

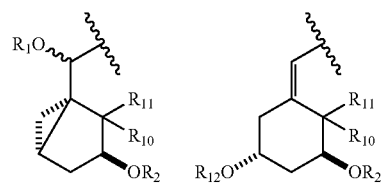

$R_1$ = $C_1$-$C_4$ alkyl
$R_2$ = Si($R_3$)($R_4$)($R_5$)
$R_3$, $R_4$, $R_5$ = independently $C_1$-$C_4$ alkyl, Ph
$R_6$ = $Ph_3P^+$, $PhSO_2$, $R_9SO2$
$R_7$ = H, $R_8$
$R_8$ = hydroxyl protection group
$R_9$ = BT, PY, PT, TBT, BTFP
$R_{10}$, $R_{11}$ = independently H, OH; $R_{10}$ = $R_{11}$ = H; $R_{10}$ + $R_{11}$ = O
$R_{12}$ = $C_1$-$C_4$ acyl, benzoyl Suitable side chain synthons (IM-II) for the installation of the paricalcitol side chain into compounds IM-I (Scheme 12) are specifically shown in Scheme 13.

Scheme 13: Synthetic overview for preparation of side chain synthons of formula IM-II wherein X = Ph$_3$P$^+$, PhSO$_2$, R$_9$SO$_2$, R$_7$ = H or R$_8$

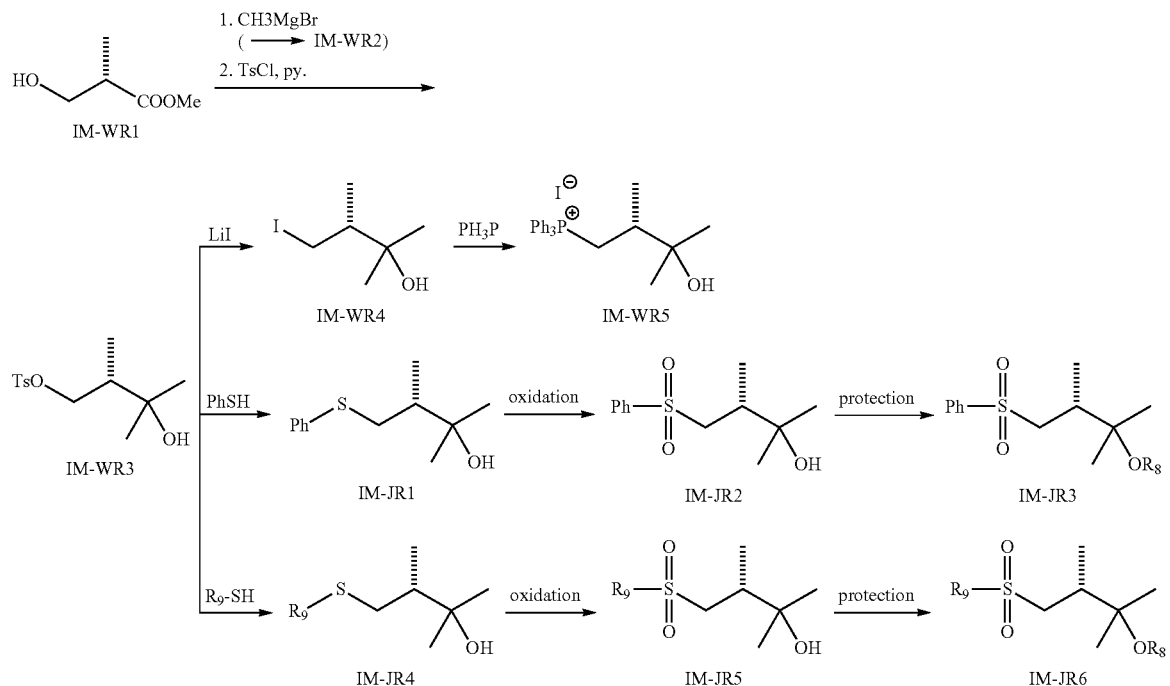

R$_8$ = hydroxy protecting group
R$_9$ = BT, PY, PT, TBT, BTFP

Compounds like IM-WR5 and IM-JR2 or IM-JR3 bearing the tertiary hydroxy group can be prepared according to method described by J. C. Hanekamp et al., *Tetrahedron Letters*, 1991, 32, 5397-5400, J. C. Hanekamp et al., *Tetrahedron*, 1992, 48, 5151-5162, J. C. Hanekamp et al., *Tetrahedron*, 1992, 48, 9283-9294, A. Kutner et al., *J. Org. Chem.*, 1988, 53, 3450-3457 or as disclosed in WO 91/12240.

According to P. R. Blakemore, *J. Chem. Soc., Perkin Trans.* 1, 2002, 2563-2585, the classical Julia olefination is a relatively cumbersome affair and typically requires four distinct synthetic operations (exemplary shown in Scheme 14) which would accordingly consist in this case of metallation of e.g. the phenylsulfone IM-JR3, addition of the corresponding metallate (IM-JR3-Li) to compounds IM-I, acylation of the resulting β-alkoxysulfone (IM-IV), and reductive elimination of the thus obtained β-acyloxysulfone (IM-V) using toxic sodium mercury amalgam.

Scheme 14:

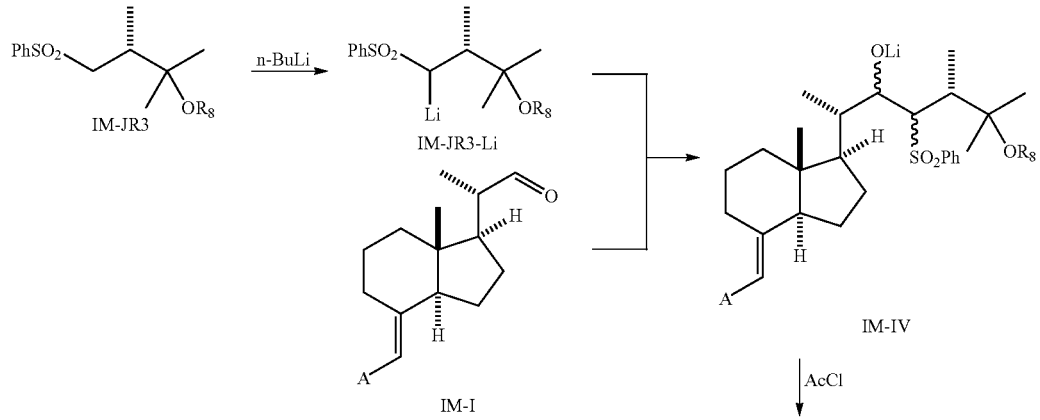

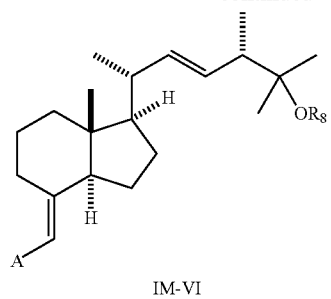

IM-VI

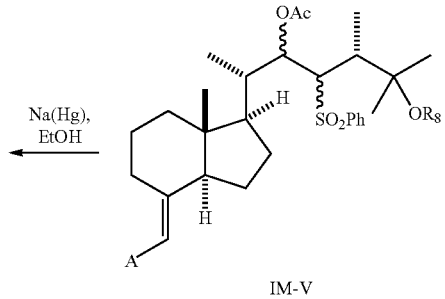

IM-V $R_6$ = ring A fragment of
a vitamin D derivative
$R_7$ = H, $R_8$
$R_8$ = hydroxyl protection group An advanced approach is the olefination using modified Julia reagent (see P. R. Blakemore, *J. Chem. Soc., Perkin Trans. 1*, 2002, 2563-2585). In case of the preparation of the modified Julia reagent as synthon for the installation of the paricalcitol side chain, compounds like IM-JR5 and IM-JR6 may be used. $R_8$ represents a hydroxyl protecting group which is compatible with the conditions used for installation of the side chain in compounds of formula IM-I (Scheme 12). Such hydroxy protecting groups may be selected from those as described by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0). $R_9$ may be selected from those groups which are typically used for the modified Julia olefination (as e.g. described by P. R. Blakemore, *J. Chem. Soc., Perkin Trans. 1*, 2002, 2563-2585, D. A. Alonso, *Tetrahedron Letters*, 2004, 45, 573-577, P. R. Blakemore et al., *Org. Biomol. Chem.*, 2005, 3, 1365-1368). With respect to the preparation of paricalcitol, different routes are possible for the preparation of the final compound starting with the key intermediate 2 (see FIG. 3-10).

The synthetic methods for the preparation of paricalcitol are now described in detail.

(A) Preparation of the Side Chain Synthons IM-WR5, IM-JR2/IM-JR3 and IM-JR5/IM-JR6 (Scheme 13)

(1) Preparation of IM-WR3 as Starting Material for the Synthesis of IM-WR5, IM-JR2 and IM-JR3 as Well as IM-JR5 and IM-JR6 (Scheme 13)

The preparation of IM-WR3 and IM-WR5 as well as IM-JR2 and IM-JR3 wherein $R_8$ is THP or TES can be carried out according to known procedures described by J. C. Hanekamp et al., *Tetrahedron Letters*, 1991, 32, 5397-5400, J. C. Hanekamp et al., *Tetrahedron*, 1992, 48, 5151-5162, J. C. Hanekamp et al., *Tetrahedron*, 1992, 48, 9283-9294, A. Kutner et al., *J. Org. Chem.*, 1988, 53, 3450-3457 or as disclosed in WO 91/12240.

Thus in a typical procedure IM-WR1 is reacted with 3.5 eq. MeMgBr in diethyl ether at 15° C. to 25° C. to give IM-WR2 which is isolated after aqueous quenching from the aqueous layer by continuous extraction using diethyl ether. IM-WR2 is then reacted with p-toluenesulfonyl chloride in pyridine as solvent yielding IM-WR3 which is further reacted with 1.17 eq. LiI in THF giving IM-WR4. Substitution of iodine in IM-WR4 by triphenylphosphine carried out in acetonitrile as solvent resulted in the formation of IM-WR5.

Starting with IM-WR3, IM-JR3 may be prepared according to the method described in WO 91/12240. Thus the tosylate (IM-WR3) is reacted in DMF with thiophenol and tert.-BuOK to yield the sulfide IM-JR1. The sulfide IM-JR1 can be then oxidized using 3-chloroperoxybenzoic acid to give the sulfone IM-JR2. Protection of the hydroxyl group as tetrahydropyranylether can be obtained by reaction of IM-JR2 with dihydropyran in presence of pyridinium p-toluenesulfonate. The corresponding triethylsilyl (TES) protected derivative can be prepared by reaction of IM-JR2 with TESCl in the presence of imidazole.

(2) Preparation of IM-JR6 Starting from IM-WR3 (Schemes 13, 15)

Scheme 15:

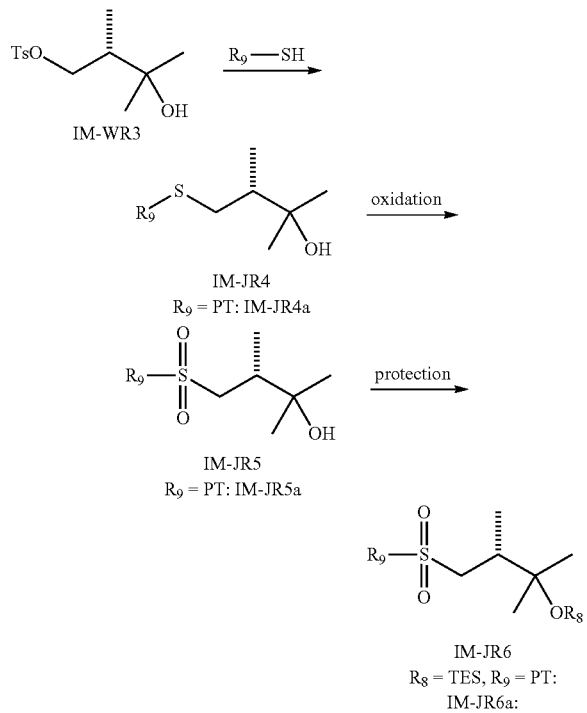

The synthesis of the corresponding modified Julia reagent is shown in schemes 13 and 15.

$R_8$ represents a hydroxy protecting group which is preferably selected from silyl protecting groups and which is most preferably a triethylsily group (TES).

$R_9$ is preferably selected from benzothiazol-2-yl, pyrid-2-yl, 1-phenyl-1H-tetrazol-5-yl, 1-tert.-butyl-1H-tetrazol-5-yl or 3,5-bistrifluoromethyl)phenyl. In a more preferred embodiment $R_9$ is selected from 1-phenyl-1H-tetrazol-5-yl or 1-tert.-butyl-1H-tetrazol-5-yl with 1-phenyl-1H-tetrazol-5-yl being most preferred.

It has now been found that compounds of the formula

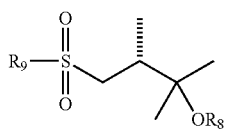

IM-JR6 wherein $R_8$ represents a hydroxyl protecting group and $R_9$ represents benzothiazol-2-yl, pyrid-2-yl, 1-phenyl-1H-tetrazol-5-yl, 1-tert-butyl-1H-tetrazol-5-yl or 3,5-bistrifluoromethylphenyl, can be obtained by a process comprising the steps of:

(a) reacting a compound of the formula

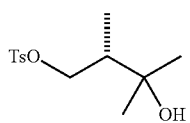

IM-WR3 with a compound of the formula
$R_9$—SH
wherein $R_9$ represents benzothiazol-2-yl, pyrid-2-yl, 1-phenyl-1H-tetrazol-5-yl, 1-tert.-butyl-1H-tetrazol-5-yl or 3,5-bistrifluoromethylphenyl to obtain a compound of the formula

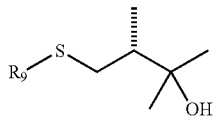

IM-JR4 wherein $R_9$ is defined as above;

(b) oxidizing a compound of the formula IM-JR4 to obtain a compound of the formula

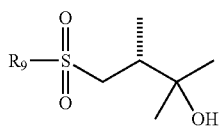

IM-JR5 wherein $R_9$ is defined as above and (c) protecting the tertiary hydroxyl group in a compound of the formula IM-JR5 to obtain a compound of the formula

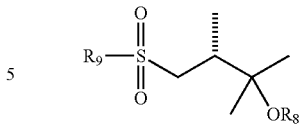

IM-JR6 wherein $R_8$ is a hydroxyl protecting group and wherein $R_9$ is defined as above.

The compounds of the formula IM-JR4 have not been disclosed before, and as novel compounds they also form part of the invention.

The compounds of the formula IM-JR6 have not been disclosed before, and as novel compounds they also form part of the invention.

The compounds of the formula IM-JR6 are useful and novel synthons for the introduction of the paricalcitol side chain into compounds of the formula IM-1 (scheme 12). The first step (process step (a)) for the preparation of the modified and protected Julia reagents (IM-JR6) involves a substitution of the tosylate group in IM-WR3 by the thiol $R_9$—SH in the presence of a suitable base. Suitable procedures for the nucleophilic displacement of the tosylate by the thiol $R_9$—SH are generally known for those skilled in the art. Such reaction is conveniently carried out in the presence of an tetraalkylammonium iodide like tetrabutylammonium iodide or alkali metal iodide like NaI or LiI in order to accelerate the reaction and to obtain an almost complete conversion (>90%). The presence of preferably 1 eq. tetraalkylammonium iodide, NaI or preferably LiI causes the formation of IM-WR4 as an intermediate which is not isolated and reacted directly with $R_9$—SH yielding IM-JR4. About 1.0 eq. to about 1.5 eq. of $R_9$—SH may be used, and about 1.2 eq. are preferred.

In a convenient procedure for preparing IM-JR4 (in process step (a)), suitable solvents may be selected from ketones, ethers, esters or the like, preferably from ethers like THF, dimethoxyethane (DME) or dioxane and is most preferably THF.

Suitable bases in process step (a) are selected from alkali metal or alkaline-earth metal hydroxides, alkoxides or carbonates, sodium hydride or tertiary amines like triethylamine, diisopropylethyl amine or the like. Preferred bases are alkali metal carbonates, sodium hydride and tertiary amines and most preferred is triethylamine. About 1.0 eq. to about 3.0 eq. of the base may be used and about 1.5 eq. are preferred.

It will be apparent to those skilled in the art that only such solvents and bases should be combined which are compatible to each other. The reaction of process step (a) is preferably carried out at temperatures from 40° C. to 80° C. or to reflux temperature when the boiling point of the solvent is <80° C.

After completion of the reaction of process step (a), the mixture can be worked up in a common manner, e.g. by evaporation of the reaction solvent, dilution of the residue with water and extraction of the product with a water-immiscible organic solvent like MTBE or ethyl acetate. Evaporation of the solvent from the organic extract yields the desired product, which can be used without purification for the next step.

Thus in a typical procedure IM-WR3 is reacted with 1.17 eq. LiI in THF at reflux until an in-process HPLC control showed an almost complete conversion to IM-WR4. Then 1.2 eq. PT-SH and 1.5 eq. triethylamine are added. The mixture is heated reflux until an in-process HPLC control shows an almost complete conversion to IM-JR4a. After filtration of the suspension, the filtrate is evaporated, diluted with water and MTBE and the aqueous layer is extracted with MTBE. Separation of the phases and evaporation of the solvent from the organic layer give IM-JR4a.

Generally, the oxidation of the sulfides to the corresponding sulfone of process step (b) is well established and many methods may be used in order to oxidize IM-JR4 to IM-JR5. Non limiting examples for oxidizing reagents, which may be used in process step (b), are e.g. organic peroxyacids like peracetic acid, meta chloroperbenzoic acid (mCPBA), magnesium bis(monoperoxyphthalate) as well as sodium perborate, OXONE®, hydrogen peroxide or its adduct with urea (UHP) in the presence of a catalyst like $MoO_3$, $MeReO_3$, $Na_2WO_4$ or the like. Particularly preferred is mCPBA. The oxidation is typically carried out in a suitable, compatible solvent like water, alcohols like methanol or ethanol or halogenated hydrocarbons like methylene chloride. It will be apparent to persons skilled in the art that for the preparation of the sulfones from sulfides, at least two equivalents of the oxidation reagent are necessary.

Thus in a typical procedure IM-JR4a is reacted with 3 eq. mCPBA in methylene chloride at room temperature until an in-process HPLC control shows an almost complete conversion to IM-JR5a. The mixture is filtered, the excess mCPBA destroyed by using aq. sodium bisulfite solution and the product is isolated by extractive work up. The crude product can be used directly for the next step.

For the introduction of a suitable protection group ($R_8$) in IM-JR5 giving IMJR6, silyl protecting groups are preferred in process step (c) and most preferred is the triethylsilyl group (TES). The conditions for protecting IM-JR5 resulting in the formation of IM-JR6 are generally known for those skilled in the art and may be selected from methods described by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0).

Thus in a typical procedure IM-JR5a is reacted with 2.0 eq. TESCl in DMF as solvent and in the presence of 3.0 eq. DMAP at a temperature ranging from 20° C. to 30° C. until an in-process HPLC control shows an almost complete conversion to IM-JR6a. The reaction mixture is then poured into a mixture of water and a water-immiscible solvent, e.g. MTBE, and the product is isolated by extractive work up. The crude product is purified by column chromatography using cyclohexane/ethyl acetate (5:1, v/v) as eluant.

(B) Preparation of Paricalcitol Starting from Vitamin D2 (FIG. 3-10)

Generally it should be noted, that during the course of the preparation of paricalcitol according to routes A1, B1, B2, C1 or C2 (FIG. 3-10), diastereomers are obtained since new stereogenic centers and/or double bonds are formed.

The composition of the diastereomers depends on the specific conditions chosen for the corresponding transformation. Thus in some cases C(6)- and/or C(10)- and/or C(5),C(6)-diastereomeric intermediates are obtained, e.g. during the transformation of compounds IM-A1 to IMA2, IM-A6 to IM-A7, IM-A5 to IM-B6, IM-A9 to IM-A10 and IM-B9 to IM-B10 (see FIGS. 4, 6, 7, 9 and 10). It will be apparent to those skilled in the art that the C(6)- and/or C(10)-diastereomers as well as the C(5),C(6)-diastereomers can be used as precursors or suitable intermediates for the preparation of paricalcitol, and in cases wherein such diastereomeric mixture is obtained, a separation of the isomers is optional but generally not necessary.

All other diastereomers which may be formed during the course of the synthesis of paricalcitol (e.g. C(22),C(23)-diastereomers (E/Z isomers) which may be obtained during installation of the side chain) are undesired and may be removed by using common techniques like column chromatography, (preparative) HPLC and/or crystallization.

It should be furthermore noted that cyclovitamin derivatives are generally sensitive to acids which may cause rearrangement and/or decomposition of the cyclovitamin structure. Acids, e.g. protic acids such as p-toluenesulfonic acid and/or acetic acid, are used for rearrangement of the cyclovitamin derivatives to the vitamin derivatives (see e.g. Zhu and William H. Okamura, *Chem. Rev.* 1995, 95, 1727-1952). As a consequence, in such cases wherein compounds consisting of the typical cyclovitamin structure are prepared and isolated, the presence of acids which are able to catalyse rearrangement and/or decomposition during the reaction or work up procedure should be avoided.

It has now been found that 19-nor-1α,3β,25-trihydroxy-9,10-secoergosta-5(Z),7(Z),22(E)-triene (paricalcitol) can be obtained by a process (via routes C1/C2) comprising the steps of (a) subjecting a compound of the formula

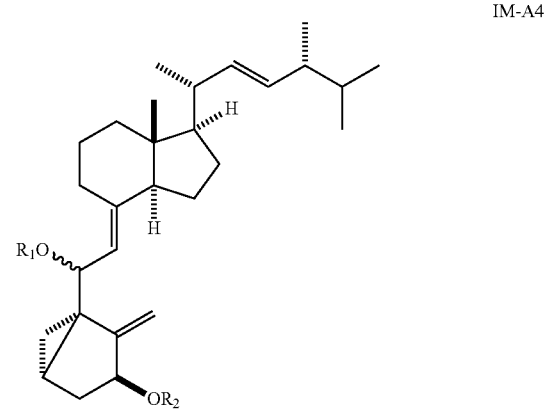

IM-A4 wherein
R₁ represents a $C_1$-$C_4$ alkyl group and
R₂ represents a hydroxyl protecting group
to ozonolysis, in an inert solvent and, if appropriate, in the presence of a base, and wherein upon completion the ozonolysis reaction mixture is quenched with a reducing agent to obtain a compound of the formula

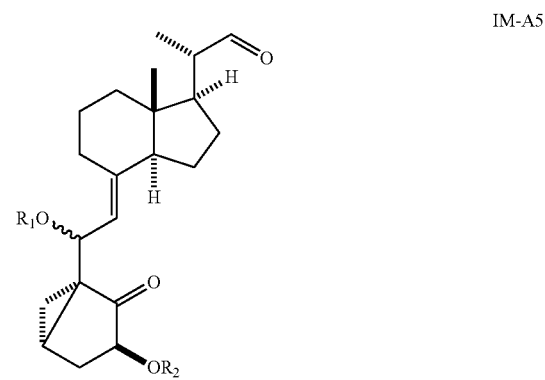

IM-A5 wherein R₁ and R₂ are defined as above;

(b) reacting a compound of the formula IM-A5 with a reducing agent, if appropriate in an inert solvent to obtain a compound of the formula

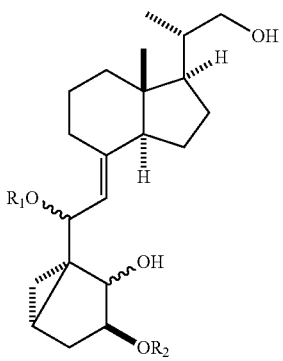

IM-B6 wherein $R_1$ and $R_2$ are defined as above;

(c) protecting the primary hydroxyl group in a compound of the formula IM-B6 with a hydroxyl protecting agent if appropriate in an inert solvent and if appropriate in the presence of a base to obtain a compound of the formula

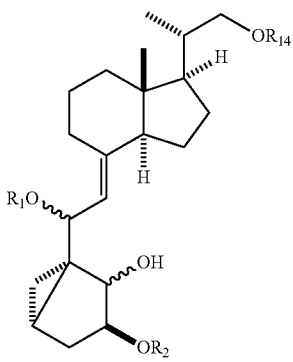

IM-B7 wherein $R_1$ and $R_2$ are defined as above and $R_{14}$ represents a hydroxyl protecting group;

(d) reacting the secondary hydroxyl group in a compound of the formula IM-B7 in the presence of a tertiary aromatic amine with a sulfonylating agent of the formula $(R_{13}SO_2)_2O$, wherein $R_{13}$ represents $C_1$-$C_4$ alkyl, unsubstituted aryl or aryl substituted by $C_1$-$C_2$ alkyl or halogen, if appropriate, in the presence of a solvent to obtain a compound of the formula

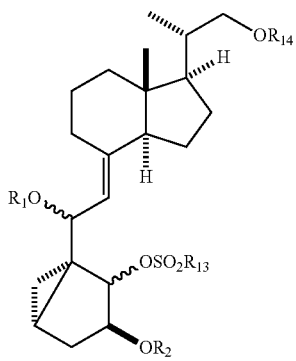

IM-B8 wherein $R_1$, $R_2$, $R_{13}$ and $R_{14}$ are defined as above;

(e) reacting a compound of the formula IM-B8 with a reducing agent, if appropriate, in a solvent in order to reduce the sulfonic ester group and reacting the primary hydroxyl group with a deprotecting agent to obtain a compound of the formula

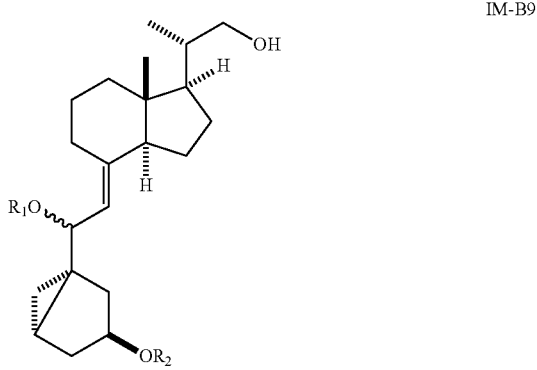

IM-B9 wherein $R_1$ and $R_2$ are defined as above;

(f) reacting a compound of the formula IM-B9 with an oxidizing agent, if appropriate, in a solvent and, if appropriate, in the presence of a base to obtain a compound of the formula

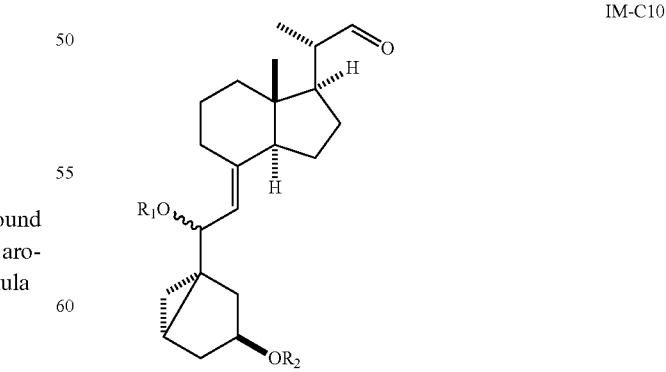

IM-C10 wherein $R_1$ and $R_2$ are defined as above;

(g) reacting a compound of the formula IM-C10 with a compound of the formula

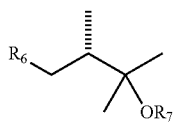

IM-II wherein $R_6$ represents $Ph_3P^+$ or $R_9SO_2$, wherein $R_9$ represents benzothiazol-2-yl, pyrid-2-yl, 1-phenyl-1H-tetrazol-5-yl, 1-tert.-butyl-H-tetrazol-5-yl or 3,5-bistrifluoromethylphenyl with the proviso that if $R_6$ is $Ph_3P^+$ that $R_7$ is hydrogen and $R_7$ represents hydrogen or $R_8$ and wherein $R_8$ represents a hydroxyl protecting group and wherein the compound of the formula IM-II is deprotonated with a base, if appropriate, in a solvent prior to reaction with a compound of the formula IM-C10 to obtain a compound of the formula

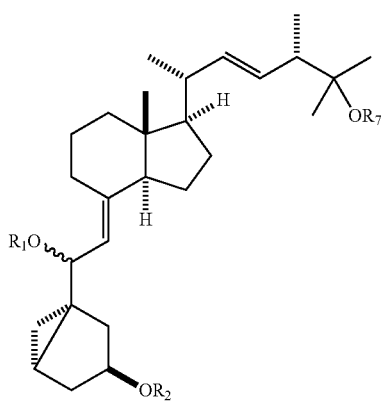

IM-A9 wherein $R_1$, $R_2$ and $R_7$ are defined as above;

(h) optionally to step (g), reacting a compound of the formula IM-C10 as defined in step (f)

with a compound of the formula

IM-II wherein $R_6$ represents $PhSO_2$ and $R_7$ represents a hydroxyl protecting group and wherein the compound of the formula IM-II is deprotonated with a base, if appropriate, in a solvent prior to reaction with a compound of the formula IM-C10 to obtain a compound of the formula

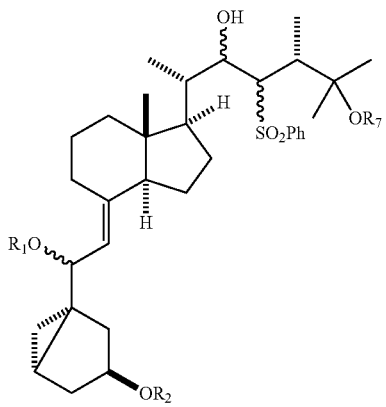

IM-C11 wherein $R_1$, $R_2$ and $R_7$ are defined as above and wherein a compound of the formula IM-C11 is then subjected to a reductive desulfonylation, optionally after acylation of the C(22) hydroxy group, to obtain a compound of the formula IM-A9 wherein $R_1$, $R_2$ and $R_7$ are defined as above;

(i) subjecting a compound of the formula IM-A9 to solvolysis with a $C_1$-$C_4$ carboxylic acid or a mixture consisting of DMSO and a $C_1$-$C_4$ carboxylic acid to obtain a mixture of the compounds of the formulae IM-A10 (I/II)

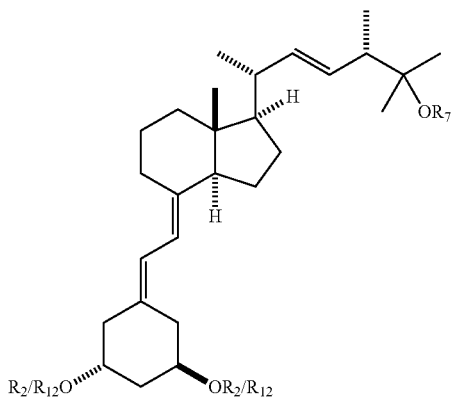

IM-A10 (I/II)

wherein $R_1$, $R_2$ and $R_7$ are defined as above and $R_{12}$ represents hydrogen or a $C_1$-$C_4$ acyl group; and (j) reacting the mixture of the compounds of the formulae IM-A10 (I/II) with a deprotecting agent, if appropriate, in a solvent to obtain paricalcitol.

The compounds of the formulae IM-A5, IM-B6, IM-B7, IM-B8, IM-B9 and IM-C10 have not been disclosed before, and as novel compounds they also form part of the invention. The compounds of the formulae IM-A5, IM-B6, IM-B7, IM-B8, IM-B9 and IM-C10 are obtained according to the novel process via routes C1 or C2, respectively, as described above.

This process starting from the intermediate IM-A4 forms part of the processes according to routes C1 and C2, respectively, which are depicted in FIGS. 9 and 10.

The following process steps of the above described process are depicted in FIG. 9 showing the general synthesis of paricalcitol according to route C1:

step (a)=step 5a) of FIG. 9
step (b)=step 5b) of FIG. 9
step (c)=step 6) of FIG. 9
step (d)=step 7) of FIG. 9
step (e)=step 8) of FIG. 9
step (f)=step 9) of FIG. 9
step (g)=step 10) of FIG. 9
step (i)=step 11) of FIG. 9 and
step (j)=step 12) of FIG. 9.

If the above process starting from the intermediate IM-A4 proceeds via process steps (a), (b), (c), (d), (e), (f), (h), (i) and (j), the process reflects route C2 depicted in FIG. 10.

Accordingly, the above process steps (a) to (f) correspond to process steps 5a to 9 of FIG. 10, process step (h) corresponds to steps 10 and 11 of FIG. 10 and process steps (i) and (j) correspond to steps 12 and 13 of FIG. 10, respectively.

The process for preparing paricalcitol via routes C1 or C2 is preferred, particularly preferred is the preparation of paricalcitol via route C1.

Process Step (a) of Routes C1/C2

The compounds required as starting materials in process step (a) of the process according to the invention are defined by the general formula IM-A4, In the formula IM-A4 $R_1$ preferably represents a methyl group.

In the formula IM-A4 $R_2$ represents a hydroxyl protecting group. Suitable hydroxyl groups are all common hydroxyl protecting groups as described e.g. by P. G. M. Wuts and T. W. Green in *Green's Protective Groups in Organic Synthesis*, fourth edition 2007, published by John Wiley and Sons, Inc. Hoboken, N.J. These preferably include silyl protection groups, dimethoxymethyl ether (MOM ether), tetrahydropyranyl ether (THP ether), tert-butyl ether, allyl ether, benzyl ether, acetic acid ester, pivalic acid ester and benzoic acid esters. $R_2$ preferably represents —Si($R_3$)($R_4$)($R_5$), wherein $R_3$, $R_4$ and $R_5$ are independently $C_1$-$C_4$ alkyl groups or phenyl groups. Most preferably, $R_2$ represents a tert-butyldimethylsilyl (TBS) group or a triethylsilyl (TES) group. Particularly preferred is the tert-butyldimethylsilyl (TBS) group.

The compounds of the formula IM-A4 have not been disclosed before, and as novel compounds they also form part of the invention. Particularly preferred are compounds of the formula IM-A4e as defined above.

The compounds of the formula IM-A4 can be obtained according to processes described below.

The ozonolysis of process step (a) is generally performed according to methods known to the skilled person and in particular as described below.

In process step (a) according to the invention, the reaction temperature may be varied over a relatively wide range. The ozonolysis is generally carried out at temperatures from −80° C. to −40° C., preferably at temperatures from −80° C. to −60° C.

Suitable solvents in process step (a) according to the invention are all inert organic solvents or mixtures of inert organic solvents whose freezing point is below the temperature range used for the ozonolysis reaction. These preferably include aliphatic, alicyclic or aromatic hydrocarbons, such as for example pentane, hexane or toluene, alcohols such as methanol, ethanol, n- or i-propanol, n-, i-, or sec-butanol, ethoxyethanol, methoxyethanol, diethlene glycolmonomethyl ether or diethylene glycolmonoethyl ether; halogenated hydrocarbons such as, for example, chlorobenzene, dichloromethane or chloroform; esters such as methyl acetate or ethyl acetate; and ethers such as, for example, THF, methyl-tert.-butyl ether (MTBE), dimethoxyethane (DME) or diethylether and their mixtures. Particularly preferred solvents are dichloromethane, $C_1$-$C_4$ alcohols such as methanol, ethanol, n- or i-propanol, n-, i- or sec-butanol or ethyl acetate or a mixture thereof. A particular preferred solvent is dichloromethane (methylene chloride).

In the work-up procedure of process step (a), the ozonolysis reaction mixture is quenched with a reducing agent. Suitable reducing agents include dialkylsulfides such as, for example, dimethyl sulfide or diethylsulfide; zinc dust; and trialkyl- or triarylphosphines such as, for example, tributylphosphine or triphenylphosphine; trialkylphosphites such as, for example, trimethylphosphite or triethylphosphite; and sodium bisulfite. Particularly preferred are the reducing agents dimethylsulfide or triphenylphosphine.

Process step a) is, if appropriate, carried out in the presence of a base. Suitable bases include all common organic bases. These preferably include tertiary amines, such as trimethylamine, triethylamine, tributylamine, N,N-dimethylaniline, 2-, 3- or 4-picoline, 2,6-lutidine, pyridine, N-alkylpiperidine such as, for example N-methyl piperidine or N-ethyl piperidine, N-alkyl morpholine such as, for example N-methyl morpholine or N-ethyl morpholine, imidazole or N-alkylimidazole such as, for example N-methylimidazole or N-ethylimidazole. Bases having a higher pKa value such as, for example, diazabicyclononene (DBN) or diazabicycloundecene (DBU) should be avoided due to possible epimerization of the 22-aldehyde group obtained after the quenching reaction. Particularly preferred is pyridine.

Process Step (b) of Routes C1/C2

Process step (b) is carried out in the presence of a suitable reducing agent. These are all common hydride reagents. These preferably include lithium aluminium hydride, borane tetrahydrofurane complex ($BH_3$).THF, sodium borohydride, sodium cyanoborohydride, diisobutylaluminium hydride and lithiumtri-t-butoxyaluminium hydride. Particularly preferred is sodium borohydride.

Suitable inert solvents in process step (b) according to the invention are all inert organic solvents mentioned above for process step (a). If stronger reducing agents than sodium borohydride are used then protic solvents like alcohols or solvents like esters should be avoided. Particularly preferred is ethanol.

In process step (b) according to the invention, the reaction temperature may be varied over a relatively wide range. The reduction is generally carried out at temperatures from 0° C. to room temperature, preferably at room temperature.

Process Step (c) of Routes C1/C2

Suitable hydroxyl protecting agents of step (c) are all common hydroxyl protecting agents which results in the formation of a protection group that can be cleaved under neutral or alkaline conditions. Particularly preferred are acetyl chloride and benzoyl chloride.

Suitable inert solvents in process step (c) according to the invention include aliphatic, alicyclic or aromatic hydrocarbons, such as for example pentane, hexane or toluene; halogenated hydrocarbons or halogenated hydrocarbons such as, for example, chlorobenzene, dichloromethane, chloroform, dichloroethane or trichloroethane; esters such as methyl acetate or ethyl acetate; and ethers such as, for example, THF, methyl-tert.-butyl ether (MTBE), 1,2-dimethoxyethane (DME), 1,2-diethoxyethane, diethylether or their mixtures. Particularly preferred is methylene chloride.

Suitable bases in process step (c) according to the invention are all bases mentioned above for process step (a).

In process step (c) according to the invention, the reaction temperature may be varied over a relatively wide range. Process step (c) is generally carried out at temperatures from −20° C. to 50° C., preferably from −5° C. to RT.

In the compounds of the formula IM-B7, $R_{14}$ preferably represents substituted or unsubstituted acyl groups like formyl, acetyl, chloroacetyl, dichloroacetyl, trichloroacetyl, methoxyacetyl or benzoyl, $C_1$-$C_2$ trialkylsilyl groups such as trimethylsilyl, triethylsilyl, or (alkoxy)(alkyl)(aryl)silyl such as tert.-butylmethoxyphenylsilyl, particularly preferred are substituted or unsubstituted acyl groups, most preferred is acetyl or benzoyl.

Process Step (d) of Routes C1/C2

The sulfonylating agents of the formula $(R_{13}SO_2)_2O$ required in process step (d) according to the invention are known chemicals for synthesis. $R_{13}$ preferably represents methyl, ethyl, benzyl, phenyl, methylphenyl or ethylphenyl. Particularly preferred sulfonylating agents are methane sulfonic acid anhydride or p-toluene sulfonic acid anhydride. Particular preference is given to methane sulfonic acid anhydride.

Process step (d) according to the invention is carried out in the presence of a tertiary aromatic amine or tertiary aryl amine. Suitable tertiary amines include N,N-dimethylaniline, N,N-diethylaniline, and N,N-dimethyl-p-toluidine, 2-, 3-, or 4-picoline, 2,6-lutidine, pyridine, imidazole, N-alkylimidazole such as, for example N-methylimidazole or N-ethylimidazole or mixtures thereof. Particular preference is given to pyridine.

Suitable solvents in process step (d) according to the invention are all inert solvents mentioned above for process step (c).

In process step (d) according to the invention, the reaction temperature is generally carried out a temperature ranging from 0° C. to room temperature, preferably at temperatures from 0° C. to 10° C.

Process Step (e) of Routes C1/C2

Process step (e) according to the invention is carried out in the presence of a reducing agent. Suitable reducing agents in process step (e) are lithium aluminium hydride or lithium triethylborohydride. Particularly preferred is lithium aluminium hydride.

If appropriate, suitable solvents in process step (e) according to the invention are all inert solvents mentioned above for process step (c) except esters and halogenated hydrocarbons. Particularly preferred is diethyl ether.

In process step (e), suitable deprotecting agents are in the case of esters the reducing agent itself (lithium aluminium hydride or lithium triethylborohydride) or alkali metal hydroxides such as for example lithium hydroxide, sodium hydroxide or potassium hydroxide and in the case of silyl ethers, tetraalkylammonium fluoride such as, for example, tetrabutyl ammonium fluoride.

In process step (e) according to the invention, the reaction temperature may be varied over a relatively wide range. Process step (e) is generally carried out at temperatures from –20° C. to RT, preferably at temperatures from –5° C. to 10° C.

Process Step (f) of Routes C1/C2

Suitable oxidizing agents in process step (f) according to the invention are all oxidizing agents which are appropriate to oxidize primary alcohols to aldehydes. These preferably include the oxidizing agents mentioned below. Particular preference is given to NCS/DMS, Dess-Martin periodinane or DMSO and oxalylchloride. Particularly preferred are DMSO and oxalylchloride.

Suitable inert solvents in process step (f) are all inert solvents mentioned above for process step (c). Particularly preferred is methylene chloride.

Suitable bases for NCS/DMS or DMSO/oxalylchloride oxidations in the practice of process step (f) are tertiary alkyl amines such as, for example, trimethylamine, triethylamine or diisopropylamine. Particular preference is given to triethylamine.

Advantageously, in case of DMSO/oxalylchloride oxidation, an additional base is added prior to the addition of the substrate and the tertiary alkyl amine to a mixture of the oxidation reagents in a solvent. Suitable bases are tertiary aromatic amines, such as, for example pyridine, 2-, 3- or 4-picoline or 2,6-lutidine. Particular preference is given to pyridine.

In process step (f) according to the invention, the reaction temperature may be varied over a relatively wide range depending on the oxidation method. NCS/DMS oxidation in process step (1) is generally carried out at temperatures from –50° C. to RT, preferably at temperatures from –40° C. to –10° C. Dess Martin periodinane oxidation in process step (f) is generally carried out at temperatures from –20° C. to RT, preferably at temperatures from 0° C. to RT. DMSO/oxalylchloride oxidation in process step (1) is generally carried out at temperatures from –80° C. to –40° C., preferably at temperatures from –80° C. to –50° C.

Process Step (g) of Route C1

The compounds of the formula are known chemicals for the synthesis and are obtained as described above. In the compounds of the formula IM-II, particular preference is given to compounds of the formula IM-II, wherein $R_6$ represents 1-phenyl-1H-tetrazo-5-sulfonyl (modified Julia reagent) and wherein $R_7$ represents triethylsilyl or wherein $R_6$ represents triphenylphospinyl and $R_7$ represents hydrogen (Wittig reagent).

Suitable inert solvents in process step (g) wherein the modified Julia reagent is used are inert solvents which include aromatic hydrocarbons such as, for example, toluene or ethers such as, for example, diethylether, THF, 2-methyl-THF, DME or dioxane or their mixtures. Particularly preferred is DME.

Suitable inert solvents in process step (g) wherein the Wittig reagent is used are inert solvents which include ethers such as, for example, diethylether, THF, 2-methyl-THF, DME or dioxane or their mixtures. Particularly preferred is diethylether.

Suitable bases in the practice of process step (g) wherein the modified Julia reagent is used include alkali metal hexamethyldisilazane such as lithium hexamethyldisilazane, potassium hexamethyldisilazane or sodium hexamethyldisilazane; lithium diisopropylamide (LDA); and aryl or alkyl lithium such as, for example, phenyl lithium, butyl lithium or methyl lithium. Particularly preferred is potassium hexamethyldisilazane.

Suitable bases in the practice of process step (g) wherein the Wittig reagent is used include butyl lithium, phenyl lithium or methyl lithium. Particularly preferred is methyl lithium.

In process step (g) according to the invention, the reaction temperature may be varied over a relatively wide range. In case of Julia olefination the deprotonation of the Julia reagent in process step (g) is generally carried out at temperatures from –80° C. to –20° C., preferably at temperatures from –60° C. to –20° C. while the coupling reaction is carried out at a temperature range from –50° C. to –10° C., preferably from –40° C. to –10° C.

In case of the Wittig reaction the deprotonation of the Wittig reagent in process step (g) is generally carried out at temperatures from –10° C. to RT, preferably at temperatures from 0° C. to room temperature while the coupling reaction is carried out at a temperature range from –40° C. to –10° C., preferably from –25° C. to –15° C.

Process Step (i) of Routes C1/C2

The solvolysis is carried out with a suitable $C_1$-$C_4$ carboxylic acid or a mixture consisting of DMSO and a $C_1$-$C_4$ carboxylic acid as described below. Particularly preferred is acetic acid.

In process step (i) according to the invention, the reaction temperature may be varied over a relatively wide range. Process step (i) is generally carried out at temperatures from RT to 80° C., preferably at temperatures from RT to 60° C.

Process Step (j) of Routes C1/C2

In case of ester groups most commonly deprotecting agents in process step (j) are alkali or alkaline earth metal hydroxides, carbonates or alkoxides such as, for example lithium hydroxide, sodium hydroxide, potassium hydroxide, magnesium hydroxide, magnesium methoxide, sodium carbonate, potassium carbonate or sodium methoxide. Particularly preferred is sodium hydroxide.

In case of silyl groups suitable deprotecting agents in process step (j) which are not simultaneously cleaved under the basic conditions used e.g. for ester hydrolysis include fluoride ion sources selected from $C_1$-$C_4$-tetraalkylammonium fluoride such as, for example, tetrabutyl ammonium fluoride; hydrogen fluoride in triethylamine; hydrogen fluoride-pyridine; sodium fluoride, potassium fluoride or cesium fluoride optionally in combination with e.g. tetraalkylammonium chloride. Particularly preferred is tetrabutyl ammonium fluoride.

Alternatively, silyl groups can be cleaved under acidic conditions using organic or mineral acids which include hydrochloric acid, sulfuric acid, methane sulfonic acid or acetic acid.

Suitable solvents in process step (j) are in case of ester hydrolysis $C_1$-$C_3$ alcohols such as, for example, methanol, ethanol or propanol or mixtures of the alcohols with water or a watermiscible solvent such as, for example, THF. Particularly preferred are methanol and mixtures of methanol with water.

Suitable solvents in process step (j) in case of silyl ether deprotection using a fluoride source are e.g. ethers such as THF, 2-Me-THF, 1,2-dimethoxyethane or dioxane; esters such as, for example methyl acetate or ethyl acetate; alkylnitriles such as for example acetonitrile or propionitril; aromatic hydrocarbon such as, for example, toluene; dimethyl formamide or dimethylacetamide. Particularly preferred is THF.

In process step (j) according to the invention, the reaction temperature may be varied over a relatively wide range. Process step (j) is generally carried out at temperatures from 0° C. to 40° C., preferably at temperatures from 15° C. to 25° C.

If paricalcitol is obtained via route C2 starting from the compound IM-A4 comprising the steps (a) to (f), (h), (i) and (j), in process steps (a)-(f), (i) and (j), the same reagents, solvents and bases are used as defined above.

Process Step (h) of Route C2

The compounds of the formula IM-II, which are used as reagents in process step (h) are obtained as described above.

In the formula IM-II, $R_7$ represents a common hydroxyl protecting group. Particularly preferred is the triethylsilyl group (TES group).

Suitable bases in process step (h) according to the invention are all bases mentioned above for process step (g).

Suitable solvents in process step (h) according to the invention are all inert solvents mentioned above for process step (g).

The reductive desulfonylation is carried out according to the procedure generally known to the skilled person, in particular according to the procedures as described below.

Alternatively, paracalcitol can be obtained by a process (via route A1) comprising after step (a):
(b) reacting a compound of the formula IM-A5 as defined in step a) of claim 4 with a compound of the formula

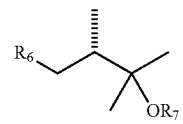

IM-II wherein
$R_4$ represents $R_9SO_2$, wherein
$R_9$ represents benzothiazol-2-yl, pyrid-2-yl, 1-phenyl-1H-tetrazol-5-yl, 1-tert.-butyl-1H-tetrazol-5-yl or 3,5-bis-trifluoromethylphenyl and
$R_7$ represents $R_8$ and wherein $R_8$ represents a hydroxyl protecting group, and
wherein the compound of the formula IM-II is deprotonated with a base, if appropriate, in a suitable solvent prior to reaction with a compound of the formula IM-A5 to obtain a compound of the formula

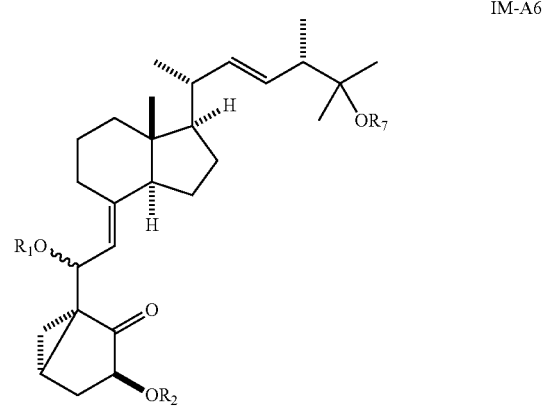

IM-A6 wherein $R_1$, R, and $R_7$ are defined as above;
(c) reacting a compound of the formula IM-A6 with a reducing agent in a solvent to obtain a compound of the formula

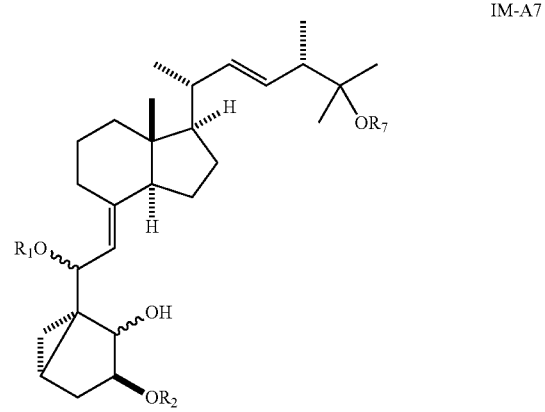

IM-A7 wherein $R_1$, $R_2$ and $R_7$ are defined as above;

(d) reacting the secondary hydroxyl group in a compound of the formula IM-A7 in the presence of a tertiary amine with a sulfonylating agent of the formula $(R_{13}SO_2)_2O,$ wherein $R_{13}$ represents C1-C$_4$-alkyl, unsubstituted aryl or aryl substituted by phenyl, phenyl-C$_1$-alkyl, C$_1$-C$_2$ alkyl substituted aryl or halogen substituted aryl to obtain a compound of formula IM-A8.

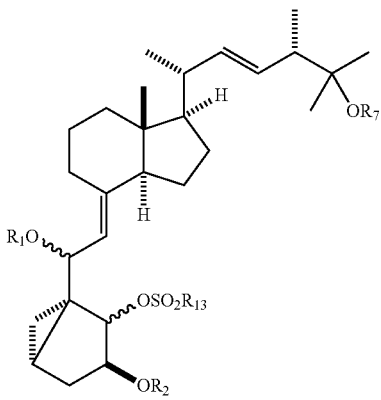

IM-A8 wherein $R_1$, $R_2$, $R_7$ and $R_{13}$ are defined as above;

(e) reacting a compound of the formula IM-A8 with a reducing agent, if appropriate, in a solvent in order to reduce the sulfonic acid ester group to obtain a compound of the formula

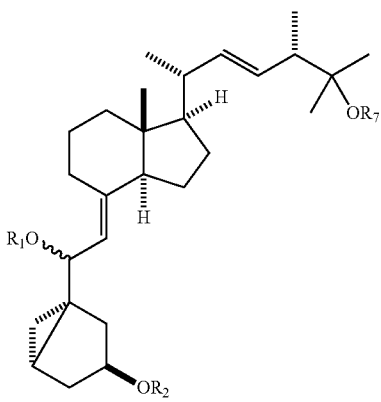

IM-A9 wherein $R_1$, $R_2$ and $R_7$ are defined as above;

(f) subjecting a compound of the formula IM-A9 to solvolysis with C$_1$-C$_4$ carboxylic acid or a mixture consisting of DMSO and a C$_1$-C$_4$ carboxylic acid to obtain a mixture of the compounds of the formulae

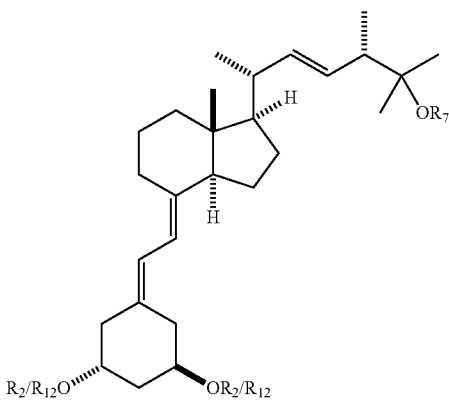

IM-A10 (I/II)

wherein $R_2$ and $R_7$ are defined as above and $R_{12}$ represents hydrogen or a C$_1$-C$_4$ acyl group; and (g) reacting the mixture of the compounds of the formulae IM-A10 (I/II) with a deprotecting agent, if appropriate, in a solvent to obtain paricalcitol.

Process Step (b) of Route A1

In process step (b) in the compounds of the formula IM-II, $R_8$ represents the same hydroxyl protecting groups as indicated above in process step (g) of route C1.

Suitable solvents for process step (b) are aromatic solvents, like toluene or ethers such as diethylether, THF, 2-methyl-THF, DME and dioxane or mixtures of aromatic solvents and ethers. Particularly preferred are ethers, DME is most preferred.

Suitable bases in process step (b) are selected from those as indicated in process step (g) of route C1. Particularly preferred is potassium hexamethyldisilazane.

In process step (b), the reaction temperature may be varied over a relatively wide range. The deprotonation may be carried out at a temperature range from −80° C. to −20° C., preferably from −60° C. to −20° C. while the coupling reaction may be carried out at a temperature range from −50° C. to −10° C., preferably from −40° C. to −10° C.

Process Step (c) of Route A1

Suitable reducing agents in process step (c) are all reducing agents mentioned above for process step (b) of route C1. Particularly preferred is sodium borohydride.

Suitable solvents in process step (c) are all solvents mentioned above for process step (b) of route C1.

For process step (c), the same temperatures are appropriate as for process step (b) of route C1.

Process Step (d) of Route A1

In process step (d), the sulfonylating agents of the formula $(R_{13}SO_2)_2O$ are defined as in process step (d) of route C1. Particularly preferred is methane sulfonic acid anhydride.

Suitable tertiary amines as well as suitable solvents in process step (d) are all tertiary amines and solvents, respectively, mentioned above for process step (d) of route C1.

For process step (d), the same temperatures are appropriate as for process step (d) of route C1.

Process Step (e) of Route A1

Suitable reducing agents and solvents, respectively, in process step (e) are all reducing agents and solvents, respectively, mentioned above for process step (e) of route C1. Particularly preferred is lithium aluminium hydride.

Process Step (f) of Route A1

The solvolysis of process step (1) is carried out as described above for process step (e) of route C1.

Process Step (g) of Route A1

Suitable deprotecting agents and solvents in process step (g) are all deprotecting agents and solvents, respectively, mentioned above for process step (j) of route C1.

For process step (g), the same temperatures are appropriate as for process step (j) of route C1.

Alternatively, paricalcitol can be obtained by a process (via routes B1/B2) comprising after step (e):

(f) subjecting a compound of the formula IM-B9 to solvolysis with a $C_1$-$C_4$ carboxylic acid to obtain a mixture of the compounds of the formulae

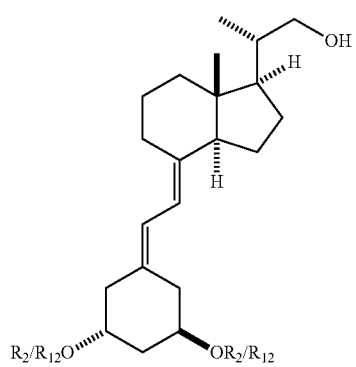

IM-B10 (I/II)

wherein $R_2$ is as defined above and $R_{12}$ represents a $C_1$-$C_4$ acyl group;

(g) reacting a mixture of the compounds of the formulae IM-B10 (I/II) with an oxidizing agent, if appropriate, in a solvent to obtain a mixture of the compounds of the formulae

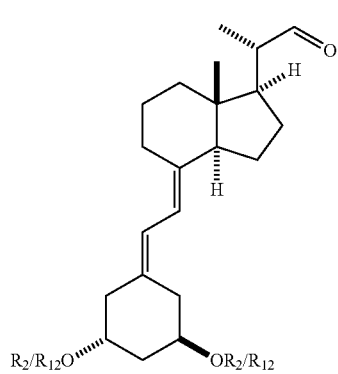

IM-B11 (I/II)

wherein $R_2$ and $R_{12}$ are defined as above;

(h) reacting the mixture of the compounds of the formulae IM-B11 (I/II) with a compound of the formula

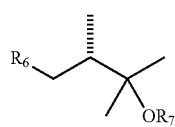

IM-II wherein $R_6$ represents $Ph_3P^+$ or $R_9SO_2$, wherein $R_9$ represents benzothiazol-2-yl, pyrid-2-yl, 1-phenyl-1H-tetrazol-5-yl, 1-tert.-butyl-1H-tetrazol-5-yl or 3,5-bistrifluoromethylphenyl with the proviso that if $R_6$ is $Ph_3P^+$ $R_7$ is hydrogen and $R_7$ represents hydrogen or $R_8$ and wherein $R_8$ represents a hydroxyl protecting group, and wherein a compound of the formula IM-II is deprotonated with a base in a solvent prior to reaction with a compound of the formulae IM-B11 (I/II) to obtain a mixture of the compounds of the formulae

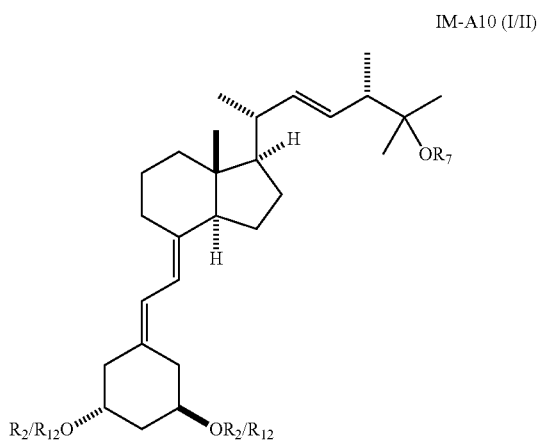

IM-A10 (I/II)

wherein $R_2$, $R_7$ and $R_{12}$ are defined as above;

(i) optionally to step (h), reacting the mixture of the compounds of the formulae IM-B11 (I/II) with a compound of the formula

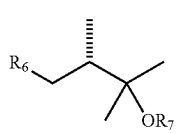

IM-II wherein $R_6$ represents $PhSO_2$ and $R_7$ represents a hydroxyl protecting group and wherein the compound of the formula IM-II is deprotonated with a base in a solvent prior to reaction with a compound of the formulae IM-B11 (I/II) to obtain a mixture of the compounds of the formulae

IM-B12 (I/II)

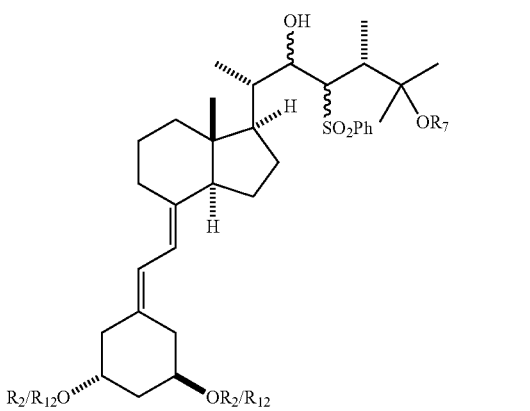

wherein $R_2$, $R_7$ and $R_{12}$ are defined as above, and
wherein the mixture of the compounds of the formulae IM-B12 (I/II) is then subjected to reductive desulfonylation, optionally after acylation of the C(22) hydroxy group, to obtain a compound of the formulae IM-A10 (I/II) wherein $R_2$, $R_7$ and $R_{12}$ are defined as above; and (j) reacting the mixture of the compounds of the formulae IM-A10 (I/II) with a deprotecting agent, if appropriate in a solvent, to obtain paricalcitol.

If the above process starting from the intermediate IM-A4 proceeds via steps (f), (g), (h) and (j), the process reflects route B1 depicted in FIG. 6.

If the above process starting from the intermediate IM-A4 proceeds via process step (f), (g), (i) and (j), the process reflects route B2 depicted in FIG. 7.

Process Step (f) of Routes B1/B2

The solvolysis in process step (f) is carried out with $C_1$-$C_4$ alkanoic acids according to process step (i) of route C1.

Process Step (g) of Route B1

Suitable oxidizing agents, solvents and bases, respectively, in process step (g) are all oxidizing agents, solvents, and bases, respectively, mentioned above for process step (f) of route C1.

For process step (g), the same temperatures are appropriate as for process step (1) of route C1.

Process Step (h) of Route B1

Suitable bases and solvents in process step (h) are all bases and solvents mentioned above for process step (g) of route C1.

For process step (h), the same temperatures are appropriate as for process step (g) of route C1.

Process Step (j) of Routes B1/B2

Suitable deprotecting agents and solvents in process step (j) are all deprotecting agents and solvents, respectively, mentioned above for process step (j) of route C1.

For process step (j), the same temperatures are appropriate as for process step (j) of route C1.

The process via route B2 is carried out via process step (i). The compounds of the formula IM-II used in process step (i) are defined as in process step (h) of route C1. The same applies to the bases as well as the reductive desulfonylation of process step (i).

(1) Synthesis of the Key Intermediate 1 (IM-A4)

Further, it has been found that the compounds of the formula IM-A4 as defined above are obtained by reacting a compound of the formula

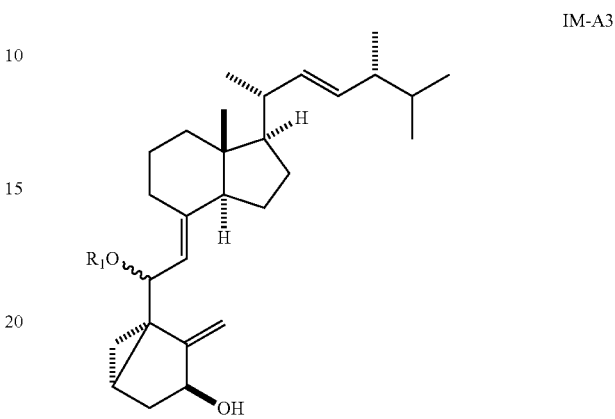

IM-A3 wherein $R_1$ is a $C_1$-$C_4$ alkyl group
with a silylating agent, if appropriate, in a solvent.

Suitable silylating agents are all typical silylating agents as described e.g. by P. G. M. Wuts and T. W. Green in Green's Protective Groups in Organic Synthesis, fourth edition 2007, published by John Wiley and Sons, Inc.; Hoboken, N.J. Particular preference is given to tert.-butyldimethylsilylchloride (TBSCl).

Particular preference is given to compounds of the formula IM-A3, wherein $R_1$ is a methyl group.

Surprisingly, the compounds of the formula IM-A4, wherein
$R_1$ represents a $C_1$-$C_4$ alkyl group and
$R_2$ represents a TBS group
are crystalline.

The use of crystalline compounds as intermediates for the production of active agents such as paricalcitol has the advantage that these compounds can be easily purified and thus obtained in high purity which is an important prerequisite for the preparation of medicaments.

Thus the use of a compound of the formula IM-A4 for the preparation of an active ingredient is part of the invention.

The synthesis of the key intermediate 1 (IM-A4) by using the procedure of DeLuca (U.S. Pat. No. 4,195,027) starts with the tosylation of vitamin D2 to IM-A1 followed by formation of the cyclovitamin derivative IM-A2, allylic oxidation to 1α-hydroxy-3,5-cyclovitamin D derivative IM-A3 and acylation of the hydroxyl group, resulting in the formation of compounds of formula IM-A4 wherein $R_1$ an alkyl group and $R_2$ a lower acyl or aromatic acyl group. During the cyclization, a new stereogenic center at position C(6) is formed resulting in a mixture of diastereomers from which the 6R*-diastereomer is formed as the major product (Scheme 16).

Scheme 16:

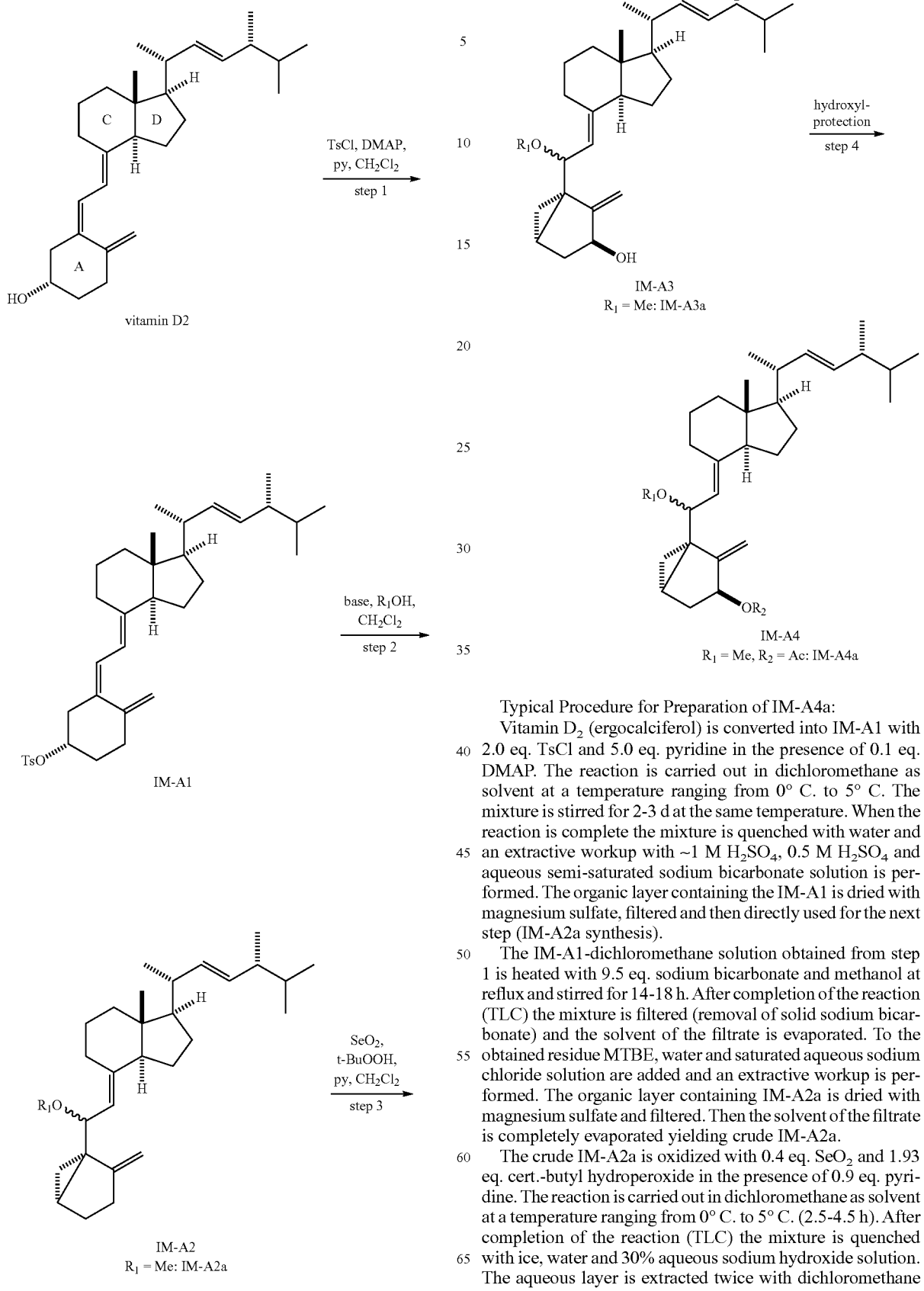

Typical Procedure for Preparation of IM-A4a:

Vitamin D$_2$ (ergocalciferol) is converted into IM-A1 with 2.0 eq. TsCl and 5.0 eq. pyridine in the presence of 0.1 eq. DMAP. The reaction is carried out in dichloromethane as solvent at a temperature ranging from 0° C. to 5° C. The mixture is stirred for 2-3 d at the same temperature. When the reaction is complete the mixture is quenched with water and an extractive workup with ~1 M H$_2$SO$_4$, 0.5 M H$_2$SO$_4$ and aqueous semi-saturated sodium bicarbonate solution is performed. The organic layer containing the IM-A1 is dried with magnesium sulfate, filtered and then directly used for the next step (IM-A2a synthesis).

The IM-A1-dichloromethane solution obtained from step 1 is heated with 9.5 eq. sodium bicarbonate and methanol at reflux and stirred for 14-18 h. After completion of the reaction (TLC) the mixture is filtered (removal of solid sodium bicarbonate) and the solvent of the filtrate is evaporated. To the obtained residue MTBE, water and saturated aqueous sodium chloride solution are added and an extractive workup is performed. The organic layer containing IM-A2a is dried with magnesium sulfate and filtered. Then the solvent of the filtrate is completely evaporated yielding crude IM-A2a.

The crude IM-A2a is oxidized with 0.4 eq. SeO$_2$ and 1.93 eq. cert.-butyl hydroperoxide in the presence of 0.9 eq. pyridine. The reaction is carried out in dichloromethane as solvent at a temperature ranging from 0° C. to 5° C. (2.5-4.5 h). After completion of the reaction (TLC) the mixture is quenched with ice, water and 30% aqueous sodium hydroxide solution. The aqueous layer is extracted twice with dichloromethane and the combined organic layers are dried with magnesium sulfate. The solvent is completely evaporated to give crude IM-A3a. The crude IM-A3a is purified with column chromatography with cyclohexane/ethyl acetate-gradient.

IM-A4a can be prepared according to the method disclosed in U.S. Pat. No. 4,195,027. Typically, and in a slightly modified procedure, IM-A3a is reacted with 1.5 eq. acetic acid anhydride in methylene chloride and in the presence of 2.5 eq. pyridine and 0.1 eq. DMAP at a temperature of 0° C. until a TLC control shows an almost complete conversion (>90%). After extractive work up using subsequently aq. sodium hydrogensulfate solution and aqueous sodium hydrogen carbonate solution followed by drying of the organic layer with magnesium sulfate, filtration and removal of the organic solvent gives the product as yellow oil.

Ozonolysis of IM-A4 Derivatives—Synthesis of IM-A5:

The ozonolysis was first tried with the compound of formula IM-A4a and it is carried out in an analogous manner as described by M. Takahashi, Y Sakakibara, *Bull. Chem. Soc. Jpn.*, 1994, 67, 2492-2499 (scheme 11 and 17). It was found that by trying to complete the conversion of IM-A4a and IM-A5BP1 to IM-A5a, in all cases considerable amounts of IM-A5BP2 are formed (up to 40 mol %) decreasing the yield of IM-A5a significantly (Scheme 17).

Scheme 17:

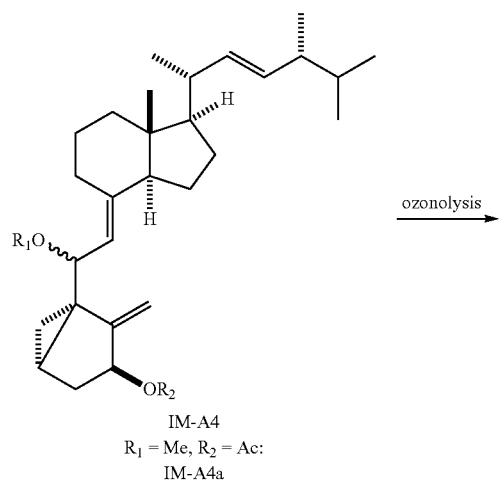

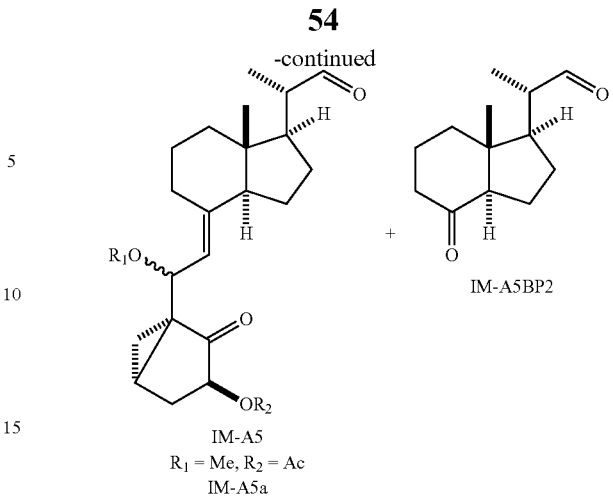

Unfortunately, attempts to optimize the ozonolysis of IM-A4a indicated that the formation of IM-A5BP2 could not be avoided and it was observed that in all cases IM-A5a reacted simultaneously to the side product IM-A5BP2 before IM-A5BP1 could be completely converted to IM-A5a. Furthermore, the impurity IM-A5BP2 could not be separated from IM-A5a by using purification techniques like chromatography. Attempts to purify the crude product by crystallization failed and in all cases oily mixtures were obtained. Additional investigations had to be done in order to increase the selectivity of the ozonolysis reaction in which the cleavage of the 7,8-double bond in compounds like IM-A5 is significantly suppressed.

Thus, a further problem underlying the present invention was to provide a process allowing the increase of the selectivity of the ozonolysis reaction. This problem has been solved by using specific protecting groups $R_2$ for the selective preparation of the compounds of the formula IM-A5.

Influence of Protecting Groups $R_2$ for Selective Preparation of IM-A5 Derivatives:

Generally protection of the hydroxyl group in compounds of formula IM-A3 can be done in a common manner as known to those skilled in the art, Thus, e.g. acylation can be carried out by using an appropriately activated carboxylic acid such as the corresponding anhydrides or halides. For instance, benzoylation of IM-A3a resulting in the formation of IM-A4b is carried out by using benzoylchloride and applying the same conditions as used for the preparation of IM-A4a (Scheme 18).

Scheme 18:

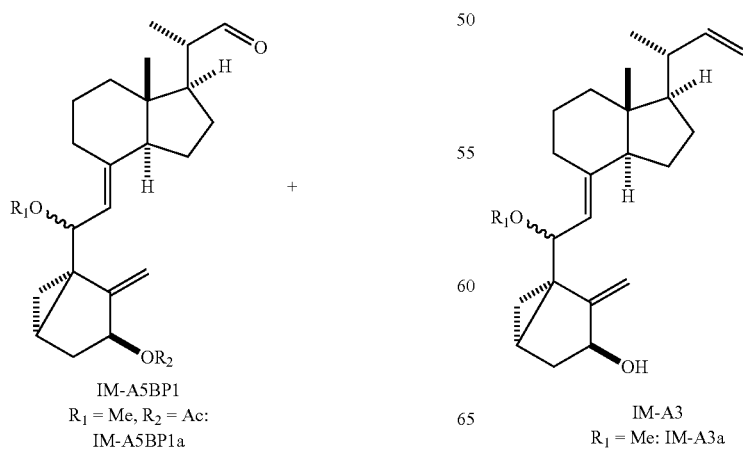

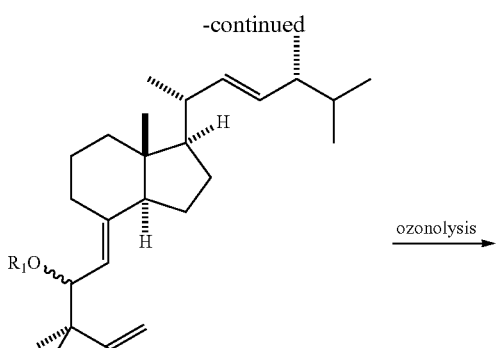

IM-A4
R₁ = Me, R₂ = Bz: IM-A4b
R₁ = Me, R₂ = BOM: IM-A4c
R₁ = Me, R₂ = TES: IM-A4d
R₁ = Me, R₂ = TBS: IM-A4e:

ozonolysis

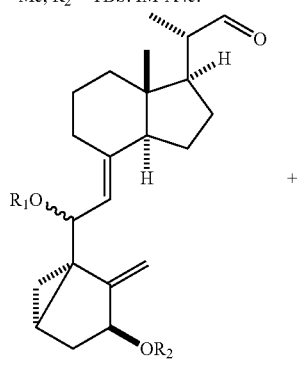

IM-A5BP1
R₁ = Me, R₂ = Bz: IM-A5BP1b
R₁ = Me, R₂ = BOM: IM-A5BP1c
R₁ = Me, R₂ = TES: IM-A5BP1d
R₁ = Me, R₂ = TBS: IM-A5BP1e:

+

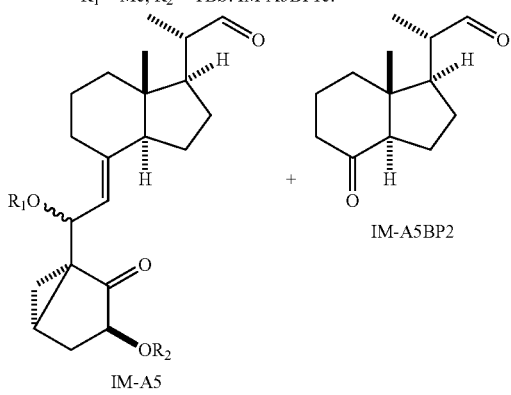

IM-A5BP2

IM-A5
R₁ = Me, R₂ = Bz: IM-A5b
R₁ = Me, R₂ = BOM: IM-A5c
R₁ = Me, R₂ = TES: IM-A5d
R₁ = Me, R₂ = TBS: IM-A5e:

IM-A4c is prepared from IM-A3a by using 1.5 eq. BOMCl in the presence of 2.5 eq. diisopropylethylamine carried out in methylene chloride as solvent at a temperature ranging from 0° C. to room temperature. After an almost complete conversion (>90%), the solvent is removed by evaporation and the residue is taken up in aqueous sodium bicarbonate solution and extracted with MTBE. Drying of the organic layer with magnesium sulfate followed by filtration and evaporation yields crude IM-A5c which is obtained as colorless oil after purification by column chromatography.

Silylation of IM-A3a yielding IM-A4d is carried out in methylene chloride by using 1.25 eq. of TESCl in the presence of 2.0 eq. triethylamine. The product is isolated by an extractive method from the reaction mixture as performed for IM-A4c. The isolated crude product is used directly for the next step (ozonolysis).

IM-A4e is prepared from IM-A3a by using 1.1 eq. to 1.5 eq. TBSCl in the presence of 2.0 eq. imidazole carried out in methylene chloride as solvent at a temperature ranging from 0° C. to 10° C. After an almost complete conversion (>90%), aqueous sodium bisulfate solution is added, the phases are separated and the organic layer is extracted with aq. sodium bicarbonate solution. The organic layer is dried with magnesium sulfate and concentrated in vacuo to dryness. Purification of the residue by column chromatography gives IM-A4e initially as colorless oil.

Generally the protected IM-A4a-e derivatives are obtained as oils from the reaction mixtures after work up, each consisting of the 6R*-diastereomer (major product) and the 6S*-diastereomer (minor product). The diastereomeric mixtures are already formed during the cyclovitamin formation in step 2 (Scheme 16). Investigation of crystallization procedures showed that in contrast to IM-A4a-d, IM-A4e can be surprisingly crystallized as single diastereomer (6R* derivative, Scheme 19) from a mixture consisting of methanol and/or ethanol and MTBE.

Scheme 19:

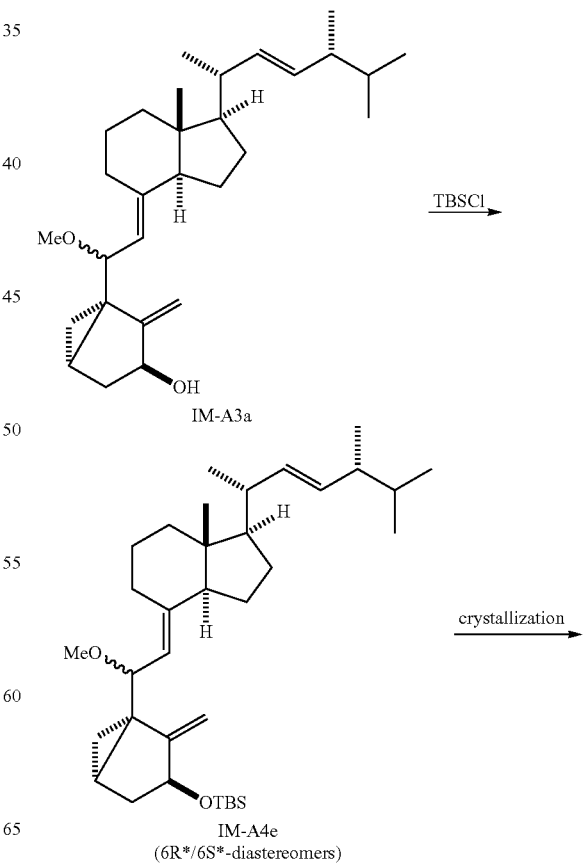

IM-A3a

TBSCl crystallization

IM-A4e
(6R*/6S*-diastereomers)

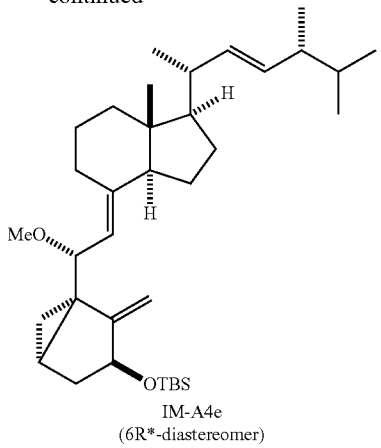

IM-A4e
(6R*-diastereomer)

Single crystal measurement of IM-A4e confirms the presence of the 6R*-diastereomer (FIG. 7). It should be generally noted that both the pure 6R*-diastereomer as well as the 6S*/6R*-diastereomeric mixture of IM-A4e can be used as intermediates for the preparation of paricalcitol (see FIG. 3-10). Furthermore, it will be apparent to those skilled in the art that such 6S*/6R*-diastereomeric mixtures may be separated by common techniques like column chromatography or HPLC on each step where they are present during the course of the preparation of paricalcitol according to the routes as depicted in FIG. 3-10.

Investigations of the ozonolysis of compounds of formulas IMA4b-e (Scheme 18) gives surprising results. Thus in case of compounds IM-A4b and IMA-4c, the same difficulties occur as in the ozonolysis of IM-4a and large amounts of the impurity IM-A5BP2 are formed before the conversion to IM-A5b or IMA5c is complete.

In contrast thereto, the ozonolysis of the silylated compounds IM-A4d and IM-A4e surprisingly proceeds selectively to IM-A5d and IM-A5e without significant formation of IM-A5BP2. After isolation and purification, IM-A5d and IM-A5e are obtained in yields up to 79%.

Thus in a preferred embodiment for the preparation of compounds of formula IM-A4 which are highly useful intermediates for the preparation of paricalcitol, the 1α-hydroxyl group in IM-A3 is protected as silyl ether giving IM-A4 wherein $R_2$ is selected from —Si($R_3$)($R_4$)($R_5$), and wherein $R_3$, $R_4$ and $R_5$ are independently $C_1$-$C_4$ alkyl groups or phenyl groups such as trimethylsilyl (TMS), triethylsilyl (TES), triisopropylsilyl (TIPS), dimethylisopropylsilyl (IPDMS), isobutyldimethylsilyl, tert-butyldimethylsilyl (TBS or TBDMS), tert-butyldiphenylsilyl (TBDPS) and the like. Preferred silyl groups are triethylsilyl, triisopropylsilyl and tert-butyldimethylsilyl and most preferred is tert-butyldimethylsilyl.

Formation of the silyl ethers may be done according to the methods as described above or by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0).

In general, the silylation may be carried out in organic solvents or mixture of solvents such as acetonitrile, ethers, esters, halogenated hydrocarbons (e.g. methylene chloride), aromatic solvents (e.g. toluene), polar aprotic solvents (e.g. DMF, NMP) with a silylating reagent and in the presence of a base. Preferred organic solvents include acetonitrile, THF and methylene chloride with methylene chloride being most preferred.

As silylating reagent may be used the corresponding silyl chlorides, silyl triflates, HMDS, BSU or the like but the corresponding silyl chlorides are preferred.

The amount of silylating reagent may range from about 1.0 eq. to about 2.0 eq. and the use of about 1.1 eq. to about 1.5 eq. is preferred. Fewer equivalents give an incomplete conversion while higher amounts are generally redundant.

As bases may be used preferably tertiary organic amines like triethylamine, diisopropylethyl amine, DABCO, pyridine, imidazole, 2,5-lutidine and most preferably imidazole. The base should be used in at least equimolar amounts calculated on the amounts of the silylating reagent. An excess of at least 1.5 eq. is preferred. It should be noted that a deficit of base based on the amount of the silylating reagent may not trap the acid formed during the reaction.

If e.g. silyl chlorides are used then a deficit of the base may not trap completely the liberated HCl and decomposition of the product may take place due to its acid sensitivity as described above.

The reaction is typically carried out at a temperature range from 0° C. to room temperature, preferably from 0° C. to 15° C.

After completion of the reaction (monitored by TLC), the reaction may be worked up in a manner known in the art. Typically, aqueous 1M sodium bisulfate solution is added to the reaction mixture, and then the product is extracted from the aqueous mixture by using water-immiscible solvents in which the products are sufficiently soluble, e.g., methylene chloride, MTBE or ethyl acetate. The combined extracts are backwashed with aqueous alkaline solution, preferably sodium bicarbonate solution, followed by drying with magnesium sulfate and evaporation of the organic solvent. The residue may be purified by column chromatography or by (re-)crystallization. Thus in case of IM-A4e the residue (crude IM-A4a) is dissolved in an ether, preferably MTBE, and an alcohol, preferably ethanol, is added slowly to the solution in order to crystallize IM-A4e as single 6R*-diastereomer. The amount of ether added to the residue (crude IM-A4e) is about 2/3 (v/w, ratio volume of MTBE to weight of residue obtained after the work up procedure) up to at least equal amounts (v/w). The amount of alcohol added to the ether solution corresponds to about 8 fold (v/v) up to about 12 fold amount (v/v) compared to the amount of ether used for dissolution of the crude IM-A4e. The addition of the solvents is conveniently done at a temperature ranging from room temperature to 50° C. The alcohol is added for a time period ranging from 0.5 h to at least 2 h. After addition of the alcohol, the suspension is stirred at a temperature from −10° C. to 0° C. for a time period ranging from about 1 h to about 15 h before being filtered. The product is then employed for the next step (ozonolysis).

Aspects for Work Up Procedures of Reaction Mixtures Obtained after Ozonolysis

Generally, it is well known that depending on the work up procedure of the ozonolysis reaction mixture, different products may be obtained (see e.g. M. B. Smith, J. March, *March's Advanced Organic Chemistry, Reactions, Mechanisms, and Structure*, 5th edition, 2001, John Wiley & Sons, Inc., ISBN 0-471-58589-0). Thus a reductive treatment of the ozonolysis reaction mixture gives either alcohols (e.g. by addition of sodium borohydride) or aldehydes/ketones (e.g. by addition of $Ph_3P$ or $Me_2S$), while oxidative work up leads to carboxylic acids and/or ketones depending of the groups attached to the alkene carbons.

The preferred embodiment of this invention includes a reductive treatment of the ozonolysis reaction mixture in order to isolate compounds of formula IM-A5 (procedure A) or of formula IM-B6 (procedure B) as shown in Scheme 20, wherein $R_1$ and $R_2$ are as defined above. Both compounds are suitable intermediates for the preparation of paricalcitol (see also description below as well as FIG. 3-8). IM-A5 obtained by procedure A may be reduced in an additional step to IM-B6 by using hydride reducing agents. Such reduction is generally known to those skilled in the art. Both carbonyl groups (C(10)-keto group and C(22)-aldehyde group) in IM-A5 may be reduced independently but a simultaneous reduction of the C(10)-keto group and C(22)-aldehyde group is preferred.

Thus in a preferred embodiment of the invention, the ozonolysis of compounds of formula IM-A4, wherein $R_2$ is a silyl protecting group, is carried out by using a standard ozone generator and oxygen as starting gas in amounts, and at a temperature, and for a period of time, that are effective for producing compounds of formula IM-A5 by using procedure A or compounds of formula IM-A6 by using procedure B (Scheme 20).

The ozone is passed through a solution of silylated IM-A4 carried out in those solvents which are inert to oxidation by ozone.

Scheme 20:

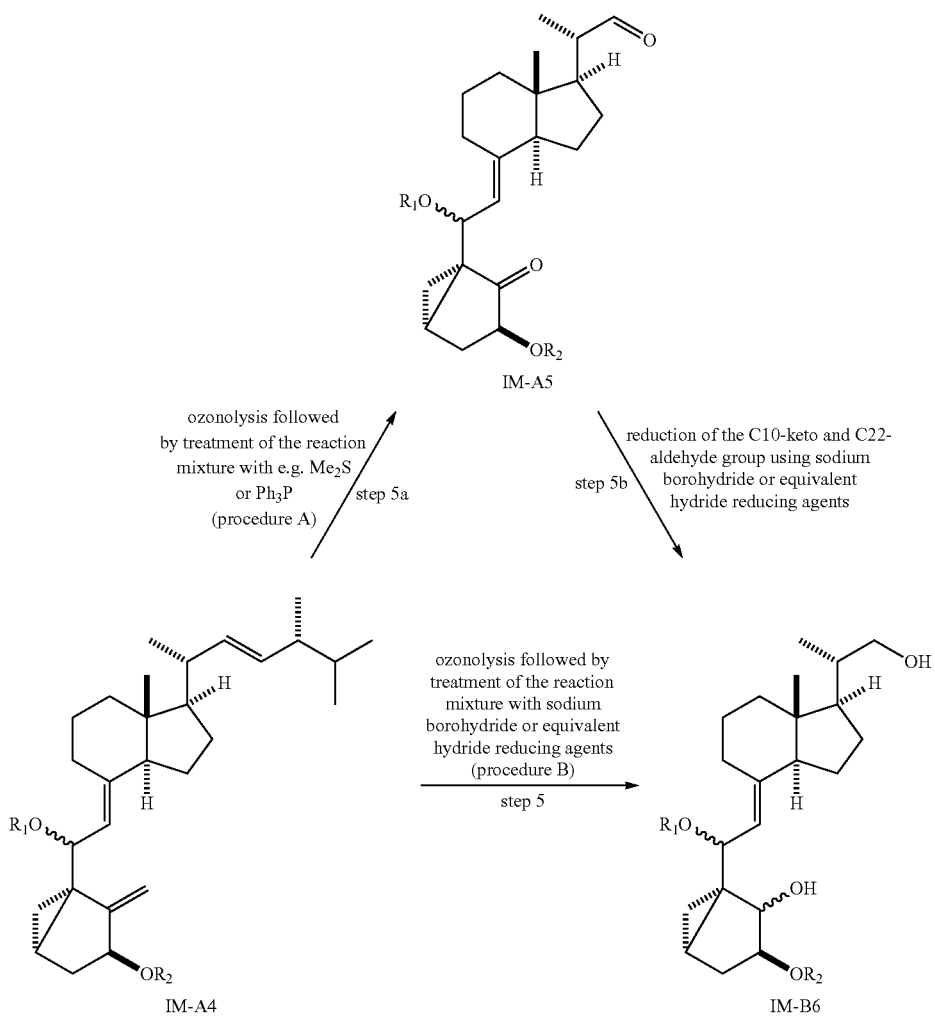

In cases wherein IM-B6 is used as intermediate for the preparation of paricalcitol (routes B1, B2, C1 and C2), the reductive work up procedure B (hydride reduction) of the ozonolysis reaction mixture by using reagents such as sodium borohydride, lithium aluminium hydride or any other equivalent hydride reducing agent is preferred. Latter procedure has the advantage, that two chemical transformation (ozonolysis and hydride reduction) can be carried out as "one pot process" (step 5) without the need for an independent preparation and isolation of IM-A5 (step 5a) followed by an additional reducing step to IM-B6 (step 5b).

Preferably the solvent is selected from halogenated hydrocarbons, such as methylene chloride, $C_1$-$C_4$ alcohols or mixtures thereof, with methylene chloride being the most preferred solvent.

The ozonolysis is conveniently carried out in the presence of a suitable base. Preferred are organic bases, for example, pyridine, triethylamine, quinoline with pyridine being the most preferred base. About 1.0 eq. to about 3.0 eq. of the base may be used (based on the amount of IM-A4), preferred is the use of about 2.0 eq.

The ozonolysis is typically carried out at a temperature range from −80° C. to −40° C., preferably at temperatures from −80° C. to −60° C. The amount of ozone employed for the reaction is sufficient to give an almost complete conversion (>90%) which can be monitored by TLC or HPLC.

Upon completion, the reaction mixture is purged with nitrogen and worked up under reductive conditions according to procedure A for isolating compounds of formula IM-A5 or according to procedure B for isolating compounds of formula IM-B6.

In procedure A, the ozonolysis reaction mixture is typically quenched with about 2 eq. to about 3 eq. dimethyl sulfide or triphenylphosphine at a temperature ranging from −60 to −50° C. The reaction mixture is allowed to warm up to room temperature and poured into an aqueous 0.5 M sodium bisulfate solution. Isolation, e.g. by extraction, and purification of the product by column chromatography can be done according to methods which are generally known to those skilled in the art.

The isolated product IM-A5 can be then reduced in a suitable solvent yielding IM-B6, e.g., by using sodium borohydride or any other equivalent of hydride reducing agent.

Suitable organic solvents include ethers, alcohols, halogenated hydrocarbons and the like.

If stronger reducing agents then sodium borohydride are used then protic solvents like alcohols or solvents like esters should be avoided. The reduction is conveniently carried out at temperatures from 0° C. to room temperature, preferably at room temperature. The amount of the reducing agent is at least sufficient to reduce both carbonyl groups. After an almost complete conversion (>90%) is obtained, the reaction mixture can be worked up in a manner known in the art. For instance, excess hydride reducing agent may be quenched by addition of acetone first optionally followed by removal of the organic solvent by evaporation, before water or aqueous sodium bicarbonate solution is added. The product can be then extracted from the aqueous mixture by using water-immiscible solvents like MTBE, ethyl acetate or methylene chloride. Purification of crude IM-B6 can be done, e.g., by standard techniques like column chromatography.

Alternatively, IM-B6 can be obtained directly from the ozonolysis reaction mixture by using procedure B. Thus after completion of the ozonolysis and purging with nitrogen, the reaction mixture is treated with sodium hydride or an equivalent hydride reducing agent. Preferably sodium borohydride is added to the reaction mixture, and in cases wherein the ozonolysis is carried out in methylene chloride, additionally an alcohol preferably ethanol may be added. The addition of sodium borohydride and dilution of the mixture with ethanol can be done directly to the cold ozonolysis mixture, which is then allowed to warm up to room temperature. Quenching of the hydride reaction mixture and its work up in order to isolate IM-B6 can be done in the same manner as previously described.

It should be generally noted that in cases wherein other protecting groups than silyl groups are chosen for $R_2$, then the reaction conditions and especially the kind of reducing agents have to be adapted. For instance, if the ozonolysis starting material IM-A4 contains reduction labile groups (e.g. esters; $R_2$=acyl group), then only such selective reducing conditions and hydride reducing agents should be employed for the treatment of the ozonolysis reaction mixture which result in the formation of IM-B6 without affecting any protection group.

(2) Synthesis of paricalcitol via intermediates IM-A5 or IM-B6 (routes A1, B1, B2, C1 and C2)

In the following description, methods for the preparation of paricalcitol starting from intermediates IM-A5 or IM-B6 are provided. One of the key steps is the installation of the paricalcitol side chain in compounds like IM-A5, IM-B11 and IM-C10 (see. FIG. 3-10) by applying the side chain synthons as depicted in Scheme 13. It should be noted that for the formation of the 22,23 double bond, a mixture of E- and Z-isomers may be obtained. For instance, the installation of the side chain via Wittig reaction or Julia olefination in compounds like IM-A5, IM-B11 or IM-C10 may result in a mixture of E- and Z-isomers (see e.g. P. R. Blakemore, *J. Chem. Soc., Perkin Trans. I*, 2002, 2563-2585) depending of the kind of solvents, bases and reaction conditions. Persons skilled in the art will be able to separate the desired E-isomer from the undesired Z-isomer by common techniques such as column chromatography, HPLC and/or fractional crystallization.

Figure 3:
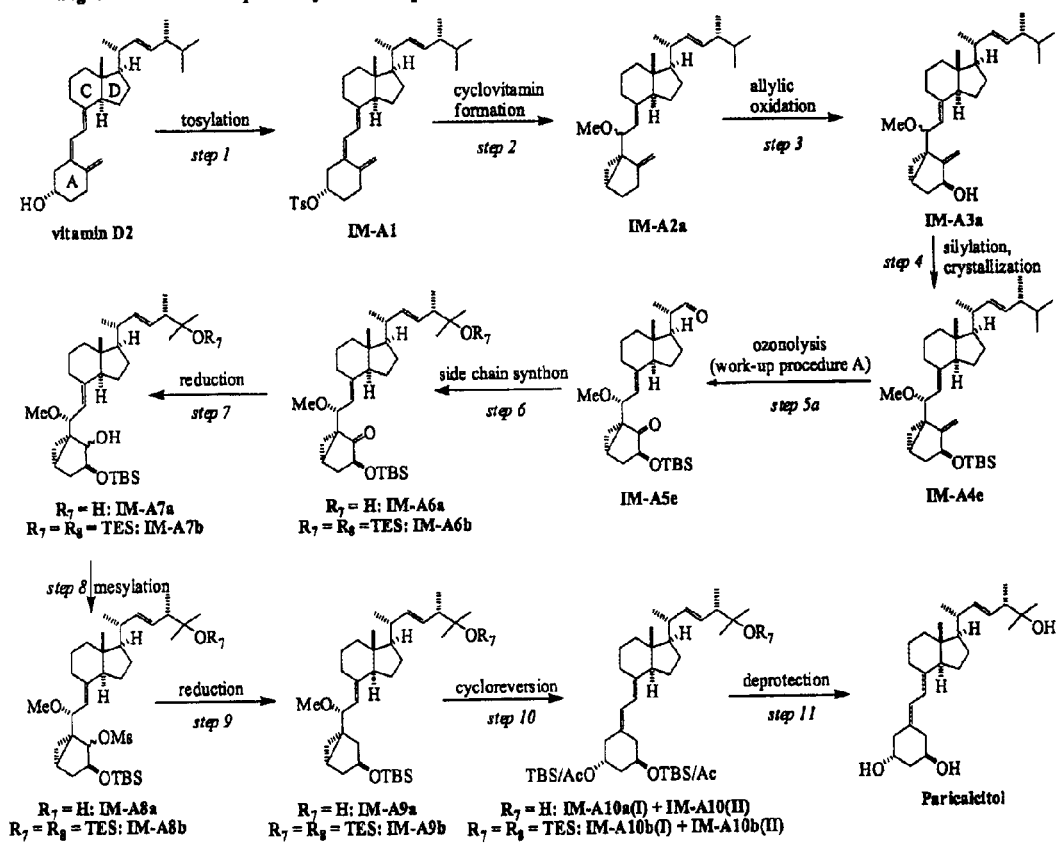
FIG. 3 is a flow chart showing a detailed example for the synthesis of paricalcitol according to route A1.

(3a) Synthesis of Paricalcitol According to Route A1 (FIGS. 3 and 4)

Step 6: Generally, as described above, the installation of the protected or unprotected paricalcitol side chain in compounds of formula IM-A5e (Scheme 21) may be done by using side chain synthons as depicted in scheme 13.

Scheme 21:

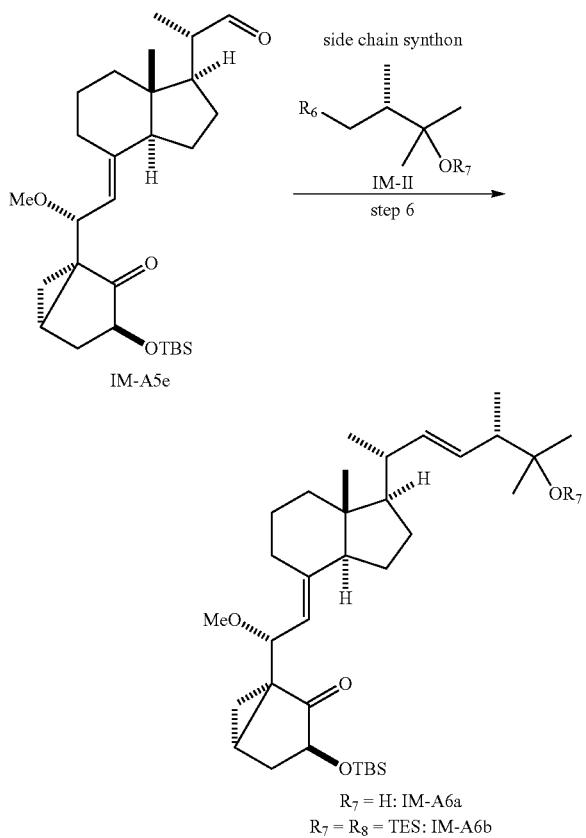

Unfortunately, attempts to prepare IM-A6a by applying the Wittig reagent IM-WR5 for the installation of the side chain in IM-A5e failed, and only decomposition was observed even after varying the reaction conditions. In contrast, if the modified Julia reagent IM-JR6a was used then compound IM-A6b could be successfully prepared.

In an exemplary procedure, 0.7 eq. of IM-JR6a was treated in DME at −60° C. with 1.1 eq. KHMDS. To this mixture was added IM-A5e at −48° C. and stirring was continued at −20° C., monitored by in-process control using TLC. After extractive work up of the reaction mixture, the isolated crude material was purified by column chromatography.

Thus in a general aspect of the invention, the installation of the paricalcitol side chain (Scheme 22, FIG. 2) is carried out in a suitable organic solvent by treatment of compounds of formula IM-A5 with reagents selected from IM-JR6, preferably IM-JR6a, in amounts, and at a temperature and for a period of time, that are effective for producing compounds of formula IM-A6 wherein $R_1$, $R_2$, $R_7$ and $R_8$ are as defined above. The side chain synthons are first deprotonated by using a suitable base before the reaction with IM-A5 is performed.

Scheme 22:

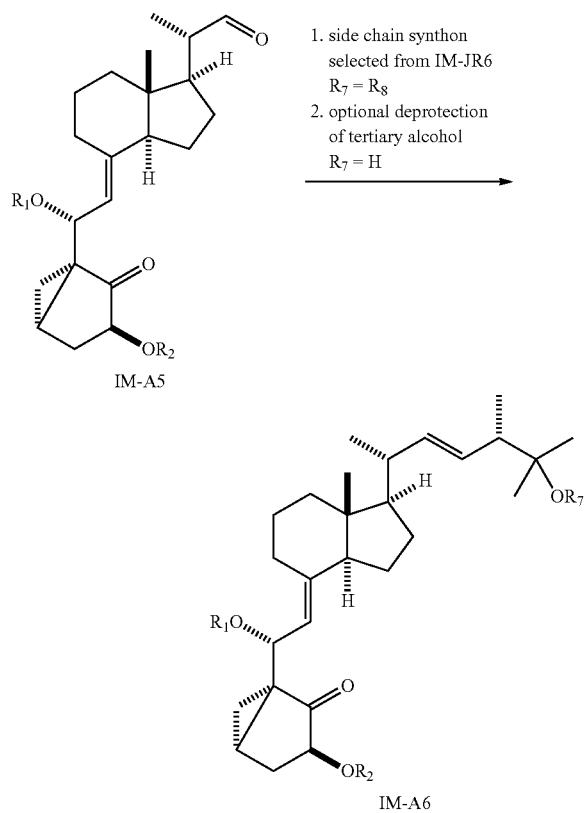

IM-A5

1. side chain synthon selected from IM-JR6 $R_7 = R_8$
2. optional deprotection of tertiary alcohol $R_7 = H$

IM-A6

Suitable organic solvents are such solvents which are compatible with the reaction conditions used for installing the side chain into compounds of formula IM-5A.

Such solvents may be selected from aromatic solvents like toluene or from ethers such as diethyl ether, THF, 2-methyl-THF, DME and dioxane or mixture of aromatic solvents and ethers. Preferred organic solvents are ethers and DME is most preferred.

Suitable bases for deprotonation of IM-JR6 are LDA, aryl or alkyl lithium, or alkali metal hexamethyldisilazane, preferably alkali metal hexamethyldisilazane with potassium hexamethyldisilazane being most preferred.

About 0.6 eq. to at least 2.0 eq. of the side chain synthons IM-JR6 can be used and about 0.6 eq. to about 1.5 eq. are preferred (calculated on the amounts of IM-A5). The deprotonation of the side chain may be carried out at a temperature range from −80° C. to −20° C., preferably from −60° C. to −20° C. by using about 0.9 eq. to about 1.1 eq., preferably about 1.0 eq. of the base (calculated on IM-JR6). After about 1 h reaction time IM-A5 is added and the mixture is stirred at a temperature ranging from about −50° C. to about −10° C. preferably from about −40° C. to about −10° C.

Steps 7 to 11: Compounds of formula IM-A6 may be converted to paricalcitol according to the methods as provided in EP 0387077. The reactions may be also carried out in a similar manner as described by K. L. Perlman et al., Tetrahedron Letters, 31, 1823-1824 or as described herein for routes B and C (see below). Exemplary conversions starting with IM-6a are shown in FIG. 3, Persons skilled in the art will recognize that the protection groups $R_2$ and $R_8$ are still variably and may be independently cleaved on any steps during the course of the synthesis of paricalcitol according to route A (FIG. 3). It should be noted that deprotection of $R_2$ should be done after deoxygenation of the C(10)-keto group in order to avoid side reaction at the free 1α-hydroxyl group during the conversion of the C(10)-keto-group to the corresponding methylene group. Protection group $R_1$ is generally removed during the cycloreversion of the cyclovitamin compound.

Figure 5:
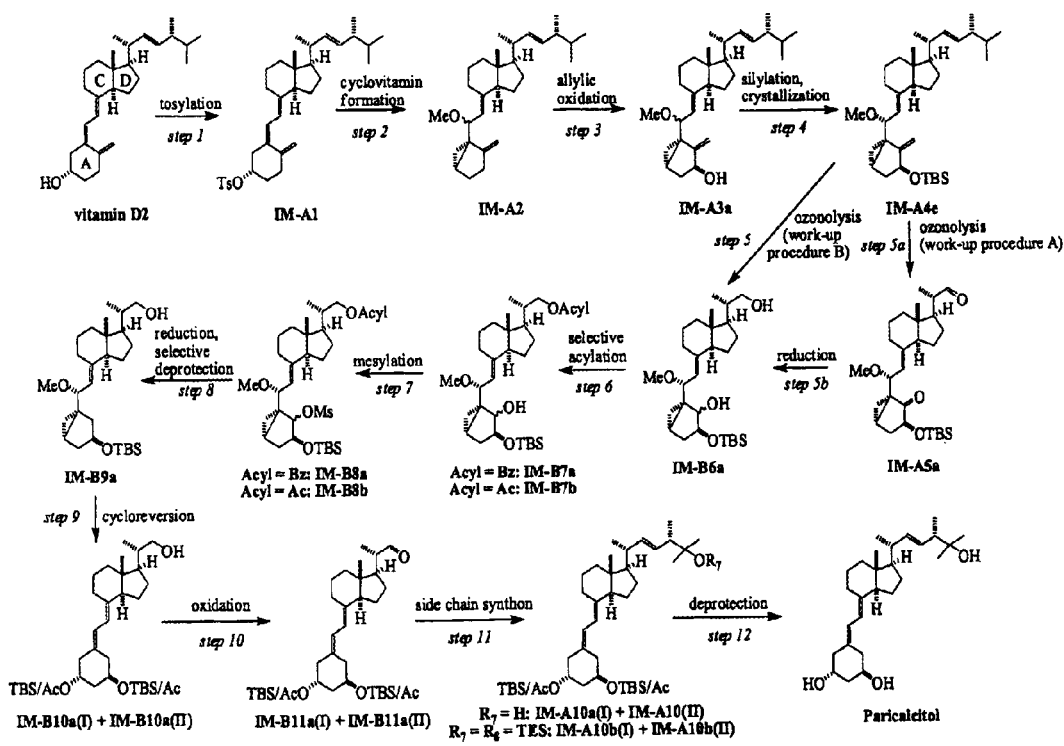
FIG. 5 is a flow chart showing a detailed example for the synthesis of paricalcitol according to route B1.

(3b) Synthesis of Paricalcitol According to Routes B1 and B2 (FIGS. 5 to 7)

Step 6: In an exemplary embodiment of the invention, the primary hydroxyl group in IM-B6a is selectively acylated by employing benzoyl chloride or, alternatively, acetyl chloride yielding IM-B7a or IM-B7b (Scheme 23). Thus to a solution of IM-B6a in methylene chloride containing 3 eq. pyridine is added dropwise 1.2 eq. to 1.5 eq. of the corresponding carboxylic acid chloride at a temperature ranging between 0° C. and <10° C. After an in-process control (TLC) shows a complete conversion, water is added and stirring is continued for approximately 1 h at the same temperature range. The phases are separated, the aqueous layer extracted with methylene chloride and the combined organic phases are washed with aqueous sodium bicarbonate solution and optionally with saturated aqueous sodium chloride solution. After drying with magnesium sulfate, the solvent of the organic layer is evaporated leaving a crude product (IM-B7a or IM-B7b) which is used directly for the next step.

Scheme 23:

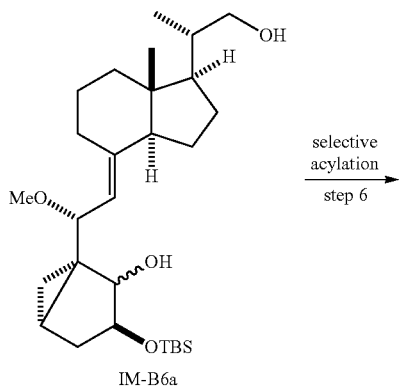

IM-B6a selective acylation
step 6

-continued

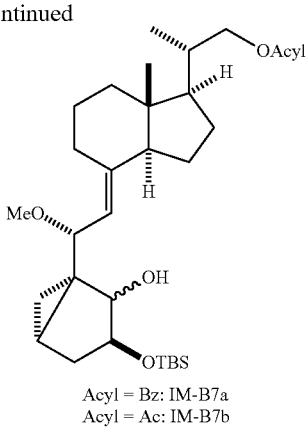

Acyl = Bz: IM-B7a
Acyl = Ac: IM-B7b

In a general aspect of the invention, compounds of formula IM-B6 are selectively protected resulting in the formation of compounds of formula IM-B7 (Scheme 24). The protection of the hydroxyl group is necessary to avoid side reaction (e.g. simultaneous reduction) during the deoxygenation of the C(10) hydroxy group in steps 7 and 8 (see below).

Scheme 24:

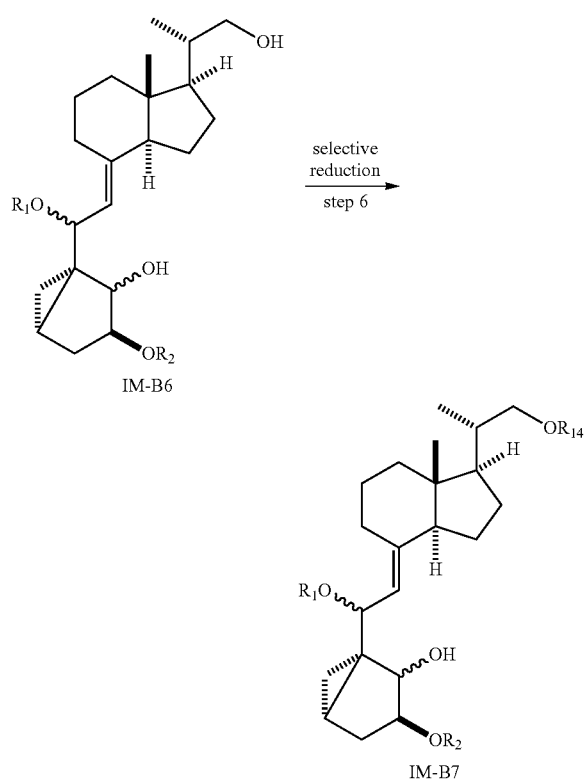

Generally, selective protection of the primary hydroxyl group ($R_{14}$) in presence of a secondary hydroxyl groups may be obtained by applying methods known in the art or it may be investigated experimentally by those skilled in the art. Suitable protecting groups may be selected from those as described by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0).

Preferred protecting groups $R_{14}$ are such groups, which are orthogonal to $R_1$ and $R_2$, which are stable under conditions used for sulfonylation (step 7) and which can be selectively cleaved under neutral or alkaline conditions which includes reductive or oxidative methods.

The orthogonal protecting group $R_{14}$ can be selectively cleaved in step 8 while $R_1$ and $R_2$ are not affected. The advantage of the use of orthogonal protecting groups for the primary hydroxyl group is that during its oxidation to the aldehyde in step 11 of route B as well as in step 9 of route C the other hydroxyl groups remains protected and they will be not affected during the oxidation. Since the compound in step 8 (IM-B8) consists of the acid labile cyclovitamin structure, the selective deprotection of $R_{14}$ has to be carried out in neutral or alkaline medium by employing hydrolytic methods, reductive methods as used for hydride reductions, oxidative methods or by using other non-acidic deprotection agents. A person skilled in the art will be able to select carefully the groups $R_1$, $R_2$ and $R_{14}$ with respect to their orthogonality on the basis of published data. For instance, the relative stabilities of the different silyl groups are described by P. G. M. Wuts and T. W. Greene in *Greene's Protective Groups in Organic Synthesis*, fourth edition 2007, published by John Wiley & Sons, Inc., Hoboken, N.J. (ISBN-13: 978-0-471-69754-1, ISBN-10: 0-471-69754-0).

Therefore in a particular embodiment, the primary hydroxyl group in IM-B7 is selectively protected by using protections groups selected from those groups which can be cleaved under neutral or alkaline conditions by using hydrolytic, reductive (hydride reduction) or oxidative methods or any other non-acidic deprotection agents. More particular the protection group can be removed simultaneously under such reductive conditions (hydride reduction) which are used in step 8 for the deoxygenation avoiding an additional step for its separate deprotection.

Preferred protecting groups are selected from those groups which can be selective cleaved in the presence of $R_1$ and $R_2$ such as substituted or unsubstituted acyl groups like formyl, acetyl, chloroacetyl, dichloroacetyl, trichloroacetyl, methoxyacetyl or benzoyl, $C_1$-$C_2$ trialkylsilyl groups such as trimethylsilyl, triethylsilyl, or (alkoxy)(alkyl)(aryl)silyl such as tert.-butylmethoxyphenylsilyl, more preferred are substituted or unsubstituted acyl groups and most preferred is acetyl or benzoyl.

The acylation can be carried out by using standard acylation procedures, such as treatment of IM-B6 with an appropriately activated carboxylic acid such as acyl anhydride or acyl halide in the presence of a suitable base such as pyridine, in amounts, and at a temperature and for a period of time, that are effective for producing compounds of formula IM-B7, wherein $R_1$, $R_2$ and $R_{14}$ are defined as described above. The use of stronger bases (pKa≥12) may give a decrease of the selectivity during the acylation. About 1.1 eq. to about 2.0 eq. of the activated carboxylic acid may be used, preferred are about 1.2 eq. to about 2.0 eq. The reaction may be carried out in the presence of about 2.0 eq. to about 5.0 eq. of a base with about 3.0 eq. to about 4.0 eq. being preferred. Fewer equivalents of the base may not efficiently trap the liberated acid (e.g. HCl from acyl chlorides) causing decomposition of the acid-sensitive product while higher amounts are not necessary. The reaction may be carried out at a temperature range between about −20° C. and about 50° C., preferred is a temperature between about −5° C. and about room temperature. Lower temperatures may prolong the reaction time, while higher temperatures may decrease the selectivity of the acylation.

Steps 7 to 8: IM-B7a is reacted with methanesulfonic acid chloride in methylene chloride and in presence of triethylamine, similarly to the procedure described in EP0387077. Determination of the products formed during the reaction showed that only side reaction took place and IM-8a was not formed even after varying the amounts of methanesulfonic acid chloride and triethylamine. Replacement of triethylamine by pyridine gave no conversion while replacement of methanesulfonic acid chloride by methanesulfonic acid anhydride gave again decomposition. Surprisingly, when the reaction is carried out with methanesulfonic acid anhydride in the presence of pyridine instead of triethylamine, then the desired product (IM-B8a) could be obtained. IM-B8a was then successfully reduced to IM-B9a using lithium aluminium hydride (Scheme 25). Under this condition, the carboxylic ester was simultaneously reduced to the primary alcohol.

Thus in an exemplary embodiment of the invention, IM-B7a is first reacted with 2.0 eq. methanesulfonic acid anhydride in methylene chloride as solvent and in the presence of 5 eq. pyridine at a temperature ranging between 0° C. and 10° C. After an in-process control (TLC) showed complete conversion (15 h), aqueous sodium bisulfate solution is added and the phases are separated. The organic layer is washed with aqueous sodium bicarbonate solution, dried with magnesium sulfate and then concentrated to dryness by evaporation under reduced pressure. IM-B8a is then dissolved in diethyl ether and added to 3 eq. of a 1M solution of lithium aluminium hydride at a temperature ranging from 0° C. to 5° C. and maintaining the temperature ≤5° C. during the addition. After an in-process control (TLC) shows complete conversion (15 h), the reaction mixture is worked up in a usual manner and the product is purified by column chromatography.

Compound IM-B7b is converted to IM-B8b in a similar manner as described for IM-B7a but with the exception that methylene chloride is replaced by THF. After complete conversion, the reaction mixture is filtered first before the solvent is removed by evaporation. The reduction of IM-B8b to IM-B9a is performed similarly to the reduction of IM-B8a with the exception that after completion of the reaction, excess aluminum hydride is destroyed by addition of acetone before IM-B9a is isolated and purified by the usual procedure.

Scheme 25:

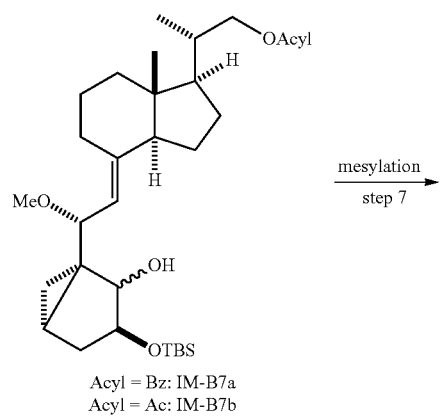

Acyl = Bz: IM-B7a
Acyl = Ac: IM-B7b mesylation
step 7

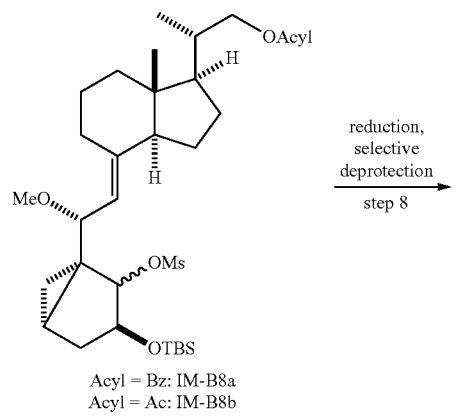

Acyl = Bz: IM-B8a
Acyl = Ac: IM-B8b reduction,
selective
deprotection
step 8

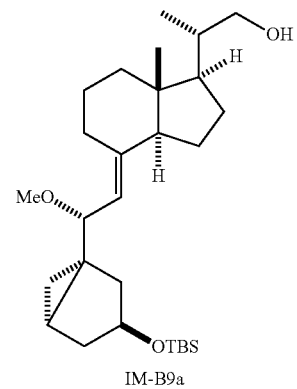

IM-B9a

In a general aspect of the invention, the secondary hydroxyl group in compounds of formula IM-B7 is first converted to an alkyl- or arylsulfonic acid ester, which is then reduced giving compounds of formula IM-B9 (Scheme 26). In cases wherein the protection group ($R_{14}$) is not cleaved during the reduction, it may be removed separately by using methods known to those skilled in the art.

Scheme 26:

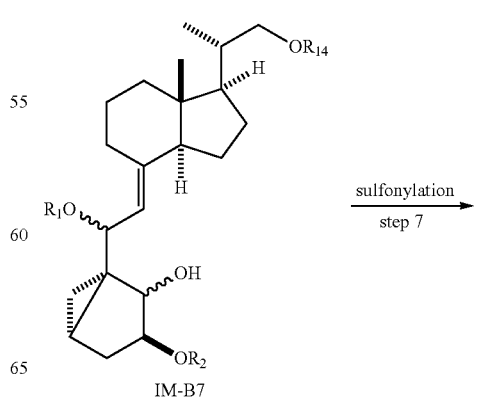

IM-B7 sulfonylation
step 7

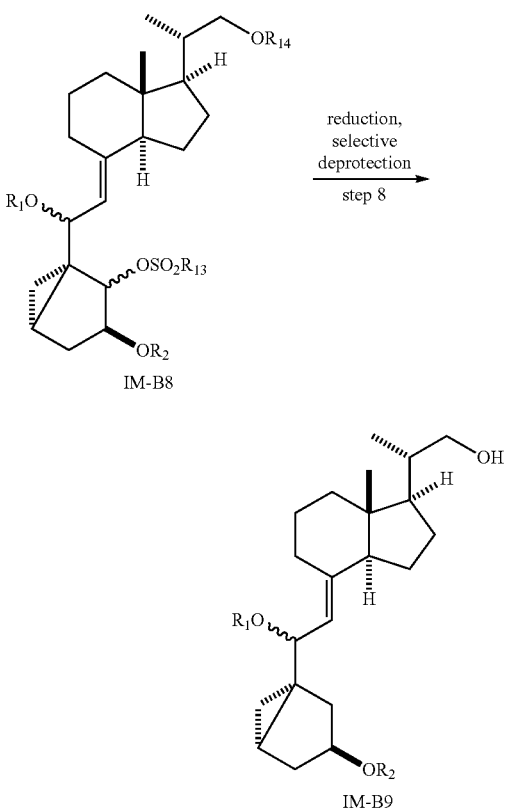

In a particular embodiment IM-B7 is reacted with an alkyl- or arylsulfonic acid anhydride $(R_{13}—SO_2)_2O$ in a suitable inert solvent and in the presence of a suitable base, in amounts, and at a temperature and for a period of time, that are effective for producing compounds of formula IM-B8 wherein $R_1$, $R_2$ and $R_{14}$ are defined as described above and wherein $R_{13}$ is $C_1$-$C_4$-alkyl, phenyl, $C_1$-alkylphenyl, unsubstituted aryl or aryl substituted by a $C_1$-$C_2$ alkyl group or halogen.

Typical alkylsulfonic acid anhydrides, unsubstituted or substituted arylsulfonic acid anhydrides are methanesulfonic acid anhydride, ethanesulfonic acid anhydride, benzylsulfonic acid anhydride, benzenesulfonic acid anhydride, p-toluenesulfonic acid anhydride, 4-chlorobenzenesulfonic acid anhydride, preferably methanesulfonic acid anhydride or p-toluenesulfonic acid anhydride and more preferably methanesulfonic acid anhydride.

The sulfonylation can be carried out with about 1.2 eq. to about 3.0 eq., preferably with about 1.5 eq. to about 2.0 eq. of the sulfonic acid anhydride.

The reaction is performed in the presence of a base preferably selected from tertiary aromatic amines like pyridine, 2-, 3- or 4-picoline or 2,6-lutidine with pyridine being most preferred. The amount of the base may range between about 2.0 eq. and about 3.0 eq. (based on the amount of sulfonic acide anhydride), and is preferably about 2.5 eq. Lower amounts of the base may not sufficiently trap the liberated sulfonic acid, resulting in decomposition of the product, while higher amounts are generally not necessary.

As suitable solvents may be employed halogenated hydrocarbons such as methylene chloride or chloroform, ethers like THF, DME or diethyl ether or mixtures thereof. Preferred solvents are methylene chloride or THF.

The sulfonylation is conveniently carried out at a temperature ranging from 0° C. to room temperature, preferably from 0° C. to 10° C.

After completion of the reaction, the product can be isolated by employing a usual extractive work up procedure as known in the art.

Alternatively, the reaction mixture can be filtered and the isolated crude product after evaporation of the solvent can be directly used for the next step without its isolation by extraction. It should be noted, that the sulfonate esters IM-B8 are difficult to purify by column chromatography during which decomposition may occur.

For the reductive removal of the sulfonate ester, compounds of formula IM-B8 are reacted with suitable reducing reagents in a suitable inert solvent, in amounts, and at a temperature and for a period of time, that are effective for producing compounds of formula IM-B9 wherein $R_1$, $R_2$, $R_{13}$ and $R_{14}$ are defined as described above.

As suitable reducing agents are preferably used lithium aluminium hydride or lithium triethylborohydride with lithium aluminium hydride being more preferred. Preferred inert organic solvent are ethers like THF, diethyl ether or DME, more preferably THF, diethyl ether and most preferably diethyl ether. About 2.5 eq. to about 5.0 eq. eq. of the reducing agent may be used, about 3.0 eq. to about 4.0 eq. of the reducing agent are preferred.

The reaction is typically carried out at a temperature ranging between about 0° C. and about room temperature, preferably ranging between about 0° C. and about 15° C. Lower temperatures may prolong the reaction time while higher temperatures may result in formation of more side products.

After the almost complete conversion (>90%), the excess hydride reducing agent is conveniently destroyed by addition of, e.g., acetone before the mixture is worked up in a normal manner by an extractive method. Evaporation of the solvent after extraction gives a crude product which can be purified by column chromatography.

Step 9: Generally as described in EP0387077 if a 1α-hydroxy-10-deoxy cyclovitamin D intermediate is subjected to solvolysis (cycloreversion) with e.g. acetic acid by using the conditions of Deluca et al. (see reference in this U.S. Pat. No. 4,195,027) then a mixture of corresponding 1α-hydroxy-19-nor-vitamin D 3-acetate and 1α-hydroxy-19-nor-vitamin D 1-acetate is obtained, and the analogous 1- and 3-acylates are produced, when alternative acids are produced. Detailed investigation of possible methods for cycloreversion are described by Gui-Dong Zhu and William H. Okamura, *Chem. Rev.* 1995, 95, 1727-1952.

Thus treatment of compounds of formula IM-B9a with acetic acid gives also a mixture of the two isomeric compounds IM-B10a(I) and IM-B10a(II) (Scheme 27) typically in a ratio of 3:1 to 4:1.

71

Scheme 27:

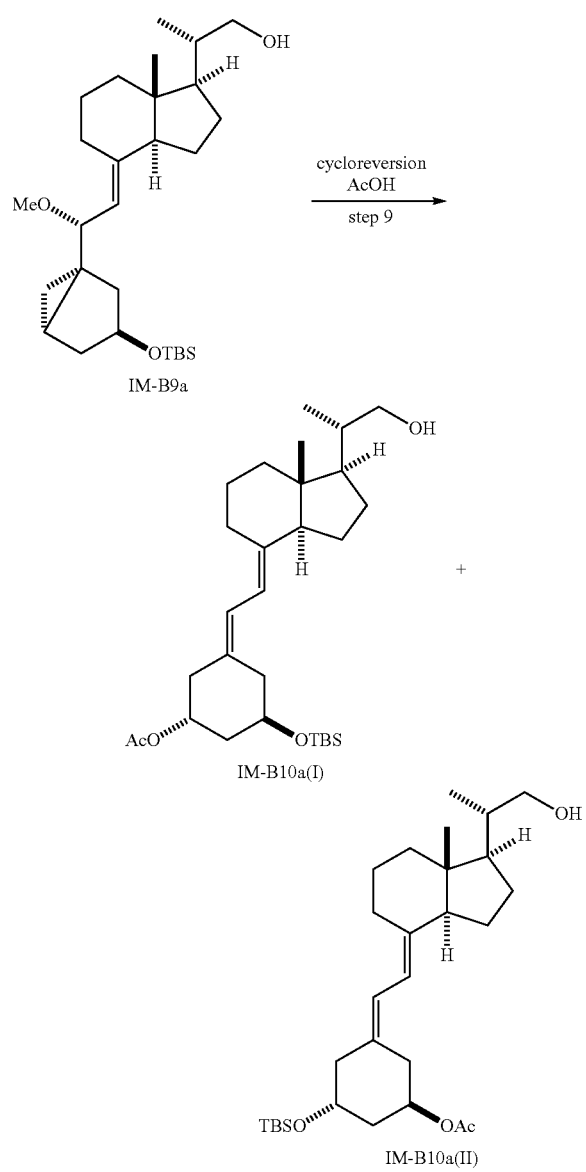

In a typical procedure, IM-B9a is heated in acetic acid at 55° C. yielding a mixture of compounds IM-B10a(I) and IM-B10a(II). After completion of the reaction, the reaction mixture is diluted with water and the work up is continued by extraction of the products from the aqueous layer with MTBE. The organic layer is washed subsequently with water and sodium bicarbonate solution and concentrated in vacuo. Traces of acetic acid can be removed by dissolving the residue in MTBE followed by washing with aqueous (5%) sodium carbonate. Alternatively, the first organic layer may be washed with aqueous 2M sodium hydroxide solution in order to remove acetic acid avoiding the second extraction step (see also preparation of IM-A10a(I) and IM-A10a(II) obtained from IM-C11 below). Drying of the organic layer with magnesium sulfate and removal of the solvent from the organic layer after filtration gives a mixture of IM-B10a(I) and IM-B10a(II) which can be used directly for the next step.

It should be noted that by carrying out the cycloreversion in a mixture of acetic acid and DMSO, then the corresponding

72 alcohols (H instead of Ac in compounds of formula IM-B10a (I) and IM-B10a(II)) may be obtained (see U.S. Pat. No. 4,555,364)).

Scheme 28:

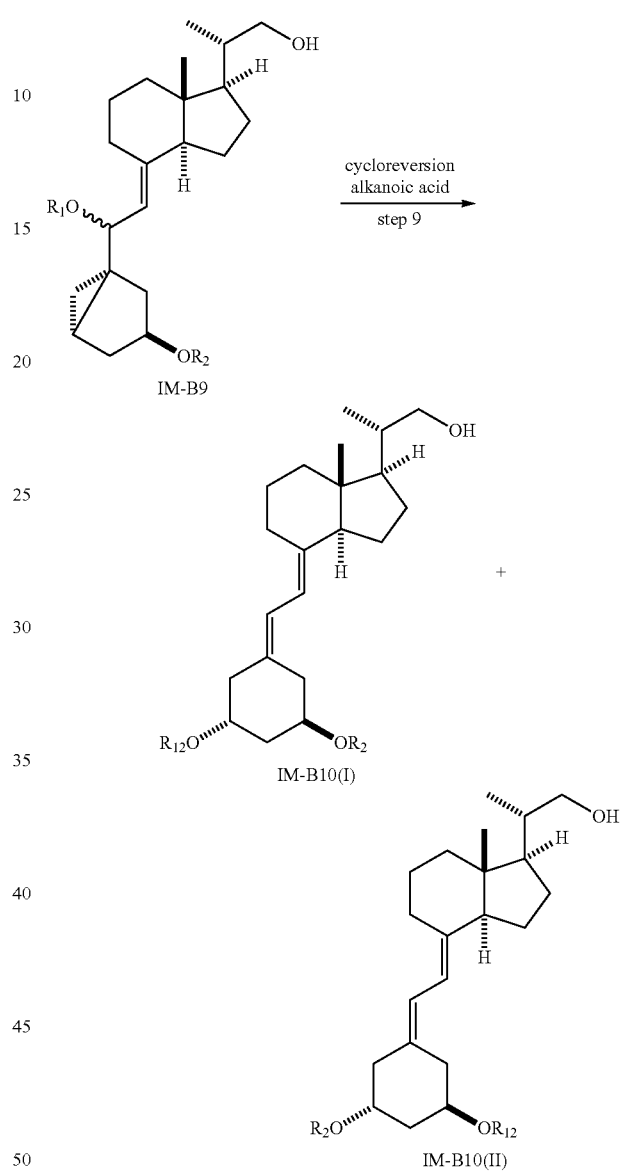

In a particular embodiment IM-B9 is reacted with an $C_1$-$C_4$ alkanoic acid, in amounts, and at a temperature and for a period of time, that are effective for producing compounds of formula IM-B10(I) and IM-B10(II) wherein $R_1$ and $R_2$ are defined as described above and wherein $R_{12}$ is an acyl group such as formyl (HCO), acetyl ($CH_3CO$), propionyl ($CH_3CH_2CO$) and butyryl ($CH_3CH_2CH_2CO$). Optionally the reaction may be carried out in a mixture of alkanoic acid and DMSO resulting in the formation of compounds of formula IM-B10(I) and IM-B10(II) wherein $R_{12}$ is H.

Typical alkanoic acids include $C_1$-$C_4$ alkanoic acids such as formic acid, acetic acid, propionic acid and butyric acid, preferred are formic acid and acetic acid and most preferred is acetic acid. The amount of the alkanoic acid may range from about 5 mL/g IM-B9 to about 20 mL/g IM-B9, and is preferably about 10 mL/g IM-B9 to about 15 mL/g IM-B9. The reaction temperature may range between about 40° C. and about 70° C., preferably between about 50° C. and 60° C. After completion of the reaction, water is added and the products are extracted with a water immiscible solvent such as MTBE. The organic layer is washed with an aqueous inorganic base solution such as an aqueous sodium carbonate solution or aqueous 2M sodium hydroxide solution in order to remove excess alkanoic acid. It will be apparent to those skilled in the art, that higher concentrated aqueous sodium hydroxide solution for the washing steps should be avoided due to the possible saponification of the ester functions in the products. After evaporation of the solvent from the organic layer, a mixture of compounds IM-B10(I) and IM-B10(II) remains which can be used directly for the next step or purified by column chromatography. The latter may be also useful for separation of the isomers, if desired.

Step 10:

A variety of methods are available for selective oxidation of primary alcohols to aldehydes (see e.g. M. B. Smith, J. March, *March's Advanced Organic Chemistry, Reactions, Mechanisms, and Structure*, 5$^{th}$ edition, 2001, John Wiley & Sons, Inc., ISBN 0-471-58589-0). Generally, typical oxidation methods includes:

chromium based oxidations applying e.g. pyridinium chlorochromate (Corey's reagent) or $CrO_3$/pyridine/$CH_2Cl_2$ (Collin's reagent);

hypervalent organoiodane based oxidations (e.g. Dess-Martin periodinane);

DMSO or DMS based oxidations (e.g. DMSO/oxalylchloride (Swern), DMSO/DCC (Pfitzer-Moffat), DMSO/$SO_3$/pyridine (Parikh-Doering), DMSO/NCS (Corey Kim)).

Many other reagents or combination of reagents have been reported to be suitable for oxidation of primary alcohols to aldehydes such as N-tert-butylbenzenesulfinimidoyl, NCS/N-tert-butylbenzenesulfenamide, $NaIO_4$/TEMPO/NaBr, tetrapropylammonium perruthenate/TEMPO or as described in Handbook of Reagents for Organic Synthesis, *Oxidizing and Reducing Agents*, John Wiley & Sons, LTD, 1999, ISBN 0-471-97926-0.

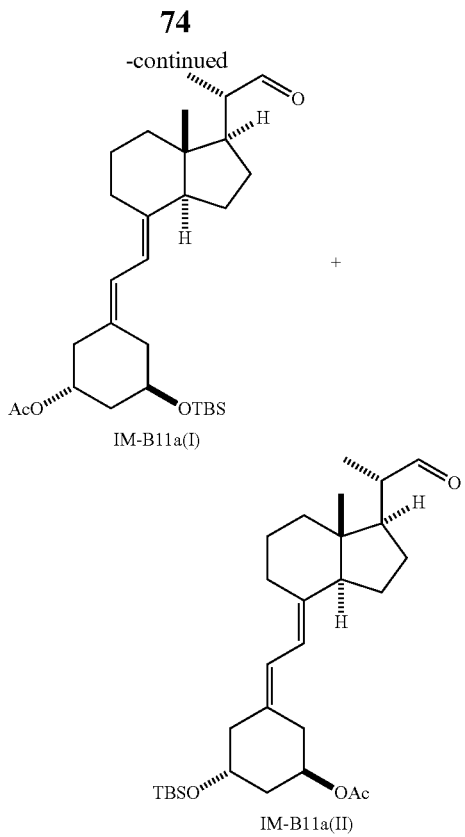

IM-B11a(I)

IM-B11a(II)

In a typical procedure, a mixture of compounds of formula IM-B11a(I) and IM-B11a(II) dissolved in methylene chloride is added to a mixture of DMSO and oxalylchloride at −78° C. After a stirring period of 30 min, triethylamine is added and stirring is continued until an in-process control shows complete conversion. Then aqueous sodium bicarbonate solution and MTBE are added and the phases are separated. The organic layer is washed with water and saturated aqueous sodium chloride solution. The crude material obtained by concentration of the organic layer is purified by column chromatography.

In a general aspect of the embodiment compounds of formula IM-B10 wherein $R_2$ and $R_{12}$ are as described above may be oxidized by using the aforementioned methods (Scheme 30). Persons skilled in the art will be able to select and to carry out an appropriate oxidation method.

Scheme 29:

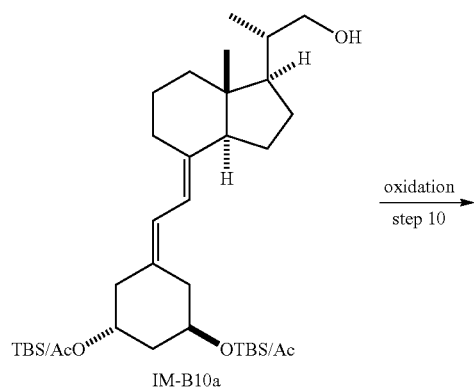

IM-B10a

Scheme 30:

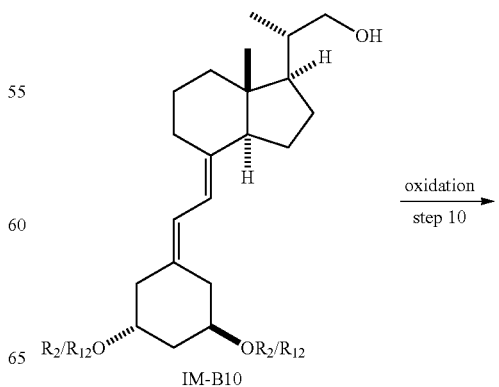

IM-B10

-continued

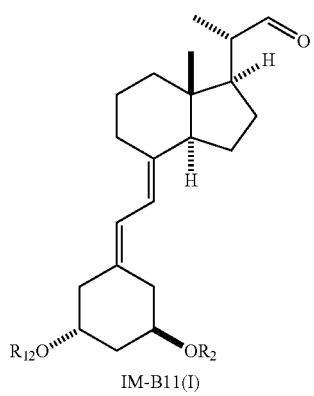

IM-B11(I)

+

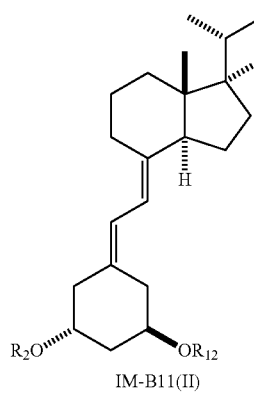

IM-B11(II)

The oxidation may be carried out separately with IM-B10 (I) or IM-B10(II) or with a mixture thereof. The work up procedure for isolation of the products IM-B11(I) and IM-B11(II) can be done in a usual manner. The obtained isomeric mixture can be purified by, e.g., column chromatography. Latter may be also useful for separation of the isomers, if desired.

Step 11: The installation of the protected or unprotected paricalcitol side chain in compounds of formula IM-B11a may be done by using the side chain synthons as depicted in Scheme 13. The isomeric mixture IM-B11a(I) and IM-B11a (II) or a single isomer therefrom may be employed for the reaction with the side chain synthon.

-continued

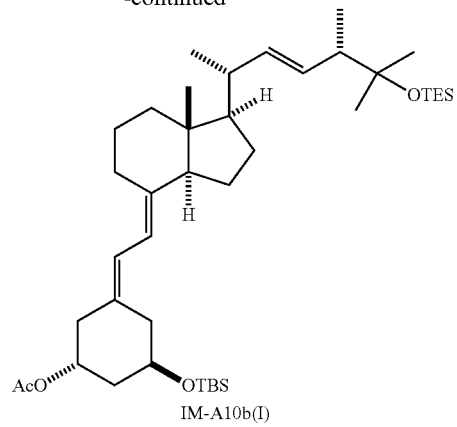

IM-A10b(I)

+

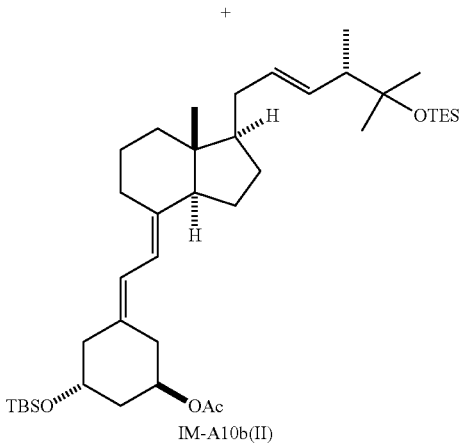

IM-A10b(II)

Thus in a typical experiment (Scheme 31), to a solution of IM-JR6a in DME is added at −25° C. a solution of KHMDS in toluene. After 15 min a solution of IM-B11a(I) and IM-B11a(II) in DME is added keeping the temperature between −20 and −15° C. The reaction mixture is then stirred at −10° C. for 4 h. Afterwards MTBE and aqueous sodium bicarbonate solution is added, the mixture worked-up by an extractive method and the crude product isolated from the organic layer by evaporation of the solvent. The crude product is then purified by column chromatography.

In a particular embodiment IM-B11 or a single isomer therefrom is reacted with a side chain synthons of formula IM-II giving the compounds IM-A10(I) and IM-A10(II) (Scheme 32).

Scheme 31:

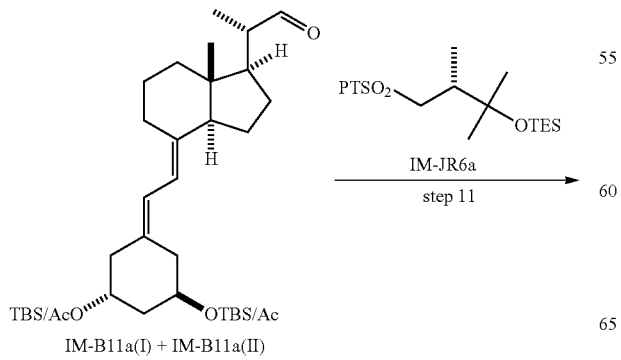

Scheme 32:

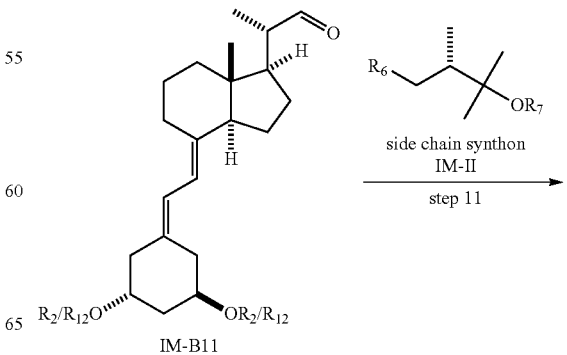

-continued

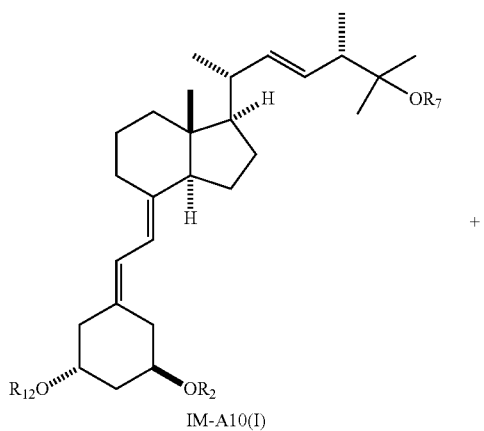

IM-A10(I)

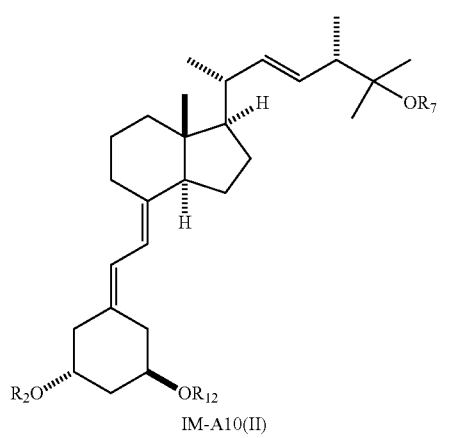

IM-A10(II)

In a preferred embodiment, the side chain synthons IM-II are selected from IM-WR5 and IM-JR6 and in a most preferred embodiment, the side chain synthon is IM-WR5 or IM-JR6a. The reaction is carried out in a suitable solvent by treatment of compounds of formula IM-B11 with the side chain synthons in amounts, and at a temperature and for a period of time, that are effective for producing compounds of formula IM-A10(I), IM-A10(II) or a mixture thereof wherein $R_2$, $R_6$, $R_7$ and $R_{12}$ are defined as described above. The side chain synthons are first deprotonated by using a suitable base before the reaction with IM-B11 is performed.

In case of the Julia olefination using compounds of formula LM-JR6, the reaction is carried out in a similar manner as described above for the reaction with IM-A5.

In case of the Wittig approach using the compound of formula IM-WR5, the reaction may be carried out in a similar manner as described below for the reaction with IM-C10.

Step 12: Compounds of formula IM-A10 are the protected precursors of paricalcitol. Depending of the protection strategy used for the particular route, the hydroxyl groups at C1, C3 and C25 may be protected or non-protected. Since in IM-A10 different protection groups may be present, the strategies for deprotection may be selected from those wherein the particular hydroxyl groups are successively deprotected in separate steps with isolation of the intermediates as exemplary shown in Scheme 33 (route II and route III) or which are carried out as a one pot procedure without isolation of the intermediates (route I). In any case a complete deprotection of compounds of formula IM-A10 (Scheme 34) gives the paricalcitol as the desired final compound. Suitable methods for deprotection are generally known in the art.

Scheme 33:

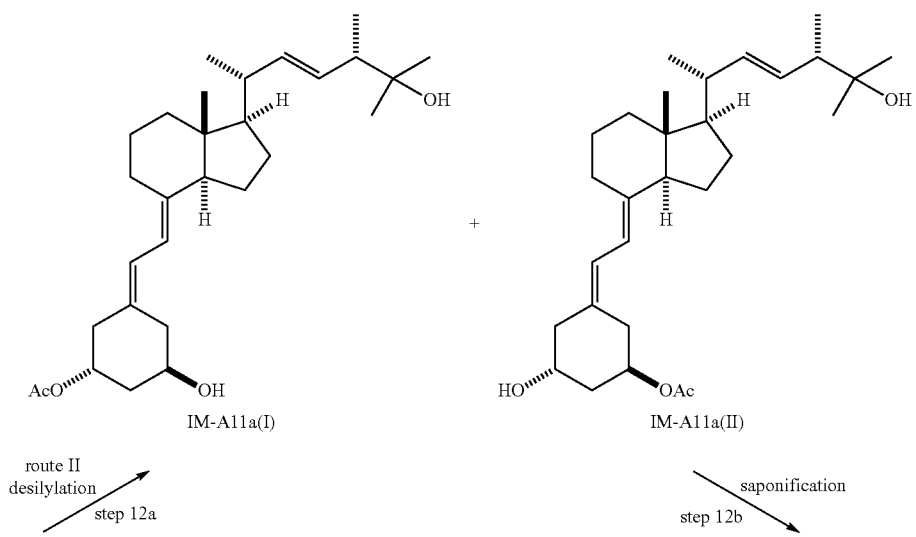

-continued

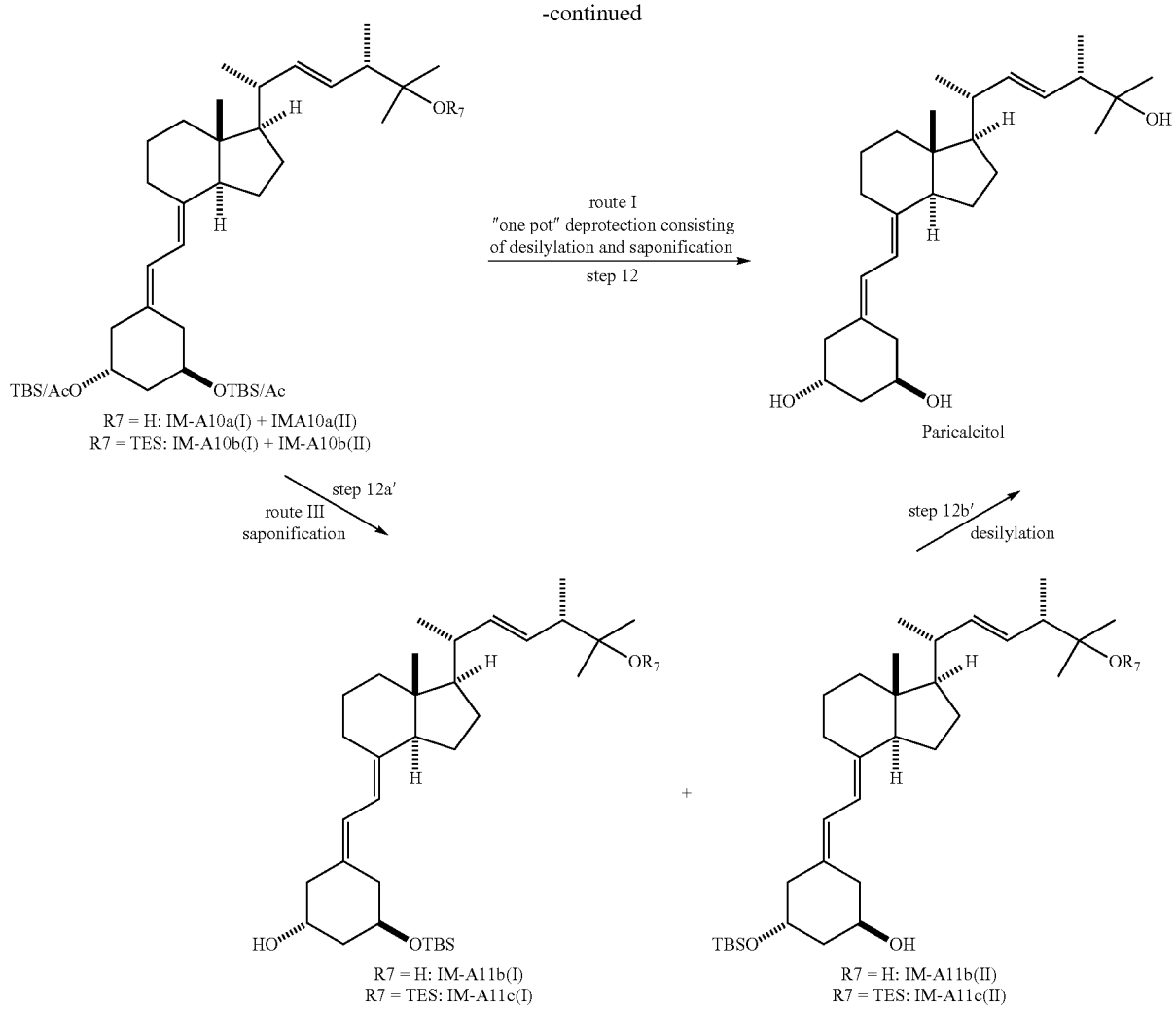

In an exemplary procedure for the deprotection in a one pot procedure (route I in Scheme 33), compounds of formula IM-A10b are first desilylated by treatment with a 1M solution of TBAF in THF at room temperature for 2 h. Dilution of the mixture with methanol followed by addition of an aqueous 2M sodium hydroxide solution causes saponification of the ester groups. After an in-process control shows complete deprotection, aqueous sodium bicarbonate solution and ethyl acetate is added, and the product is isolated by an extractive work up procedure. Concentration of the organic extract solution delivers a crude material which is purified by column chromatography. Further purification is performed by recrystallization from acetone.

In an exemplary procedure for the selective deprotection according to route II (Scheme 33), a mixture compounds of formula IM-A10a(I) and IM-A10a(I) is treated with a 1M solution of TBAF in THF at room temperature for 1.5 h. The reaction mixture is worked-up by an extractive method and the isolated crude material is purified by column chromatography giving a mixture of compounds IM-A11a(I) and IM-A11a(II). This mixture is then dissolved in ethanol and treated with an aqueous 2M sodium hydroxide solution at room temperature (second deprotection step, saponification). After an in-process control shows a complete conversion, the mixture is worked-up by an extractive method. The isolated crude material (paricalcitol) is purified by recrystallization.

Scheme 34:

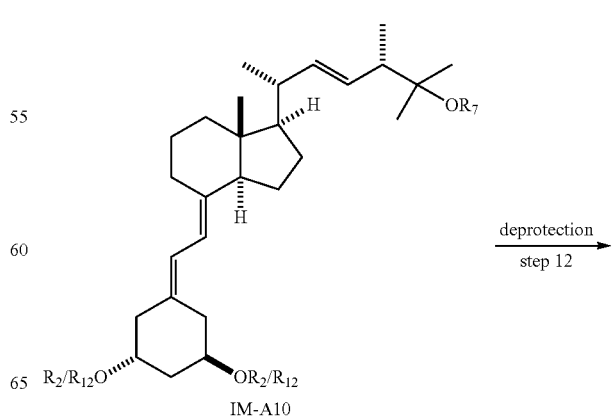

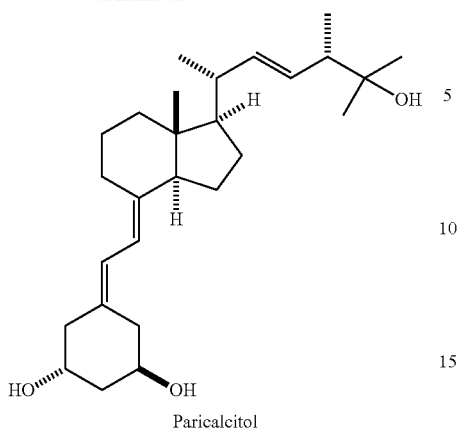

Paricalcitol

Thus in a particular embodiment, compounds of formula IM-A10 wherein $R_2$, $R_7$ and $R_{12}$ are defined as described above are completely deprotected by using methods as known in the art. Such deprotection may be carried out successively with isolation of the respective intermediate which is then further deprotected in separate steps or the complete deprotection is carried as a one pot process. Isomeric intermediates may be separated by methods known in the art (e.g. column chromatography, HPLC) and deprotected separately or subjected as mixtures to deprotection.

Figure 8:
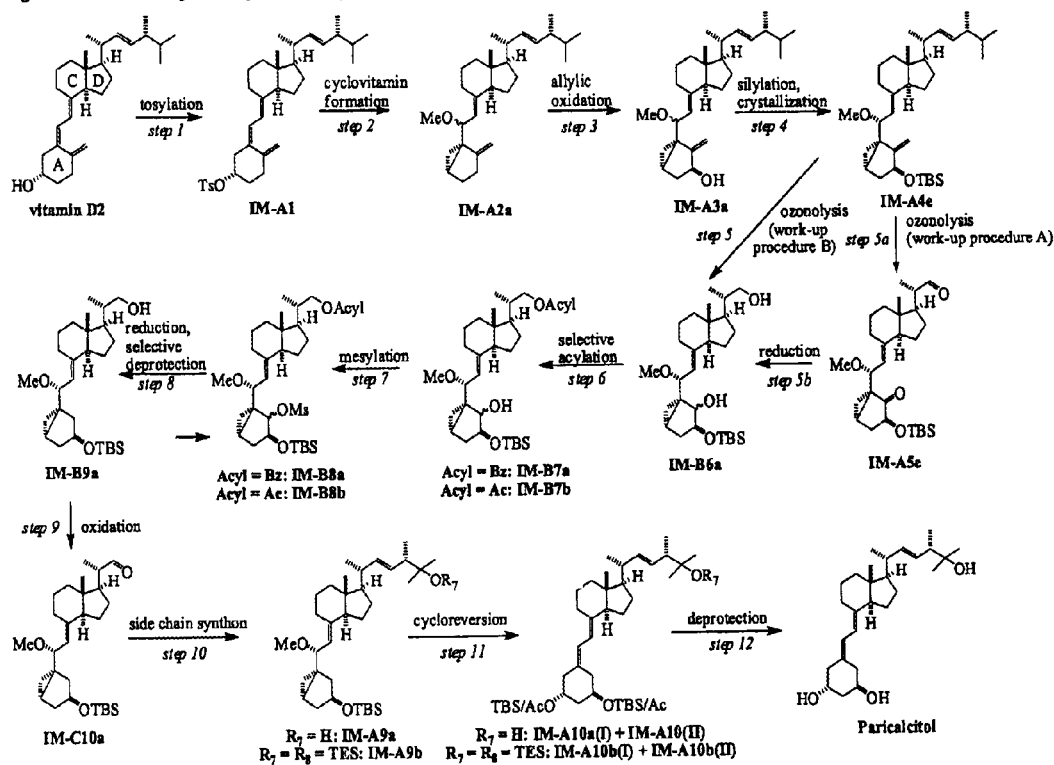
FIG. 8 is a flow chart showing a detailed example for the synthesis of paricalcitol according to route C1.

(3c) Synthesis of Paricalcitol According to Routes C1 and C2 (FIG. 8-10)

Step 9: In an embodiment of the present invention, paricalcitol can be also prepared according to routes C1 and C2 as shown in FIG. 8-10. Routes C1 and C2 start with the oxidation of the primary alcohol in IM-B9a, which is obtained in route B (see above), giving the aldehyde IM-C10a (Scheme 35). In contrast to the oxidation of compounds of formula IM-B10, the oxidation of compounds of formula IM-B9a should be carried out under non-acidic conditions due to its acid-sensitive cyclovitamin structure.

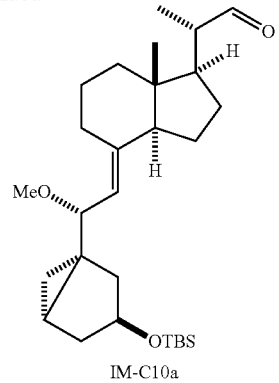

IM-C10a

In a first exemplary procedure (Corey-Kim oxidation), compound IM-B9a is treated with a mixture of NCS, $Me_2S$ and triethylamine in methylene chloride at a temperature ranging from −30° C. to −20° C. After an in-process control shows complete conversion, aqueous sodium bicarbonate solution is added to the reaction mixture, the product isolated by an extractive work up procedure and purified by column chromatography.

In a second exemplary procedure (Dess-Martin oxidation), compound IM-B9a is treated with Dess-Martin periodinane in methylene chloride. The mixture is stirred at room temperature until an in-process control shows complete conversion. Afterwards the reaction mixture is added to a mixture of aqueous sodium bicarbonate solution containing sodium thiosulfate. The product is then isolated by an extractive work up procedure and purified by column chromatography.

In a third exemplary procedure a modified Swern oxidation is used for the preparation of IM-C10 starting from IM-B9a. It can be shown that addition of pyridine prior to the addition of IM-B9a to a mixture consisting of DMSO and oxalylchloride, less side products are formed and a cleaner reaction profile is obtained. Thus to a mixture of DMSO and oxalylchloride in methylene chloride at a temperature ranging between −78° C. and −60° C. is added pyridine followed by addition of a solution of IM-B9a in methylene chloride. Then triethylamine is added and stirring at a temperature ←−50° C. is continued. After an in-process control shows complete conversion, water is added to the reaction mixture, the product isolated by an extractive work up procedure and purified by column chromatography.

Scheme 35:

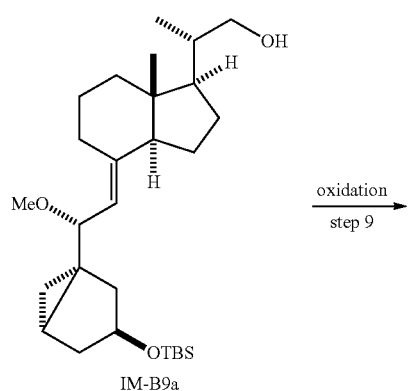

IM-B9a   oxidation step 9 →

Scheme 36:

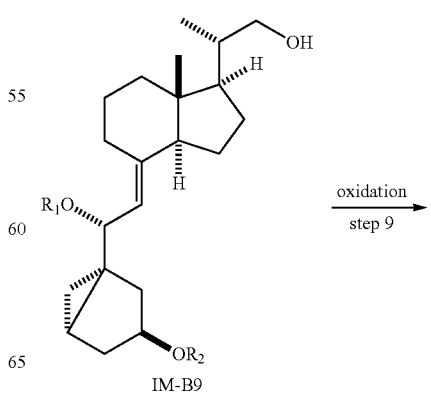

IM-B9   oxidation step 9 →

-continued

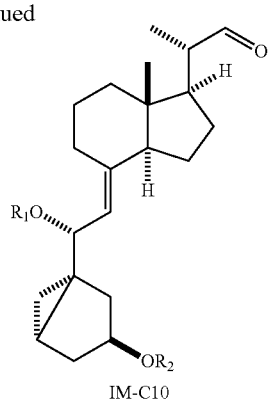

IM-C10

In a particular embodiment IM-B9 is oxidized in a suitable inert organic solvent and under non acidic conditions by using suitable oxidation reagents, in amounts, and at a temperature and for a period of time, that are effective for producing compounds of formula IM-C10 wherein $R_1$ and $R_2$ are defined as described above. Preferred oxidation methods are DMSO or DMS based methods with the methods of Swern oxidation being more preferred, and with the combination DMSO/oxalylchloride being most preferred.

When Swern oxidation is employed, then a slight modification of the standard procedure is preferred, which additionally consists of the addition of a suitable base before compounds of formula IM-B9 are added. Preferred organic solvents include halogenated hydrocarbons with methylene chloride being more preferred. About 2.0 eq. to about 3.0 eq. of DMSO based on the amount of IM-B9 may be used, and about 2.3 eq. to about 2.7. eq. DMSO are preferred. About 0.5 eq. to about 0.7 eq. of oxalylchloride based on the amount of DMSO may be used, about 0.5 eq. to about 0.6 eq. are preferred.

Prior to the addition of IM-B9, a suitable base is added which is preferably selected from tertiary aromatic amines like pyridine, 2-, 3- or 4-picoline or 2,6-lutidine with pyridine being most preferred.

After addition of IM-B9, a second suitable base is added which is preferably selected from tertiary alkyl amines such as trimethyl amine, trimethyl amine or diisoproylethyl amine. It should be noted that stronger bases as the tertiary amines should be avoided since an epimerization of the aldehyde IM-C10 at C20 may occur. The reaction is conveniently carried out at temperatures ranging from about −80° C. to about −40° C. preferably from about −80° C. to about −60° C. After completion of the reaction, water is added and the product is extracted with a water immiscible solvent such as methylene chloride or MTBE. The organic layer is washed with an aqueous inorganic base solution such as an aqueous sodium bicarbonate solution. Evaporation of the solvent from the organic layer delivers compounds of formula IM-C10 which can be purified by standard techniques such as column chromatography.

Step 10: The installation of the protected or unprotected paricalcitol side chain in compounds of formula IM-C10 may be done by using the side chain synthons as depicted in Scheme 13. In this case and in contrast to the side chain installation in compounds of formula IM-A5, the Wittig reaction could be successfully performed with compound IM-C10a (Scheme 37).

Scheme 37:

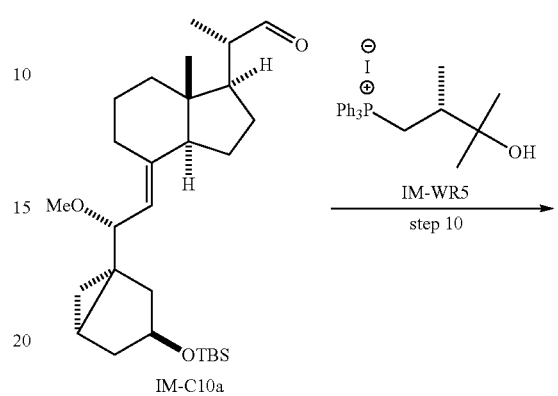

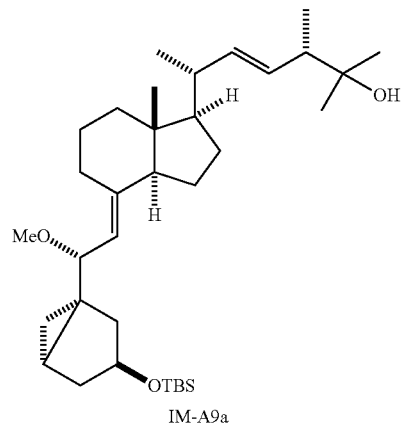

IM-A9a

Unfortunately, it was found that by employing the Wittig reaction of IM-C10a with IM-WR5 in a similar manner as described by J. C. Hanekamp et al., Tetrahedron, 1992, 48, 9283-9294, the presence of small amounts of water caused Cannizzarro-like side reaction with IM-C10a resulting in the formation of IM-B9a and IM-A9BP1 (Scheme 38).

Scheme 38:

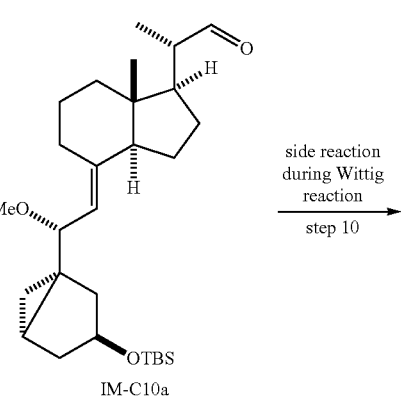

IM-C10a

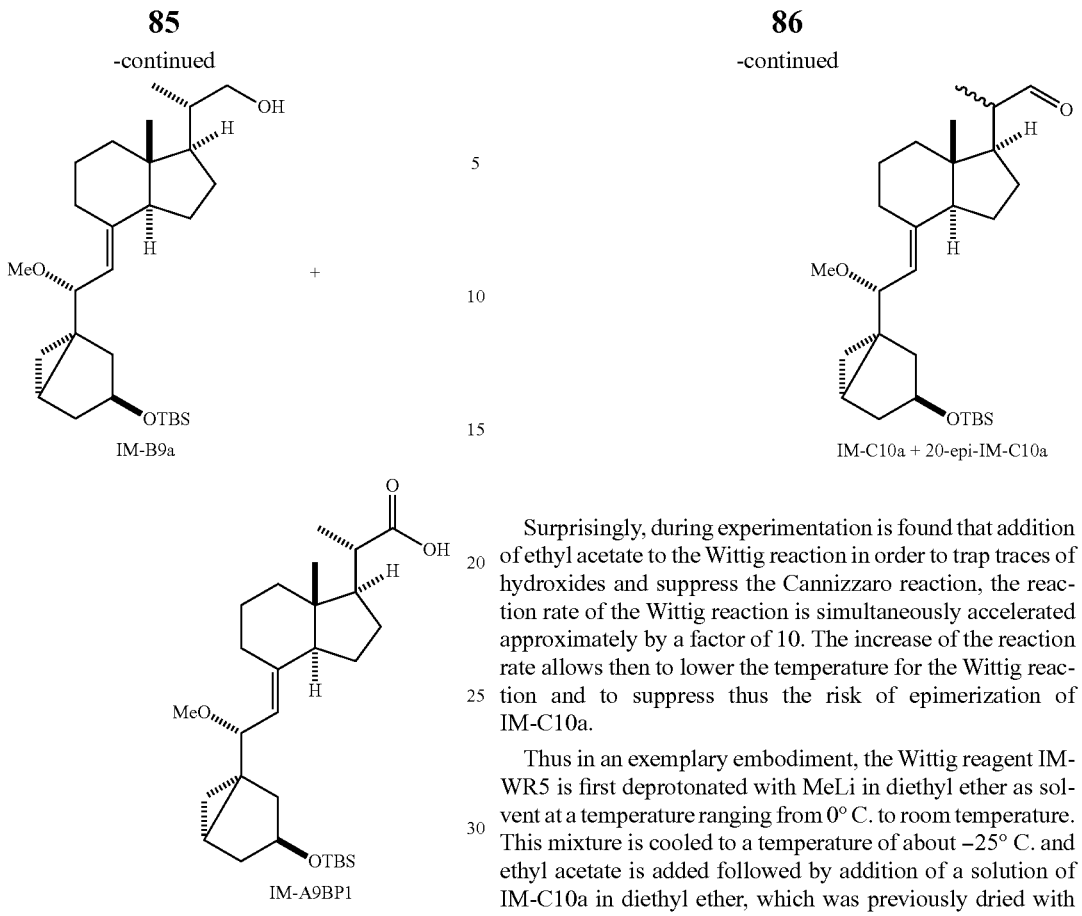

IM-B9a

IM-C10a + 20-epi-IM-C10a

Surprisingly, during experimentation is found that addition of ethyl acetate to the Wittig reaction in order to trap traces of hydroxides and suppress the Cannizzaro reaction, the reaction rate of the Wittig reaction is simultaneously accelerated approximately by a factor of 10. The increase of the reaction rate allows then to lower the temperature for the Wittig reaction and to suppress thus the risk of epimerization of IM-C10a.

Thus in an exemplary embodiment, the Wittig reagent IM-WR5 is first deprotonated with MeLi in diethyl ether as solvent at a temperature ranging from 0° C. to room temperature. This mixture is cooled to a temperature of about −25° C. and ethyl acetate is added followed by addition of a solution of IM-C10a in diethyl ether, which was previously dried with molecular sieve. The reaction mixture was stirred at a temperature ranging between −18° C. and −25° C. until an in-process control showed complete conversion. The reaction mixture is poured into a mixture consisting of aqueous sodium bicarbonate solution and MTBE followed by filtration of the biphasic mixture. The product is isolated by an extractive method and purified by column chromatography.

IM-A9BP1

This side reaction can be suppressed by drying a solution of IM-C10a in diethyl ether with molecular sieve (4A) prior to its employment for the Wittig reaction. Disadvantageously, in contrast to the procedure described by J. C. Hanekamp et al., the Wittig reaction proceeds generally very slow at temperatures of <−10° C. while increasing the temperature to about 0° C. or higher gives significant epimerization at C20 in IM-C10a. Such epimerization is not observed at temperatures of ≤−20° C. (Scheme 39).

Scheme 40:

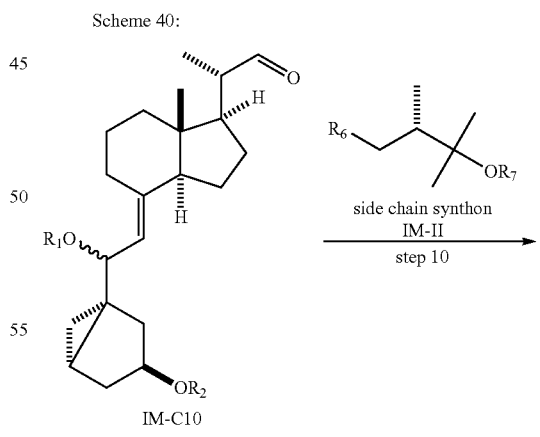

Scheme 39:

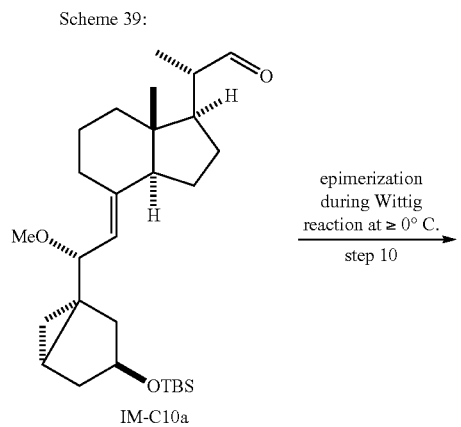

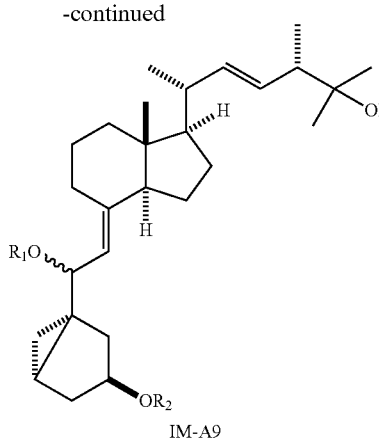

IM-A9

In a preferred embodiment, the side chain synthons are selected from IM-WR5 and IM-JR6 and in a most preferred embodiment, the side chain synthon is IM-WR5 or IM-JR6a. The reaction is carried out in a suitable solvent by treatment of compounds of formula IM-C10 with the side chain synthon in amounts, and at a temperature and for a period of time, that are effective for producing a compound of formula IM-A9 wherein $R_1$, $R_2$ and $R_7$ are defined as described above. The side chain synthons are first deprotonated by using a suitable base before the reaction with IM-C10 is performed.

In case of the Julia olefination by using a compound of formula IM-JR6, the reaction is carried out in a similar manner as described above for the reaction with IM-A5 or IM-B10a.

In case of the Wittig approach using compounds of formula IM-WR5, the reaction is typically carried out in a ether as solvent, preferably THF or diethyl ether and more preferably in diethyl ether. The deprotonation of a compound of formula IM-WR5, giving the corresponding ylide, is carried out first by using the methods and bases as described by J. C. Hanekamp et al., Tetrahedron, 1992, 48, 9283-9294. About 1.1 eq. to about 2.5 eq. of IM-WR5 based on the amount of IM-C10 may be used, and an amount of IM-WR5 ranging between about 1.2 eq. and 1.8 eq. is preferred.

The ylide mixture is then cooled to a temperature ranging between about −10° C. and about −40° C., preferably between about −15° C. and about −25° C., before a carboxylic acid ester is added. Preferred carboxylic acid esters are $C_2$-$C_4$-carboxylic acid $C_1$-$C_2$-ester such as methyl acetate, methyl propionate, methyl acetate or ethyl acetate with methyl acetate or ethyl acetate being more preferred. The amount of the ester ranges between about 2.0 eq. and at least 4.0 eq. based on the amount of IM-WR5, and preferably the amount of the ester ranges between about 2.5 eq. and about 3.5 eq.

Preferably, the solution of IM-C10 in diethyl ether is first dried over a suitable drying agent, before addition to the ylide reaction mixture. The drying agent is selected from those agents, which removes water from the reagent solution but which does not takes part at the Wittig reaction. This drying agent is preferably molecular sieve. The Wittig reaction is carried out at a temperature ranging from −10° C. to −40° C., preferably from −15° C. to −25° C. After completion of the reaction, the product is isolated and purified by using common procedures.

Step 11: The cycloreversion of IM-A9a by treatment with acetic acid can be preformed in a similar manner, as described for IM-B9a resulting in a mixture consisting of the two isomeric compounds IM-A10a(I) and IM-A10a(II) (Scheme 41).

Scheme 41:

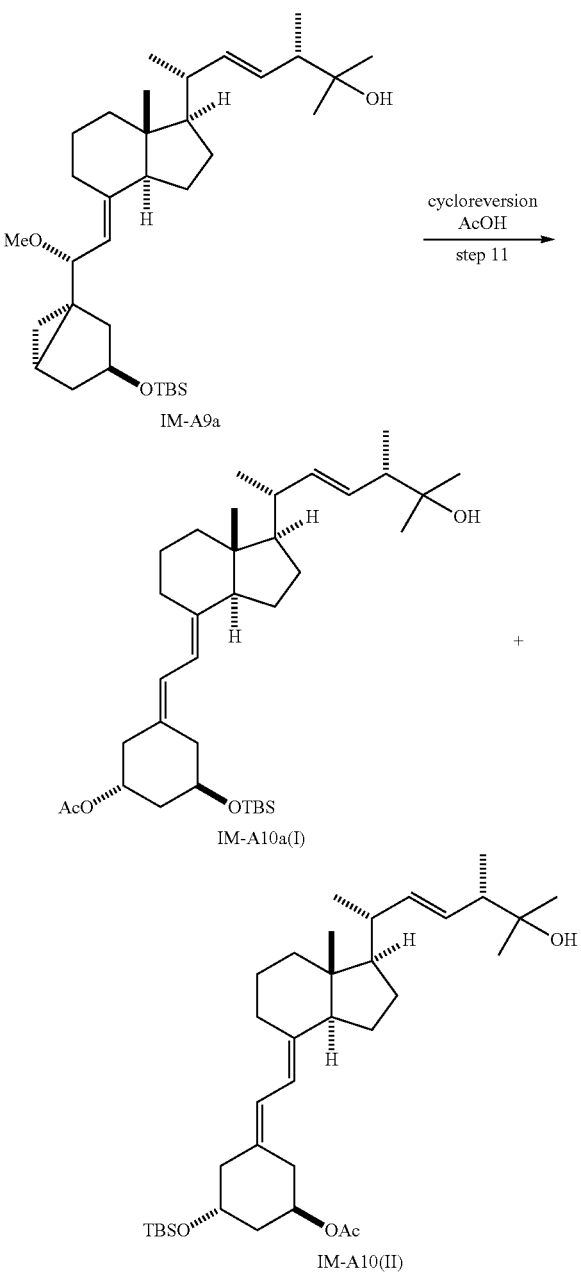

In a typical procedure, IM-A9a is heated in acetic acid at 55° C. yielding a mixture of compounds IM-A10a(I) and IM-A10a(II). After completion of the reaction, the reaction mixture is diluted with water and the work up is continued by extraction of the products from the aqueous layer with MTBE. The organic layer is washed subsequently with water, aqueous 2M sodium hydroxide solution and aqueous sodium chloride solution. Drying of the organic layer with magnesium sulfate, followed by filtration and removal of the solvent by evaporation gives a mixture of IM-A10a(I) and IM-A10a (II) which can be used directly for the next step.

Scheme 42:

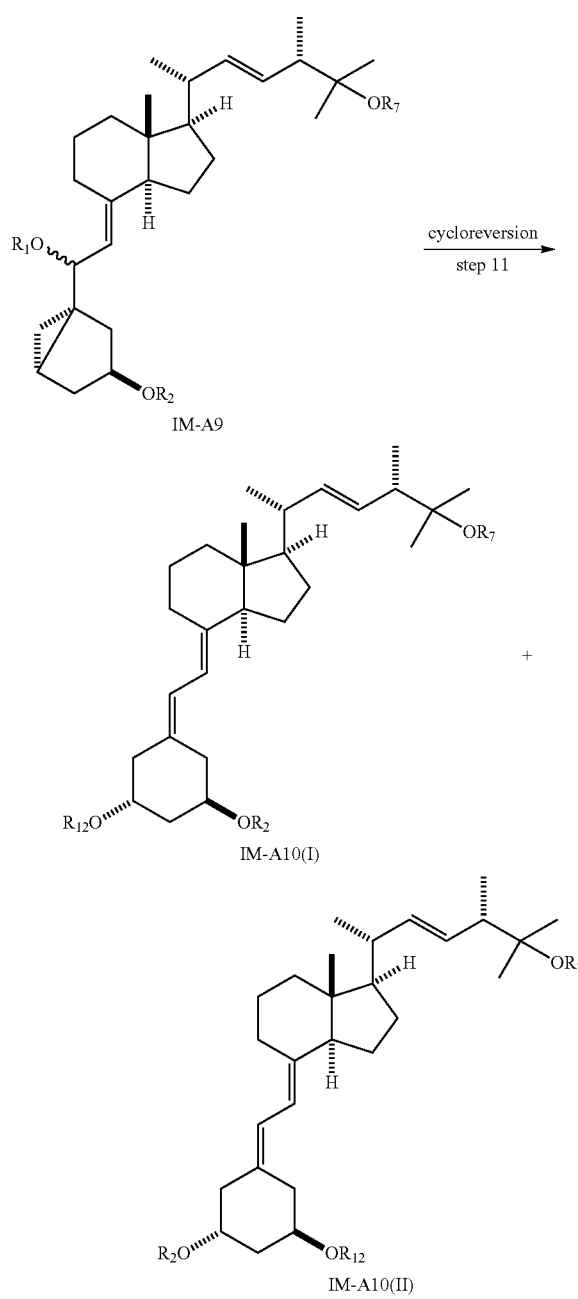

In a particular embodiment IM-A9 is reacted with an $C_1$-$C_4$ alkanoic acid, in amounts, and at a temperature and for a period of time, that are effective for producing compounds of formula IM-A10(I) and IM-A10(II) wherein $R_1$, $R_2$ and $R_{12}$ are defined as described above (Scheme 42). The reaction as well as the isolation of the compounds of formula IM-A10(I) and IM-A10(I) can be carried out in the same manner as described for the conversion of IM-B9 above.

The compounds of formula IM-A10(I) and IM-A10(I) are the protected precursors of paricalcitol and they can be deprotected in analogous procedures as described above and shown in scheme 34.

EXAMPLES

The following examples describe and illustrate the methods for the preparation of paricalcitol and intermediates thereof. Such intermediates may be also useful for the preparation of other 1α-hydroxy-19-nor-vitamin D derivatives. Therefore methods provided within the present invention are intended to be merely illustrative of the present invention, and not limiting thereof in either scope or spirit. Those of skilled in the art will readily understand that variations of certain of the conditions and/or steps employed in the procedures described in the examples can be used to prepare paricalcitol.

All of the ingredients, materials and equipment employed in the examples, and generally employed in the methods of the invention, are commercially available from sources known by those of skilled in the art, such as Sigma-Aldrich Chemie GmbH (Buchs, S G, Switzerland) or ACROS Organics (Geel, Belgium), J. T. Baker (Mallinckrodt Baker B. V., Deventer, Holland) and Merck KgaA (Darmstadt, Germany). TLC: TLC Silica gel 60 $F_{254}$, Aluminium sheets (5×7.5 cm) from Merck KGaA, 64271 Darmstadt, Germany (1.05549.001).

Purity was determined by HPLC (Agilent Technologies, 1100 Series) using a Zorbax SB-Phenyl (150×4.6 mm, 3 μm) column (Agilent Technologies, 863953-912):

Method A

| Reagents: | Water Milli-Q or equivalent |
| --- | --- |
| | Acetonitrile, gradient HPLC grade |
| | Trifluoroacetic acid (TFA) |
| Run time: | 20 min |
| Equilibration time: | 8 min |
| Sample solvents: | acetonitrile/water (1:1) (v/v) |
| Sample solution: | weigh 20.0 mg in volumetric flask of 20 mL, fill to the mark with sample solvent |
| Sample volume: | 5 μl |
| Mobile phases: | A: $H_2O$ |
| | B: acetonitrile |
| | C: 0.1% (v/v) TFA in water |
| | D: 0.08% (v/v) TFA in acetonitrile |

| | time | % of B | % of C | % of D |
| --- | --- | --- | --- | --- |
| Gradient: | 0.00 | 0.00 | 95.0 | 05.0 |
| | 5.00 | 0.00 | 75.0 | 25.0 |
| | 10.0 | 0.00 | 50.0 | 50.0 |
| | 15.0 | 0.00 | 25.0 | 75.0 |
| | 20.0 | 0.00 | 05.0 | 95.0 |

| Flow rate: | 1.0 mL/min |
| --- | --- |
| Column temperature: | 25° C. |
| Detection (DAD): | 224 nm |

Method B

| Reagents: | Water Milli-Q or equivalent |
| --- | --- |
| | Acetonitrile, gradient HPLC grade |
| Run time: | 25 min |
| Equilibration time: | 5 min |
| Sample solvents: | acetonitrile/water (1:1) (v/v) |
| Sample solution: | weigh 20.0 mg in volumetric flask of 20 mL, fill to the mark with sample solvent |
| Sample volume: | 5 μl |
| Mobile phases: | A: $H_2O$ |
| | B: acetonitrile |

| | time | % of B | % of C | % of D |
| --- | --- | --- | --- | --- |
| Gradient: | 0.00 | 45.0 | 0.00 | 0.00 |
| | 3.00 | 45.0 | 0.00 | 0.00 |
| | 20.0 | 98.0 | 0.00 | 0.00 |
| | 25.0 | 98.0 | 0.00 | 0.00 |

| Flow rate: | 1.7 mL/min |
| --- | --- |
| Column temperature: | 30° C. |
| Detection (DAD): | 205 nm |

REFERENCE EXAMPLES

Reference Example 1

Preparation of IM-WR2

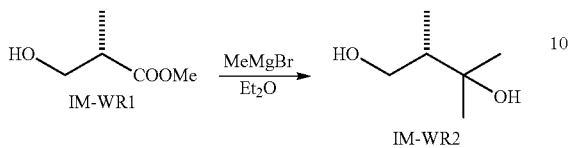

To a stirred solution of MeMgBr (245 mL 3M solution, 3.5 eq.) in Et$_2$O (536 mL) cooled in an ice bad to internal temperature 10-15° C., a solution of methyl (S)-3-hydroxy-2-methyl-propionate (IM-WR1, 25 g, 1 eq.) in Et$_2$O (104 mL) was added drop wise for an interval of 30 min; the internal temperature was kept below 20° C. The obtained grayish suspension was let to reach room temperature (20-25° C.) and was stirred overnight (ca. 12 h). The reaction was completed (monitored by GC); the reaction mixture was cooled again in an ice bad to internal temperature 10-15° C. Next, ice (60 g) and then 5N aqueous HCl solution (150 mL) were very slowly added keeping the internal temperature bellow 25° C. To the resulting emulsion a few drops of HCl solution (ca. 1 mL) were added to adjust pH=4. The both layers of the emulsion were separated; the aqueous phase and a half of the organic phase were put in a continuous liquid liquid extractor (apparatus for performing continuous extraction) and the product was extracted from the aqueous into the organic phase for 24 h (bath temperature 50-56° C.). The organic phases were again combined and concentrated under reduced pressure (600-700 mbar) giving the product as yellowish oil (25.39 g). The latter was purified by distillation at vacuo (0.3-0.1 mbar, 80-95° C.).

Yield of IM-WR2: 22.26 g (88.4%, GC-purity 98.5%)

Reference Example 2

Preparation of IM-WR3

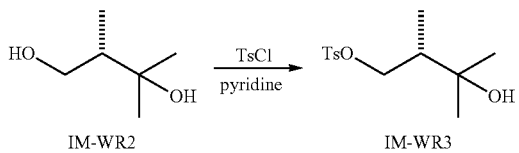

To a stirred solution of IM-WR2 (22.26 g, 1 eq.) in pyridine (200 mL) cooled to an internal temperature of −15° C., solid TsCl (36.76 g, 1.06 eq) was added; during the addition the internal temperature sank to −19° C. The reaction mixture was stirred overnight (approx. 13 h) allowing the mixture to warm to 14° C. whereupon an in-process control showed complete coversion (monitored by GC and HPLC). The obtained white-beige suspension was cooled to 0-5° C., then ice (200 g) was added and the mixture was stirred without cooling until the whole amount of added ice melted. The resulted mixture was extracted 4 times with MTBE (200+150+100+100 mL). The combined MTBE-phases were washed once with aqueous 5N HCl (200 mL, pH of the aqueous phase=4.1) and then twice with 3N aqueous HCl (100+100 mL; pH of the aqueous phase at the end=0.35). Next, the combined MTBE-phases were washed with brine, dried over MgSO$_4$ and concentrated under reduced pressure giving the product as yellowish oil.

Yield of IM-WR3: 49.80 g (95.9%, GC-purity 97.3%)

Reference Example 3

Preparation of IM-WR4

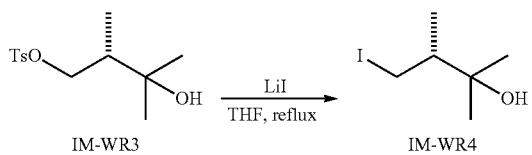

To a solution of IM-WR3 (47.80 g, 1 eq.) in THF (360 mL) stirred at room temperature (20-25° C.), water free LiI (28.05 g, 1.17 eq.) was added; during the addition the internal temperature rose to 44° C. The resulted yellow suspension was heated at reflux for 2 h (monitored by HPLC) and then cooled to room temperature. The suspension was filtered and the filter cake was rinsed with Et$_2$O (3 times 100 mL). The yellow turbid filtrate was washed with saturated aqueous NH$_4$Cl solution (250 mL), dried over MgSO$_4$ and concentrated in vacuo leaving a yellow-orange oil. The oil was dried in vacuo (20 mbar, 30 min).

Yield of IM-WR4: 39.97 g (98.1%, HPLC-purity: 98.26%)

Reference Example 4

Preparation of IM-WR5

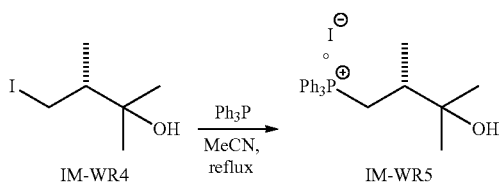

To a well stirred suspension of PPh$_3$ (398.28 g, 8.22 eq.) in MeCN (1100 mL), a solution of IM-WR4 (39.97 g, 1 eq.) in MeCN (100 mL) was added at room temperature (20-25° C.). The reaction mixture was heated at reflux for 29 h (monitored by HPLC) and then cooled to room temperature. The solvent was thoroughly removed by distillation (at the end under reduced pressure of 50 mbar) and the white solid residue was slurred 4 times in Et$_2$O (1000 mL+750 mL+2×700 mL) in order to remove the excess of Ph$_3$P. The product was filtered (68.9 g crude, still containing ca. 7% Ph$_3$P) and then recrystallized from 2-propanol (135 mL) and THF (195 mL) and dried in vacuo at 60° C.

Yield of IM-WR5: 36.43 g (42.3%, HPLC-purity 99.15%)

Recrystallization of IM-WR5 Isolated from Mother Liquor

IM-WR5 (18.20 g, HPLC-assay 87.0%) was dissolved in 2-propanol (37 mL) and heated at 70° C. (internal temperature) giving a clear brown-orange solution. THF (85 mL) was added and the solution was cooled to room temperature (20-25° C.). The mixture was seeded with pure IM-WR5 and stirred over night (ca. 13 h). The yellow suspension was filtered and the filter cake was rinsed Et₂O (20 mL) and THF (20 mL). The wet product was dried in vacuo at 60° C.

Yield of recrystallization 8.24 g (51.5%, HPLC-purity: 99.12%)

The mother liquor was concentrated in vacuo and the residue was recrystallized following the same procedure as described above. A second amount of IM-WR5 (7.27 g) with was obtained (HPLC-purity: 96.53%)

Reference Example 5

Preparation of IM-A1

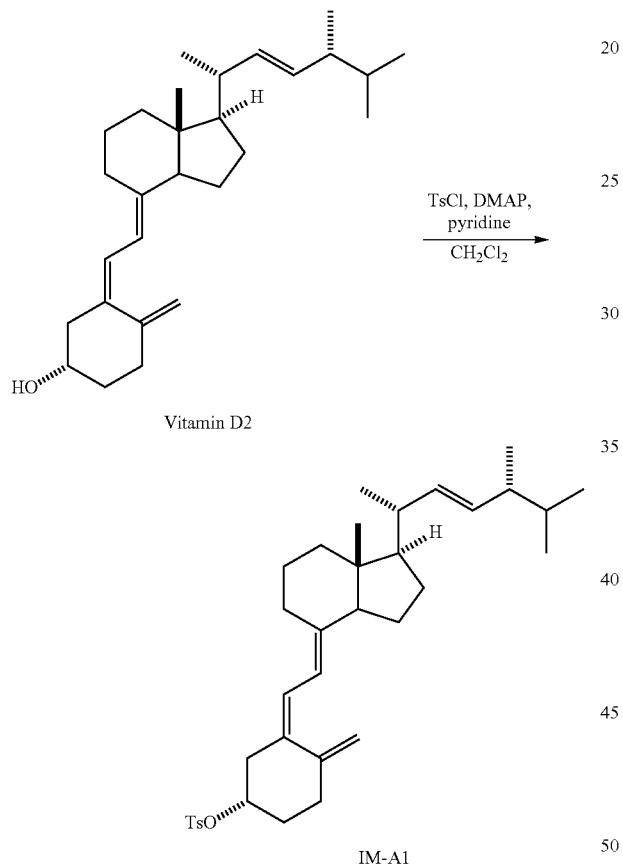

To a stirred solution of vitamin D2 (100 g, 1 eq.) and pyridine (100.7 g, 5 eq.) in CH₂Cl₂ (461 g), DMAP (3.16 g, 0.1 eq.) was added and the solution was cooled to internal temperature of 0-5° C. Then, solid TsCl (98.6 g, 2 eq.) was added portion-wise and the resulting yellow solution was stirred for 64 h at an internal temperature 3-6° C. (TLC monitoring). When the reaction was completed; water was added (250 g) keeping the internal temperature below 5° C. The organic phase was separated and washed with water (100 g), 2M aqueous H₂SO₄ (115 g), 0.5M aqueous H₂SO₄ (200 g) and semi-saturated aqueous NaHCO₃ solution. Next, the organic layer was dried over MgSO₄ and filtered. The filtrate containing IM-A1 was used directly in the next reaction step.

Reference Example 6

Preparation of IM-A2a

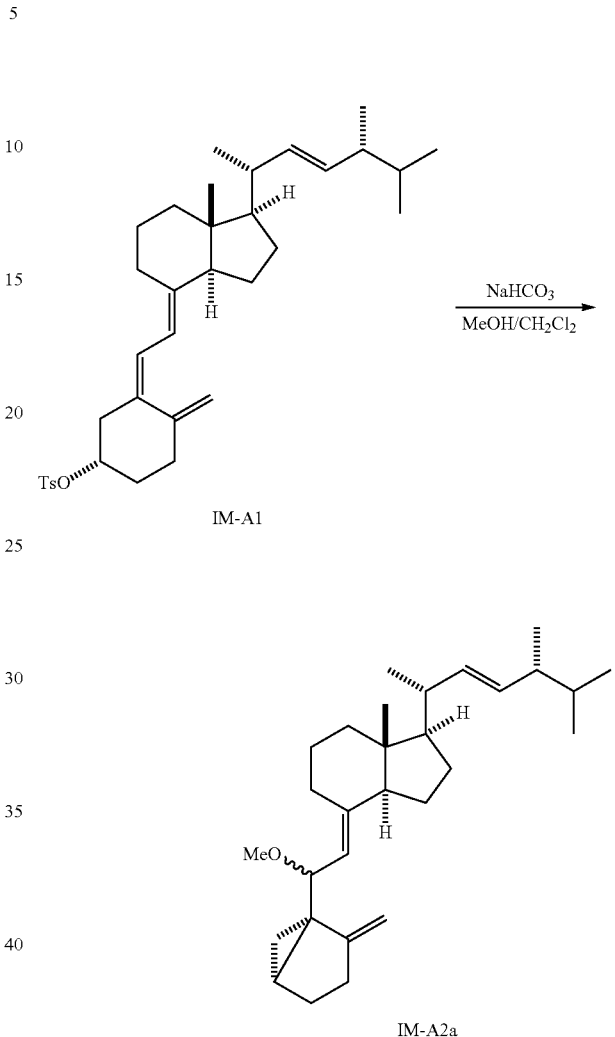

The solution of IM-A1 obtained in Reference Example 5 was added to a stirred suspension of NaHCO₃ (200.20 g, 9.5 eq. calculated on amount of vitamin D₂ in Reference Example 5) in MeOH (1181 g). The resulting milky suspension was heated at internal temperature 50-55° C. for a period of 14-18 h (TLC monitoring). Then, the reaction mixture was cooled to room temperature (20-25° C.), the solid material was filtered and the filtrate was concentrated under reduced pressure giving a beige solid residue. The latter was mixed with MTBE (370 g), water (250 g) and brine (80 g) and stirred until the solid was completely dissolved. The obtained two layers were separated, the aqueous layer was extracted with MTBE (74 g) and the combined organic phases were washed with brine (100 g) and dried over MgSO₄. The solvent was evaporated leaving a yellow oily residue which was used without further purification in the next reaction step.

Yield of IM-A2a 102.3 g (98.8% by weight; combined yield from 2 steps)

Reference Example 7

Preparation of IM-A3a

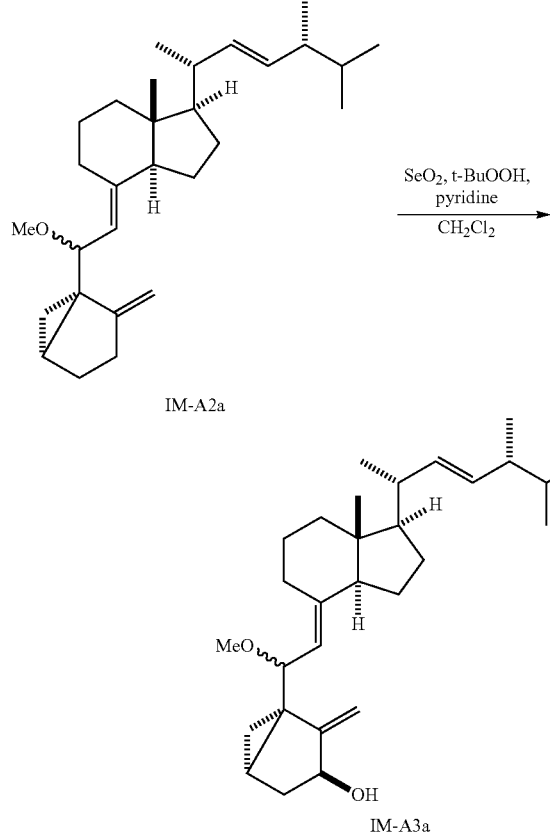

To a well stirred suspension of SeO₂ (11.60 g, 97% purity, 0.4 eq. calculated on the amount of vitamin D2 in Reference Example 5) in CH₂Cl₂ (790 g), tert-butylhydroperoxide (88.5 mL 5.5M solution in decane, 1.93 eq.) and pyridine (17.96 g, 0.9 eq.) were added. After the addition of pyridine, a clear solution was obtained. The solution was cooled to an internal temperature of 0-5° C. Next, a solution of IM-A2a (102.3 g crude product from Reference Example 6, 1 eq.) in CH₂Cl₂ (132 g) was added and the resulted yellowish solution was stirred for 3.5 h (monitored by HPLC) at 0-5° C. After the reaction was completed, ice (100 g), and then aqueous 30% NaOH were added, and the reaction mixture was stirred for additional 15 min. Then, the organic layer was separated and the aqueous layer was extracted twice with CH₂Cl₂ (264+312 g) at internal temperature 0-5° C. The combined organic phases were dried over MgSO₄ and concentrated under reduced pressure. The resulted oily residue was dried azeotropically with toluene (2×172.5 g) and then 60 min in vacuo (20 mbar) giving crude IM-A3a as viscous dark orange oil (128.78 g).

The crude product was purified by column chromatography on silica gel (600 g, column diameter 7.5 cm), mobile phase cyclohexane/AcOEt (100:0 to 75:25).

Yield of IM-A3a 54.84 g (51.0%)

Preparation of Side Chain Synthon for Modified Julia Olefination

Example 1

Preparation of IM-JR4

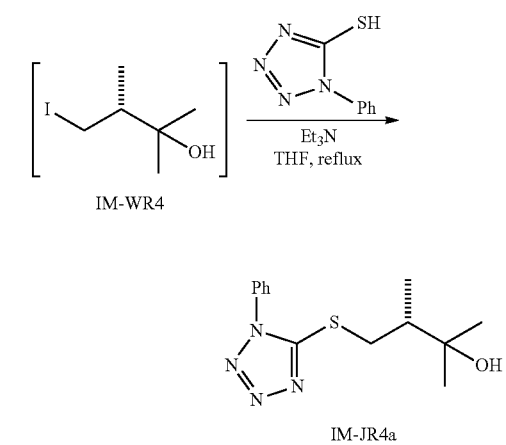

To a solution of IM-WR3 (26.5 g, purity 95%, 1 eq.) in THF (200 mL) stirred at room temperature (20-25° C.), water free LiI (14.76, 1.17 eq.) was added; during the addition the internal temperature rose to 44° C. The resulting yellow solution was heated at reflux for 1.5 h (monitored by HPLC) whereupon after 30 min a suspension was obtained. Then, the reaction mixture was cooled to an internal temperature of 27° C. and 1-phenyl-1H-tetrazole-5-thiol (PTSH, 20.42 g, 1.2 eq.) and Et₃N (14.32 g, 1.5 eq.) were added. The resulting white foamy suspension was heated at reflux for 3.5 h and then at 40° C. for 14.5 h (monitored by HPLC). The reaction mixture was cooled to room temperature (20-25° C.), the solid material was filtered, the filter cake was rinsed with THF (2×50 mL) and the filtrate was concentrated under reduced pressure giving a beige semi-solid residue (69.7 g). The latter was mixed with MTBE (400 mL), water (200 mL) and brine (200 mL) and shaken until the entire solid material was dissolved. The obtained two layers were separated and the aqueous phase was extracted with MTBE (2×100 mL). The combined MTBE-phases were washed with brine (200 mL), dried over MgSO₄, concentrated under reduced pressure to give the product as a brown-orange oil.

Yield of IM-JR4a 26.87 g (101.2%, HPLC purity: 92.4%, still contaminated with reagents)

Example 2

Preparation of IM-JR5a

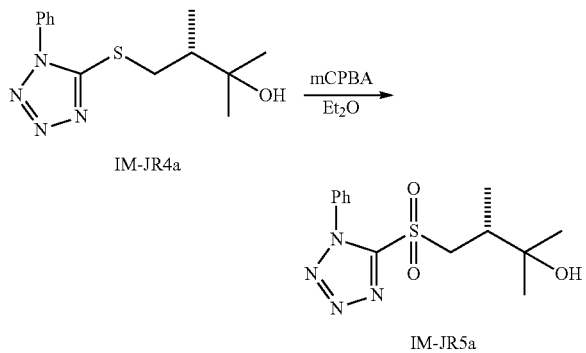

To a stirred solution of IM-JR4a (26.87 g, HPLC purity 92.4%, 1 eq.) in CH$_2$Cl$_2$ (290 mL), m-chloroperoxybenzoic acid (mCPBA, 68.34 g, 70%, 3 eq.) was added at room temperature (20-25° C.) within a period of 5 min (the addition is exothermic). The resulting white suspension was stirred at room temperature for a period of 22 h (monitored by HPLC). Next, the reaction mixture was filtered, the filter cake was rinsed with CH$_2$Cl$_2$ (200+100 mL) and to the filtrate were added ice (200 g), 38-40% aqueous NaHSO$_3$ solution (50 g) and saturated aqueous NaHCO$_3$ solution (420 g). The obtained two layers were separated, the aqueous phase was extracted with CH$_2$Cl$_2$ (250 mL), and the combined organic phases were washed with 3% aqueous NaHCO$_3$ solution (250 mL) and brine (250 mL) and dried over MgSO$_4$. The solvent was removed and the crude end product was obtained as yellowish viscose oil.

Yield of IM-JR5 29.63 g (103.3%, still contaminated with reagents, HPLC-purity: 96.05%)

Example 3

Preparation of IM-JR6a

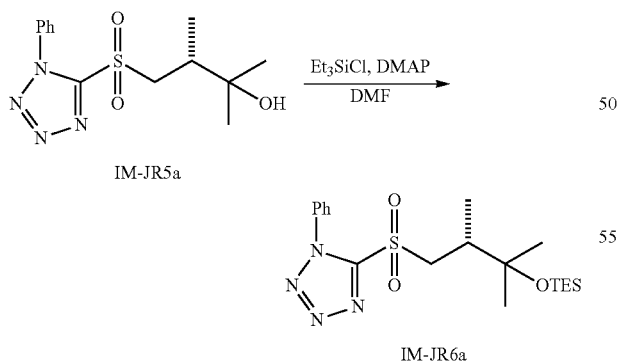

To a stirred solution of IM-JR5 (24.5 g, HPLC-purity 96%, 1 eq.) in DMF (250 mL), DMAP (27.77 g, 3 eq.) was added. The obtained suspension was stirred for 10 min at room temperature (20-25° C.) turning slowly in bright yellow solution. Then Et$_3$SiCl (TESCl, 22.84 g, 2 eq.) was added whereupon a suspension was obtained which was stirred for 27 h (monitored by HPLC). Then, the mixture was poured into a cooled (0-10° C.) mixture of MTBE (500 mL) and water (500 mL) whereby the solid material was dissolved and an emulsion was obtained. The procedure was exothermic and the internal temperature rose to 27° C. The mixture was again cooled down to room temperature and the pH was adjusted to 2.0-2.5 with 2N aqueous HCL (42 mL).

The layers were separated, the organic phase was washed with water (250 mL) and brine (200 mL) and dried over MgSO$_4$. After removing the solvent, the crude product was obtained as yellow transparent oil (41.17 g HPLC-purity 92.31%). It was purified by column chromatography on silica gel (60 g, column diameter 4.5 cm), mobile phase cyclohexane/AcOEt (5:1), Et$_3$N (0.1%).

Yield of IM-JR6a 37.17 g (HPLC purity: 98.21%, HPLC-assay: 84.4%)

Preparation of Paricalcitol

Examples for Route A1

Example A1

Process Step 4

Preparation of 1α-OTBS-6-Methoxycyclovitamine D2 (IM-A4e)

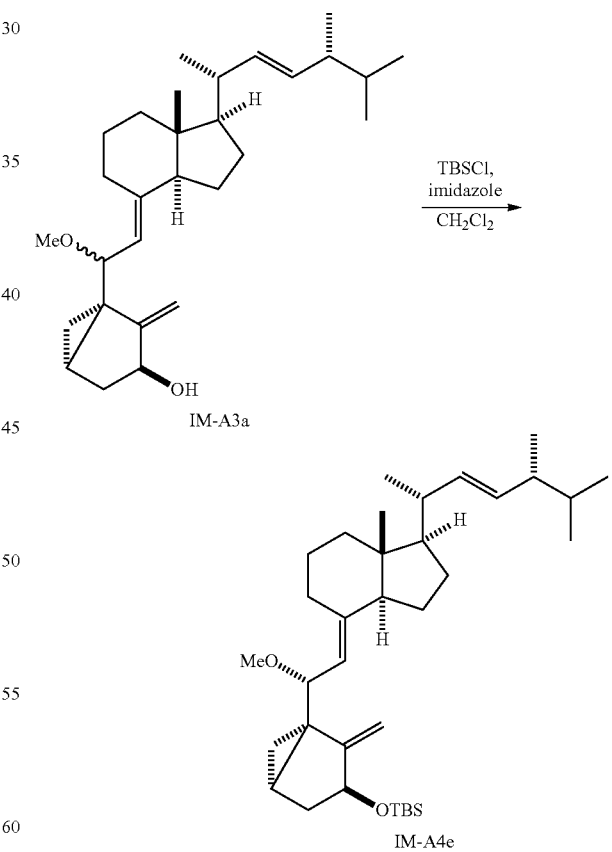

To a stirred solution of 1α-hydroxy-6-methoxycyclovitamin D2 (IM-A3a, 117 g, 1 eq.) in CH$_2$Cl$_2$ (935 mL), imidazole (37.53 g, 2 eq.) was added and the obtained yellow solution was cooled to 0° C. Then, TBSCl (47.86 g, 1.1. eq.) was slowly added keeping the internal temperature between 2° and 8° C. During the addition a yellow suspension was obtained. After 6 h the reaction was completed (monitored by TLC). Next, aqueous 1M NaHSO$_4$ solution (343 mL, 1.25 eq) was added keeping the internal temperature between 4 and 11° C. After separation of the phases, the organic phase was washed with 300 mL saturated aqueous NaHCO$_3$ solution, dried over MgSO$_4$ and concentrated at 43° C. (20 mbar) to give 148.11 g oily residue. This was dissolved in MTBE (90 mL) and to the obtained yellow solution EtOH (1000 mL) was added within a period of 40 min. During the addition of EtOH the solution was seeded. The obtained beige colored suspension was kept overnight (ca. 15 h) at −5° C. The suspension was filtered, the filter cake was washed twice with cooled EtOH and the wet product was dried in vacuo to constant weight.

Yield of IM-A4e: 98.1 g (66.1%).

Example A2

Process Step 5a

Ozonolysis of IM-A4e with Reductive Workup to C(10),C(22)-Dicarbonyl Compound IM-A5e

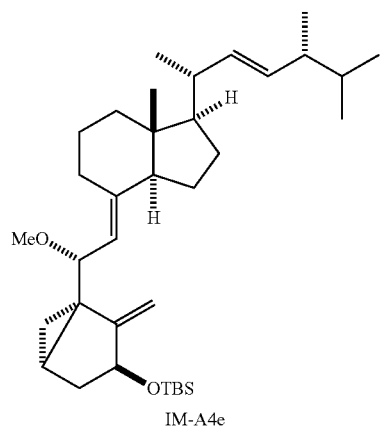

IM-A4e

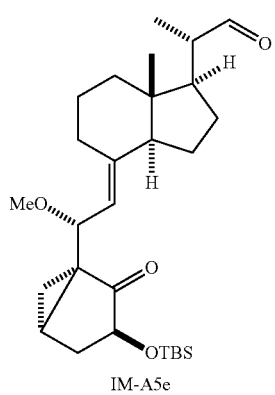

IM-A5e

IM-A4e (5.5 g, 1 eq.) and pyridine (1.75 mL, d=0.978, 2.1 eq.) were dissolved in CH$_2$Cl$_2$ (275 mL) and the solution was cooled in a bath with solid CO$_2$/acetone to temperature ranging from −78° C. to −68° C. Then O$_3$ was bubbled 3 times for periods of 10 mm (the reaction was monitored by TLC). Afterwards gaseous N$_2$ was passed through the solution for a period of 30 min followed by addition of PPh$_3$ (5.8 g, 2.2 eq., internal temperature increased to −50° C.). The reaction mixture was allowed to warm to room temperature (20-25° C.) and poured into a mixture of 1M aqueous NaHSO$_4$ solution (100 mL) and H$_2$O (100 mL). The organic phase was separated, washed with saturated aqueous NaHCO$_3$ solution (100 mL), dried over MgSO$_4$, and concentrated under reduced pressure. The product was purified by column chromatography on silica gel (200 g), mobile phase cyclohexane/AcOEt (100:0 to 85:15). Yield of IM-A5e: 3.81 g (78.9%).

Example A3

Process Step 6

Preparation of IM-A6b

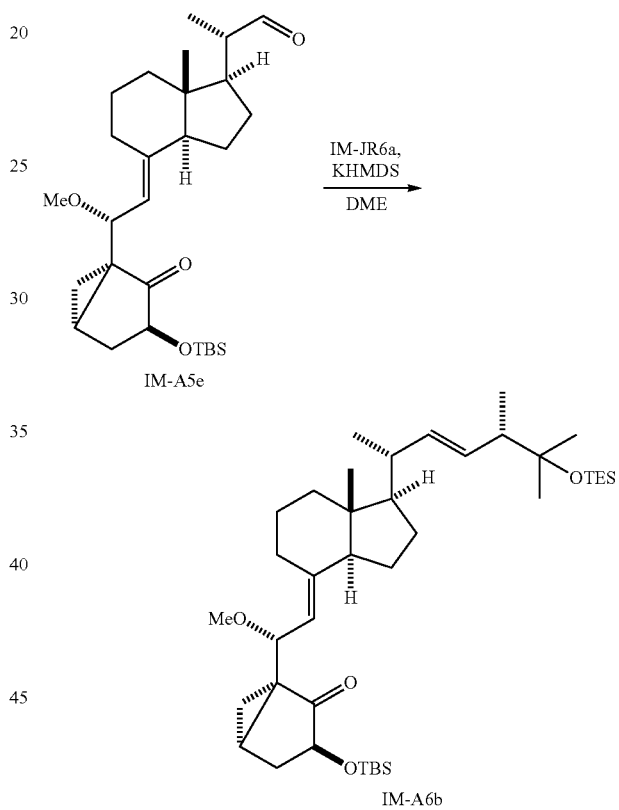

To a solution of phenyltetrazolesulfone IM-JR6a (300 mg, 1 eq.) in DME (6 mL), cooled to −60° C. in a bath with solid CO$_2$/EtOH, 0.5M KHMDS toluene solution (1.56 mL, 1.1 eq.) was added. The mixture was stirred for 1 h and then warmed up to −48° C. Next, a solution of IM-A5e (508 mg, 1.5 eq.) in DME (7 mL) was added keeping the internal temperature below −40° C. The reaction mixture was stirred under these conditions for 3 h and additional 20 h at −20° C. (monitored by TLC). Then, to the reaction mixture MTBE (30 mL) and saturated aqueous NaHCO$_3$ solution (30 mL) were added, the organic phase was separated, dried over MgSO$_4$. After filtration, the solvent was removed and the product was purified by column chromatography on silica gel (25 g), mobile phase cyclohexane/AcOEt (100:0 to 80:20).

Yield of IM-A6b 84 mg (11.7%)

Examples for Route B1

Example B1

Process Step 5

Ozonolysis of IM-A4e with Reductive Workup to C(10),C(22)-Diol Compound IM-B6a

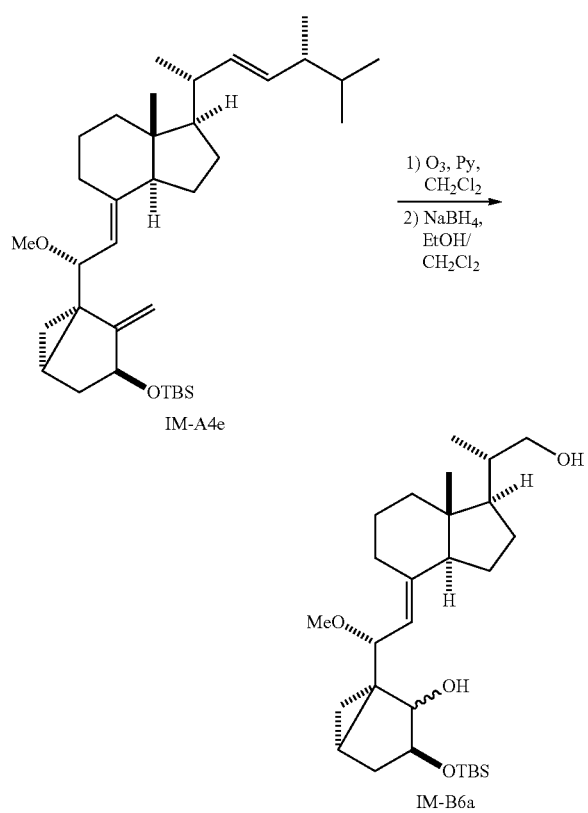

IM-A4e (55.75 g, 1 eq.) and pyridine (17.8 mL, d=0.978, 2.1 eq.) were dissolved in $CH_2Cl_2$ (800 mL) and the stirred solution was cooled in a bath with liquid $N_2$/acetone to temperature ranging from −78° C. to −68° C. Then, $O_3$ (Fischer Ozon Generator Modell 502, flow 140 L/h) was bubbled through the solution for a period of 2.5 h. After this time the reaction was completed (monitored by TLC) and gaseous $N_2$ was passed for a period of 10 min through the solution. $NaBH_4$ (16.26 g, 4 eq.) and then EtOH (300 mL) were added, whereupon the internal temperature rose to −32° C. The reaction mixture was stirred overnight (approx. 15 h) while allowing the mixture to warm to 17° C. Then, acetone (60 mL) was added drop wise (internal temperature increased to 31° C.) and the mixture was concentrated under reduced pressure. To the obtained residue, MTBE (500 mL), $H_2O$ (300 mL) and brine (300 mL) were added and the layers were separated. The organic layer was washed with brine (100 mL), dried over $MgSO_4$ and concentrated under reduced pressure giving an oily residue (62.5 g).

The product was purified by column chromatography (70 mm column diameter) on silica gel (670 g), mobile phase cyclohexane/AcOEt (97:3 to 85:15).

Yield of IM-B6a: 44.64 g (90.5%).

Example B2

Process Step 5b

Reduction of IM-A5e to C(10),C(22)-Diol Compound IM-B6a

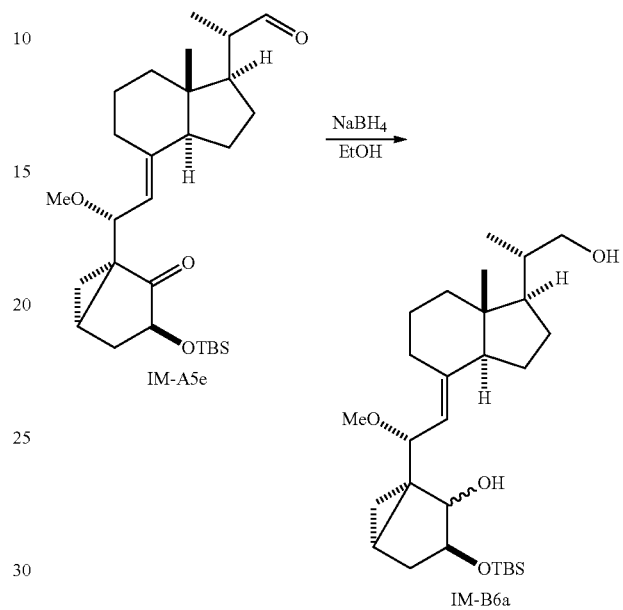

To a stirred solution of IM-A5e (1.5 g, 1 eq.) in EtOH (15 mL), $NaBH_4$ (375 mg, 3 eq.) was added at 20-25° C. The reaction was completed after a stirring period of 5 h (monitored by TLC). MTBE (100 mL) and saturated aqueous $NaHCO_3$ solution (50 mL) were added and the obtained two phases were separated. The organic phase was dried over $MgSO_4$ and concentrated under reduced pressure. The product was purified by column chromatography on silica gel (40 g), mobile phase cyclohexane/AcOEt (9:1 to 7:3).

Yield of IM-B6a: 644 mg (42.6%).

Example B3

Process Step 6

Benzoylation of IM-B6a at C(22)-Hydroxy Group to Compound IM-B7a

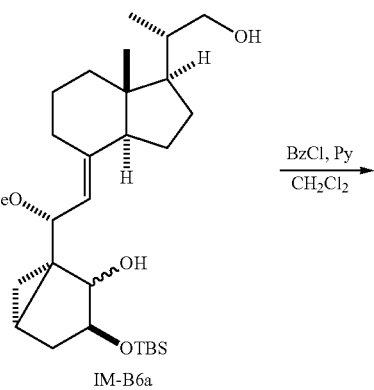

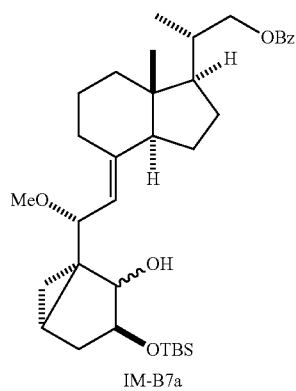

IM-B7a

To a stirred solution of IM-B6a (6.04 g, 1 eq.) in CH₂Cl₂ (60 mL), cooled to 0-5° C., pyridine (3.06 mL, d=0.978, 3 eq.) and then benzoylchloride (2.24 mL, d=1.212, 1.5 eq.) were added. The reaction was completed after stirring for 1.5 h at 0-6° C. (TLC monitoring). Keeping the same internal temperature, water (25 mL) was added and the reaction mixture was stirred additionally for 1 h. Then, additional water (75 mL) was added and the obtained two phases were separated. The aqueous phase was extracted with CH₂Cl₂ (100 mL) and the combined organic phases were washed with saturated aqueous NaHCO₃ solution (50 mL), water (50 mL) and brine (100 mL). The organic phase was dried over MgSO₄ and concentrated at reduced pressure giving an oily residue. The oil was dried first azetropically with toluene (2 times 20 mL) and then under reduced pressure (2 mbar, 40° C.) to constant weight.

Yield of IM-B7a: 8.86 g

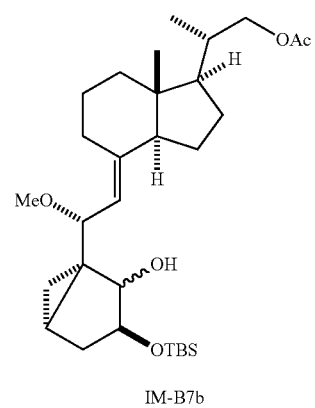

IM-B7b

A solution of IM-B6a (43.64 g, 1 eq.) and pyridine (22.3 mL, 3 eq.) in CH₂Cl₂ (400 mL) was cooled to 0° C. Acetyl chloride (8.76 g, 1.2 eq.) was added drop wise and the mixture was stirred at 0-7° C. and monitored by TLC. After completion of the reaction (1 h) water (10 mL) was added at 0-7° C. and the reaction mixture was stirred additionally for 1 h 10 min at the same temperature. Afterwards additional water (300 mL) was added and the two phases were separated. The aqueous phase was extracted with CH₂Cl₂ (150 mL) and the combined organic phases were washed with 0.5 M aqueous NaHCO₃ solution (150 mL) and dried over MgSO₄. After filtration, the organic phase was concentrated under reduced pressure (13 mbar, 40° C.) and dried to constant weight.

Yield of IM-B7b: 43.63 g (91.9%)

Example B4

Process Step 6

Acetylation of IM-B6a at C(22)-Hydroxy Group to Compound IM-B7b

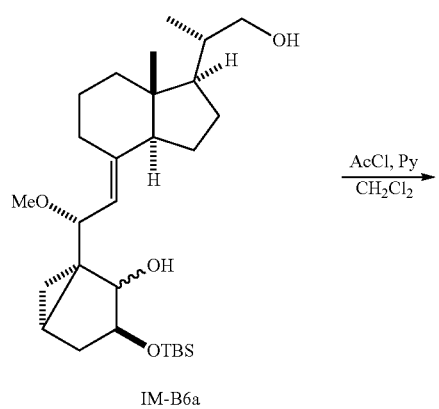

IM-B6a

Example B5

Process Step 7

Mesylation of IM-B7a at C(10)-Hydroxy Group to Compound IM-B8a

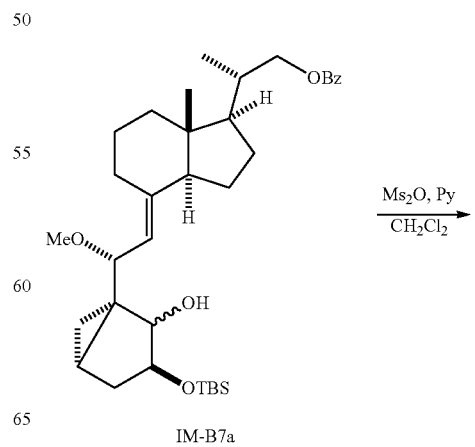

IM-B7a

-continued

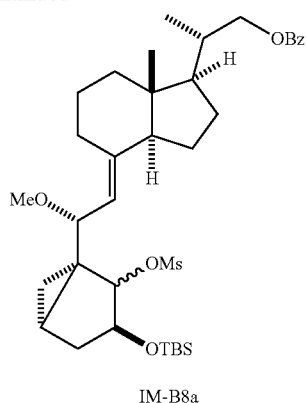

IM-B8a

A stirred solution of IM-B7a (8.86 g, 1 eq.) and pyridine (6.15 mL, (d=0.978, 5 eq.) in $CH_2Cl_2$ (120 mL) was cooled to 5° C. and $Ms_2O$ (5.52 g, 2 eq.) was added. The reaction mixture was stirred for a period of 15 h at an internal temperature of 7° C. and monitored by TLC (there was still starting material detected). The internal temperature was increased to 10° C. and the reaction mixture was stirred additionally for 3 h. Afterwards, water (40 mL), $CH_2Cl_2$ (50 mL) and 0.5 M aqueous $NaHSO_4$ solution (100 mL) were added and the two phases were separated. The organic phase was washed with saturated aqueous $NaHCO_3$ solution (100 mL), dried over $MgSO_4$ and concentrated under reduced pressure. The residue was dried in vacuo (2 mbar, 40° C., 2 h) to constant weight.

Yield of IM-B8a: 10.0 g (99.5%)

Example B6

Process Steps 7 and 8

Mesylation of IM-B7b at C(10)-Hydroxy Group to Compound IM-B8b and Subsequent Reduction to Compound IM-B9a

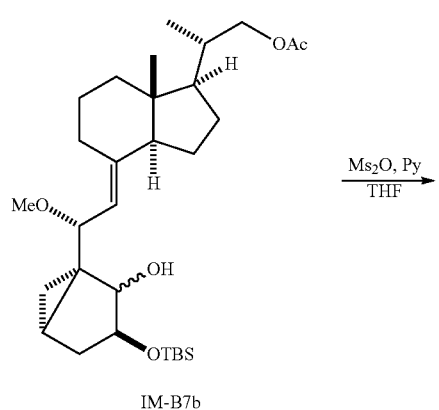

IM-B7b

-continued

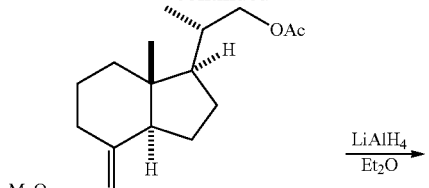

IM-B8b

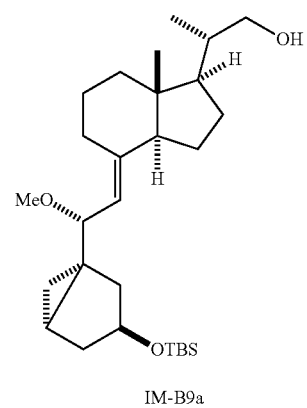

IM-B9a

A stirred solution of IM-B7b (42.51 g, 1 eq.) and pyridine (25 mL, d=0.879, 3.75 eq.) in THF (300 mL) was cooled to 0-5° C. and a solution of $Ms_2O$ in THF (22.22 g, 1.5 eq. in 100 mL) was slowly added. The internal temperature was kept between 0° and 7° C. During the addition a thick suspension was formed. Additional amount of THF (150 mL) was added and the reaction mixture was stirred for a period of 21 h at 20-25° C. and monitored by TLC. After the reaction was completed, the suspension was filtered and the filtrate concentrated under reduced pressure. The residue was taken up in $Et_2O$ (250 mL), the obtained slurry filtered and the filtrate added drop wise to a cooled mixture (0° C.) of $LiAlH_4$ (10 g, 3 eq.) in $Et_2O$ (100 mL). The internal temperature during the addition was kept between 0° and 15° C. After stirring for 3.5 h at a temperature of 0-5° C. the reaction was completed (TLC monitoring). Then acetone (60 mL, 47.3 g, 10 eq.) was added within a period of 40 min (exothermic procedure) while the internal temperature was kept in the range between 0° and 20° C. MTBE (200 mL) and saturated aqueous $NaHCO_3$ solution (400 mL) were added to the reaction mixture at 20-25° C. and the two phases were separated. The aqueous phase was extracted twice with MTBE (200 mL+150 mL) and the combined organic phases were washed with water (2 times 100 mL) and with brine (100 mL). After drying over $MgSO_4$ (16 h, 20-25° C.) the organic phase was concentrated under reduced pressure (33 mbar, 40° C.): residue 40.41 g.

The product was purified by column chromatography (70 mm column diameter) on silica gel (250 g), mobile phase cyclohexane/AcOEt (95:5 to 80:20).

Yield of IM-B9a: 34.5 g (91.3%).

Example B7

Process Step 8

Reduction of Compound IM-B8a to Compound IM-B9a

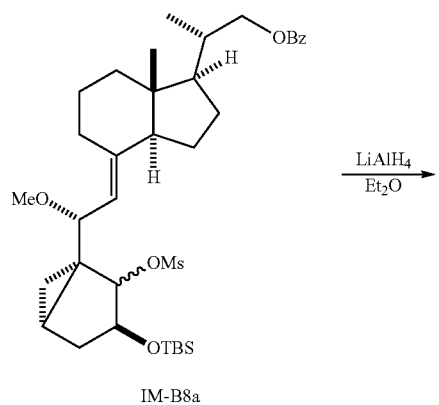

IM-B8a

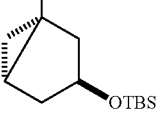

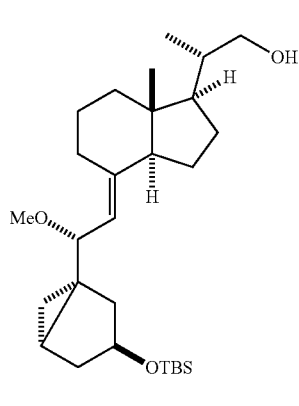

IM-B9a

Example B8

Process Step 9

Cycloreversion of IM-B9a to IM-B10a(I) and IM-B10a(II)

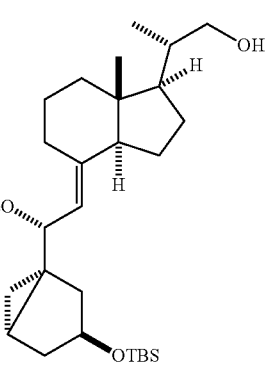

IM-B9a

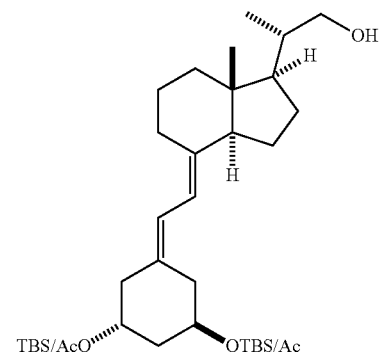

IM-B10a(I) + IM-B10a(II)

A solution of IM-B8a (10 g, 1 eq.) in Et$_2$O (45 mL) was slowly added to a cooled (0° C.) 1M LiAlH$_4$-Et$_2$O solution (45.4 mL, 3 eq.) at an internal temperature between 0° and 5° C. The reaction was completed after stirring for a period of 15 h at 0° C. (TLC monitoring). Then THF (50 mL) and acetone (10 mL) were slowly added (exothermic procedure) keeping the internal below 20° C. Then MTBE (50 mL) and saturated aqueous solution of NaHCO$_3$ (150 mL) were added to the reaction mixture at 20-25° C. and the two phases were separated. The aqueous phase was extracted with MTBE (50 mL) and the combined organic phases were washed with brine (100 mL) and dried over MgSO$_4$. After filtration the organic phase was concentrated under reduced pressure: residue 7.56 g. The product was purified by column chromatography (55 mm column diameter) on silica gel (150 g), mobile phase cyclohexane/AcOEt (50:3 to 5:1).

Yield of IM-B9a: 5.27 g (75.4%).

A solution of IM-B9a (1.05 g) in acetic acid (10 mL) was heated at 55° C. for 30 min. Then, water (50 mL) and MTBE (50 mL) were added and the obtained two phases were separated. The organic phase was washed with water (2 times 50 mL) and saturated aqueous NaHCO$_3$ solution (50 mL). The aqueous phase was extracted with MTBE (50 mL) and the combined organic phases were concentrated under reduced pressure to give yellowish oily residue. The oil was dissolved in MTBE (50 mL) and washed with aqueous Na$_2$CO$_3$ solution (5%, 50 mL) and brine (50 mL). The MTBE layer was dried with MgSO$_4$ and concentrated under reduced pressure. The resulting yellow foam was dried in vacuo (6 mbar, 35° C.) and then directly used for the subsequent Swern oxidation (Example 15).

Example B9

Process Step 10

Oxidation of IM-B10a(I) and IM-B10a(II) to IM-B11a(I) and IM-B11a(II) (Swern)

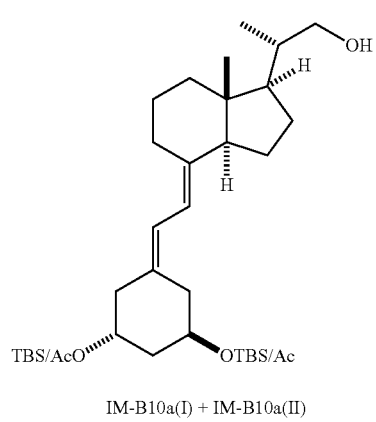

IM-B10a(I) + IM-B10a(II)

IM-B11a(I) + IM-B11a(II)

To a mixture of DMSO (713 mg, 4 eq.) in $CH_2Cl_2$ (10 mL), cooled to −78° C. in a bath with solid $CO_2$/acetone, oxalylchloride (600 mg, 2 eq.) was added and the reaction mixture was stirred for 30 min. A solution of IM-B10a(I) and IM-B10a(II) (crude product from example 14) in $CH_2Cl_2$ (5 mL) was first dried over molecular sieve (4A, 0.6 g) and then added to the DMSO/oxalylchloride mixture. After stirring for 30 min, $Et_3N$ (2 mL) was added. Stirring was continued for 10 min (an in-process control showed completion of the reaction (TLC monitoring) before the mixture was worked up at room temperature (20-25° C.). MTBE (75 mL) and saturated aqueous $NaHCO_3$ solution (75 mL) were added and the obtained two phases were separated. The organic phase was washed with water (50 mL) and brine (50 mL). The solvent of the organic layer was removed under reduced pressure to give a yellowish oily residue (1.03 g). The product was purified by column chromatography on silica gel (50 g), mobile phase cyclohexane/AcOEt (95:5 to 90:10).

Yield of IM-B11a(I) and IM-B11a(II): 715 ing (60%, 2 steps)

Example B10

Process Step 11

Julia Olefination of IM-B11a(I) and IM-B11a(II) to IM-A10b(I) and IM-A10b(II)

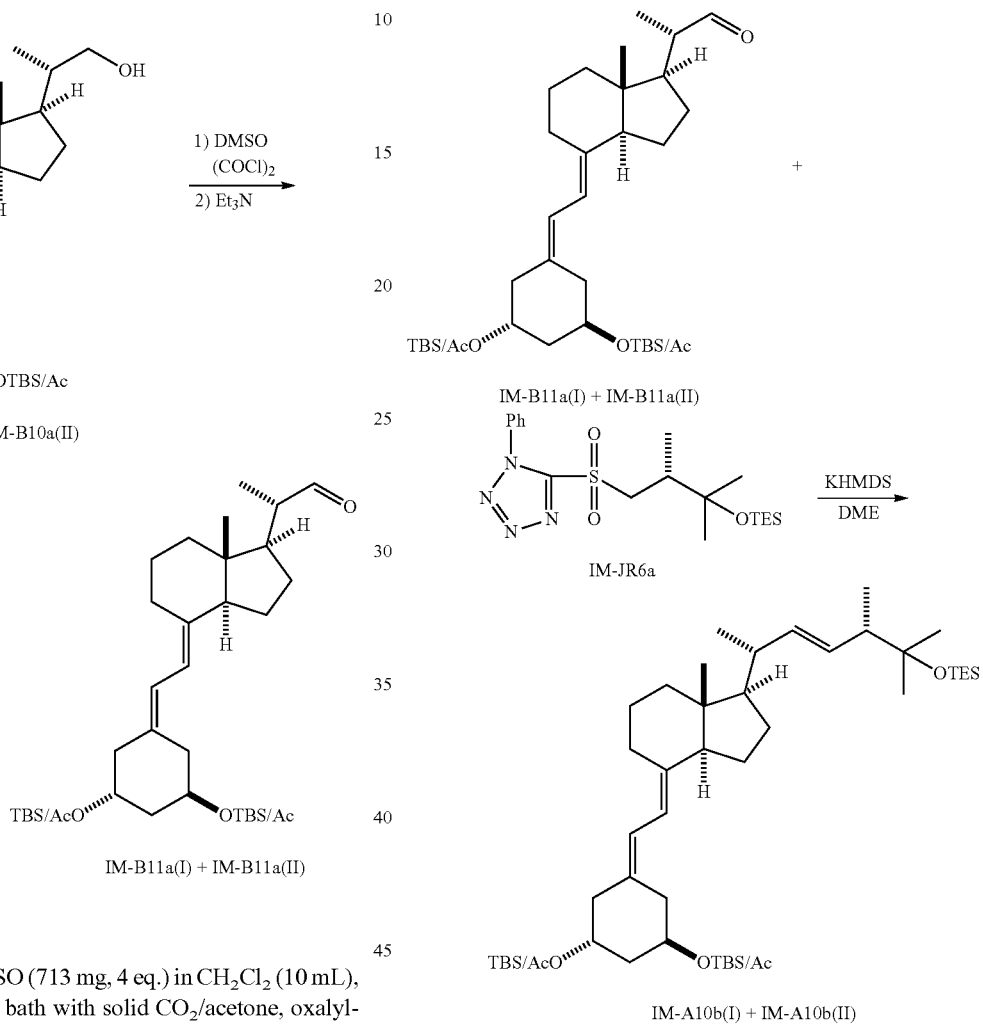

IM-B11a(I) + IM-B11a(II)

IM-JR6a

IM-A10b(I) + IM-A10b(II)

A solution of phenyltetrazolesulfone IM-JR6a (143 mg, 1.1 eq.) in DME (3 mL), was cooled to −25° C. Then a 0.5M KHMDS solution in toluene (0.71 mL, 1.15 eq.) was added. The mixture was stirred for 15 min and then a solution of aldehydes IM-B11a(I) and IM-B11a(II) (150 mg, 1 eq.) in DME (0.43 mL) was added keeping the internal temperature between −20° and −15° C. After the addition, the internal temperature was increased to −10° C. and the reaction mixture was stirred for 4 h and monitored by TLC. Then MTBE (20 mL) and saturated aqueous $NaHCO_3$ solution (20 mL) were added and the phases were separated. The organic phase was dried over $MgSO_4$ and concentrated under reduced pressure. The crude product was purified by column chromatography on silica gel (25 g), mobile phase cyclohexane/AcOEt (98:2 to 90:10) giving a mixture of IM-A10b(I) and IM-A10b (II).

Yield of IM-A10b(1) and IM-A10b(II): 41 mg (10.6%; HPLC purity 54.8%; main impurity: starting material IM-JR6)

Example B11

Process Step 12

Deprotection of IM-A10b(I) and IM-A10b(II) to Paricalcitol

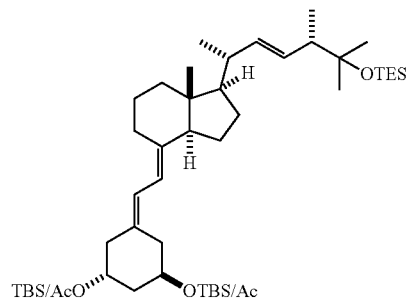

IM-A10b(I) + IM-A10b(II)

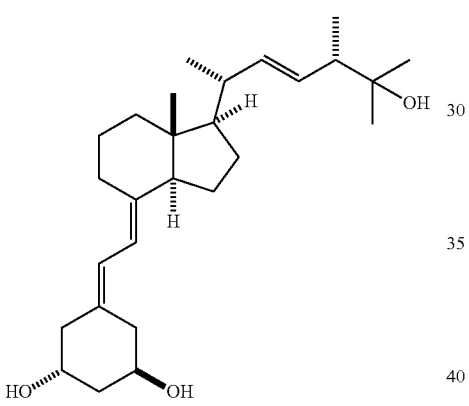

Paricalcitol

A mixture consisting of IM-A10b(I) and IM-A10b(II) (41 mg, HPLC purity 54.8%) was dissolved in 1M TBAF in THF (1.5 mL) at temperature 20-25° C. and stirred for 2 h. Then, the reaction mixture was diluted with MeOH (1.5 mL) and 2M aqueous NaOH (0.3 mL) was added. The mixture was stirred for another 2 h and monitored by TLC. Then AcOEt (20 mL) and saturated aqueous $NaHCO_3$ solution (20 mL) were added and the phases separated. The organic phase was washed with brine (20 mL), dried over $MgSO_4$ and concentrated under reduced pressure. The product was purified by column chromatography on silica gel (15 g), with mobile phase cyclohexane/AcOEt (100:0 to 92:8).

Yield 11 mg (81%).

In an additional purification, the product (Paricalcitol, 11 mg) was dissolved in acetone (1 mL) at 35-40° C. The solution was filtered and then cooled to −18° C. to initiate crystallization. The obtained slurry was stirred for 15 min at room temperature (20-25° C.) and again cooled to −18° C. for 3.5 h. The solid material was filtered off, washed with cold (−18° C.) acetone (0.25 mL) and dried in vacuo (6 mbar, 40° C.).

Yield of paricalcitol: 4 mg (36%, HPLC purity 98.3%)

Examples for Route C1

Example C1

Process Step 9

Oxidation of IM-B9a to IM-C10a (Corey-Kim)

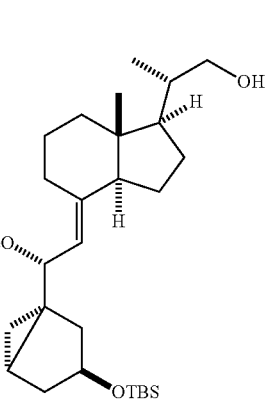

IM-B9a

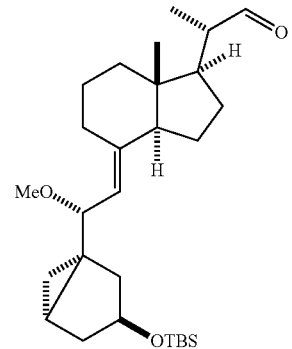

IM-C10a

To a stirred solution of N-chlorosuccinimide (2.21 g, 2.5 eq.) in $CH_2Cl_2$ (60 mL), cooled in an ice bath to 0-5° C., $Me_2S$ (1.68 mL, d=0.847, 3.5 eq.) was added. During the addition, the temperature was kept in the range of 0-8° C. The obtained suspension was stirred for 30 min and was then cooled to −28° C. To this mixture a solution of IM-B9a (3.0 g, 1 eq.) in $CH_2Cl_2$ (30 mL) was slowly added. The reaction mixture was stirred for 1 h at −28° C. Then $Et_3N$ (1.98 g, 3 eq.) was added drop wise. The reaction was completed after stirring for additional 10 min (TLC monitoring). Saturated aqueous $NaHCO_3$ solution (50 mL) was added increasing the internal temperature to 0° C. Then $CH_2Cl_2$ (150 mL) and brine (30 mL) were added and the phases were separated. The organic layer was dried over $MgSO_4$, concentrated under reduced pressure to reach a volume of approx. 50 mL which were then dried azeotropically with toluene (50 mL). Removing of the solvents in vacuo gave a yellowish oily residue (ca. 5 g) from which the desired product was isolated by column chromatography on silica gel (60 g), mobile phase cyclohexane/AcOEt (100:0 to 90:10).

Yield of IM-C10a: 1.62 g (54%)

Example C2

Process Step 9

Oxidation of IM-B9a to IM-C10a (Dess-Martin)

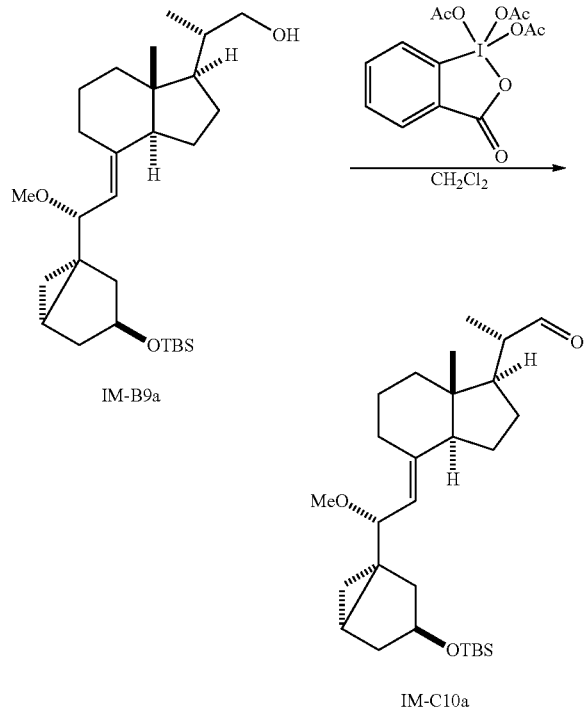

Dess-Martin periodinane (2.16 g, 15%) was added to a stirred solution of IM-B9a (236 mg, 1 eq.) in CH$_2$Cl$_2$ (1.5 mL) at room temperature (20-25° C.). After stirring for 2 h an in-process TLC analysis showed a complete conversion. The reaction mixture was added to a mixture of saturated aqueous NaHCO$_3$ solution (20 mL), CH$_2$Cl$_2$ (20 mL) and 1.0 g Na$_2$S$_2$O$_3$. The organic phase was separated, dried with MgSO$_4$ and concentrated in vacuo giving 0.28 g of yellow oil (IM-C10a, still contaminated with reagent).

Example C3

Process Step 9

Oxidation of IM-B9a to IM-C10a (Swern, Modified)

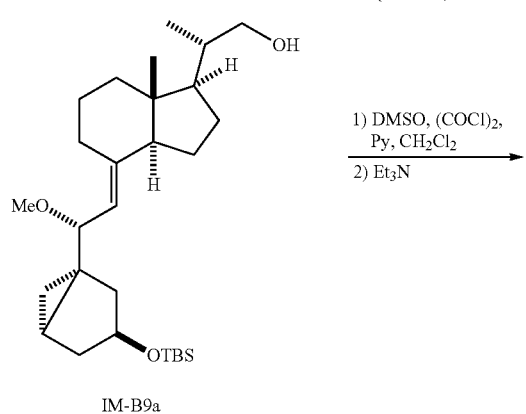

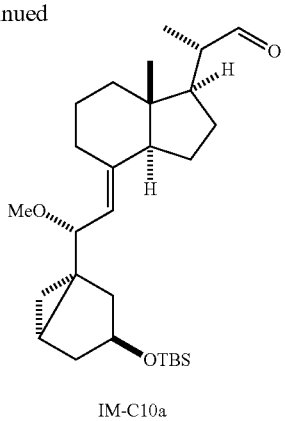

To a mixture of DMSO (3.18 g, 2.5 eq.) in CH$_2$Cl$_2$ (50 mL), cooled to −78°, oxalylchloride (3.21 g, 1.5 eq.) was added drop wise, keeping the internal temperature below −60° C. Thereafter, the mixture was stirred 45 min at an internal temperature ranging from −60° C. to −78° C. After the addition of pyridine (3.24 g, d=0.978, 2.5 equivalent), the mixture was stirred for 15 min before a solution of IM-B9a (36.37 g, 20.62%, 1 eq) in CH$_2$Cl$_2$ was added (the addition was exothermic) while keeping the internal temperature below −60° C. The mixture was stirred for 30 min and Et$_3$N (9.1 mL) was added at a temperature below −50° C. (the addition was exothermic). Additional CH$_2$Cl$_2$ (45 mL) was added facilitating the stirring and the reaction mixture was stirred for 2.5 h (TLC monitoring).

Then water (75 mL) was added and the internal temperature was allowed to warm first to 0° C. and then room temperature (20-25° C.). The organic phase was separated and the aqueous phase was extracted with CH$_2$Cl$_2$ (50 mL). The combined CH$_2$Cl$_2$ phases were concentrated under reduced pressure leaving an oily residue. The oil was dissolved in MTBE (60 mL) and the solution was washed with saturated aqueous NaHCO$_3$ solution (60 mL) and brine (2 times 60 mL).

The organic phase was dried over MgSO$_4$, concentrated under reduced pressure, dried azeotropically with toluene (50 mL) and concentrated in vacuo again. The product was isolated by column chromatography on silica gel (75 g), mobile phase cyclohexane/AcOEt (100:0 to 90:10).

Yield of IM-C10a: 6.92 g (92.6%)

Example C4

Process Step 10

Wittig Reaction of IM-C10a to IM-A9a

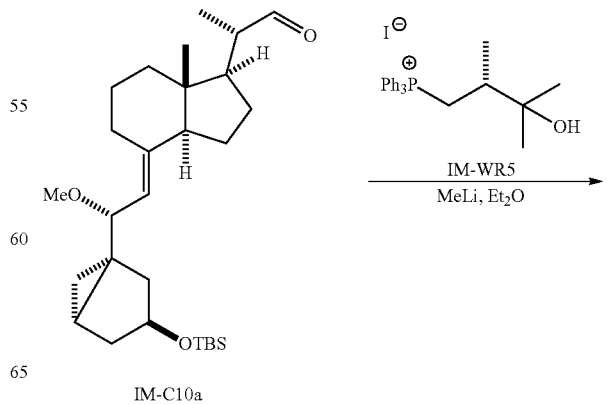

-continued

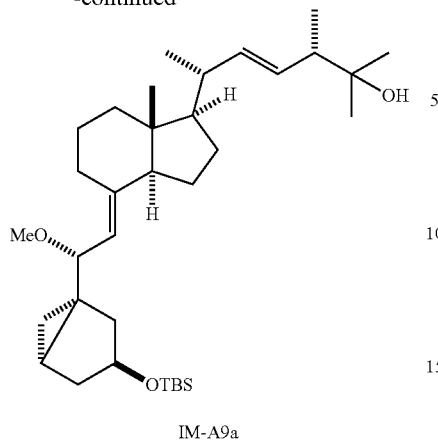

IM-A9a

MeLi (48,84 mL of a 1.6 M solution in Et$_2$O, 3 eq.) was added under N$_2$ atmosphere to a slurry of phosphonium iodide IM-WR5 (19.16 g, 1.5 eq.) in Et$_2$O (120 mL), cooled in an ice bath, within a period of 15 min. The color of the reaction mixture changed first to yellow and then to red-orange. The mixture was allowed to warm to room temperature, stirred at this temperature for 1 h and cooled to −25° C. EtOAc (12 mL) was added followed by dropwise addition of a solution of IM-C10a (12.0 g, 1 eq.) in Et$_2$O (60 mL), which was previously dried over molecular sieve (4A, 3 g). The reaction mixture was stirred for 5 h at temperature range between −25° and −18° C. (TLC and HPLC monitoring). After complete conversion, the reaction mixture was slowly added at room temperature to a stirred mixture of aqueous NaHCO$_3$ solution (12 g in 300 mL water) and MTBE (300 mL). After 15 min the biphasic mixture was filtered over a glass filter, and the phases were separated. The aqueous phase was extracted with MTBE (200 mL), and the combined organic phases were washed with brine (200 mL), and dried over MgSO$_4$. After removing the solvent in vacuo, a yellow-green oily residue (18.15 g) was obtained. The product was purified by column chromatography on silica gel (250 g), mobile phase cyclohexane/AcOEt (95:5 to 85:15).

Yield of IM-A9a: 8.36 g (58.6%, HPLC-purity 72.9%)

Example C5

Process Step 11

Cycloreversion of IM-A9a to IM-A10a(I) and IM-A10a(II)

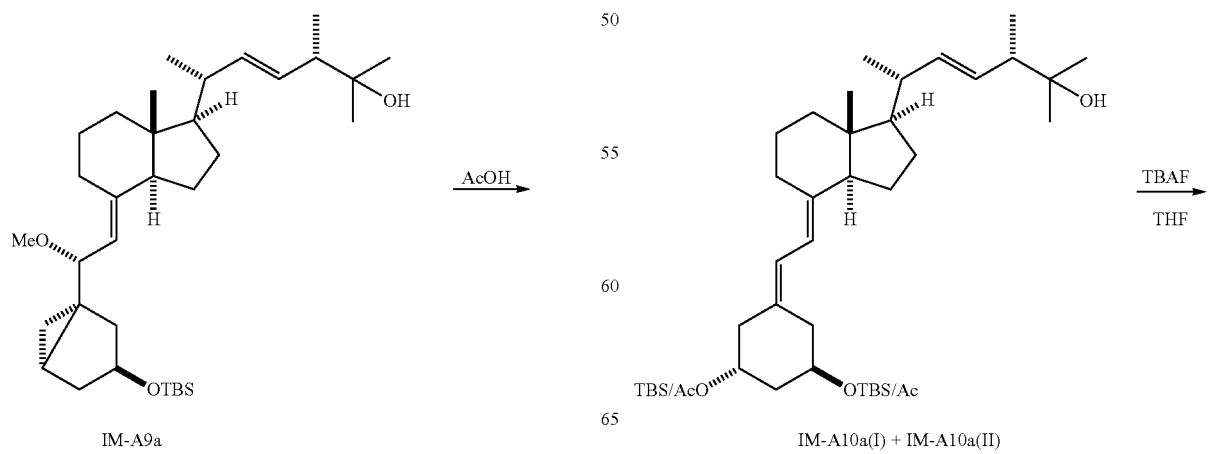

-continued

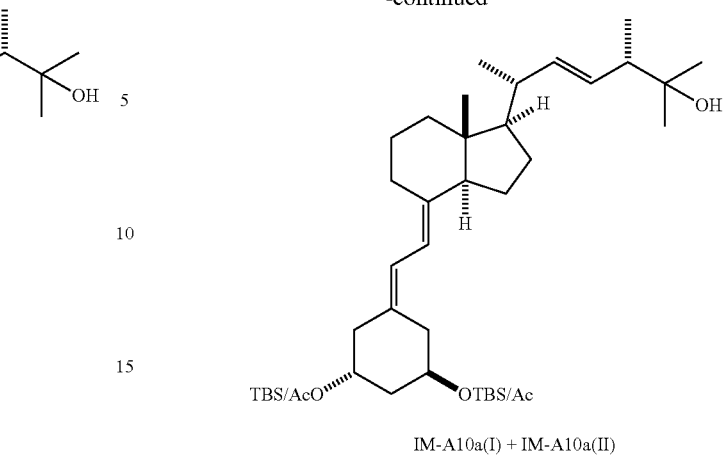

IM-A10a(I) + IM-A10a(II)

The product of the Wittig reaction IM-A9a (11.1 g, 1 eq.) was dissolved in AcOH (167 mL, 15 eq. volume/weight) and the solution was heated for 30 min at temperature 55-60° C. (TLC and HPLC monitoring). After the conversion was complete, the reaction mixture was added to a mixture of MTBE (300 mL) and water (600 mL). The organic phase was separated and washed with water (2 times 500 mL) and the combined aqueous phases were extracted with MTBE (200 mL). The organic phase was washed with a mixture of 2M aqueous NaOH (200 mL), brine (200 mL), saturated aqueous NaHCO$_3$ solution (200 mL) and again with brine (200 mL). The solvent of the combined organic phases was removed in vacuo giving a yellowish resin consisting of a mixture of IM-A10a(I) and IM-A10a(II).

Yield of IM-A10a(I) and IM-A10a(II): 9,61 g (82.3%, HPLC-purity 87.9%)

Example C6

Process Step 12

Desilylation of IM-A10a(I) and IM-A10a(II) to IM-A11a(I) and IM-A11a(II)

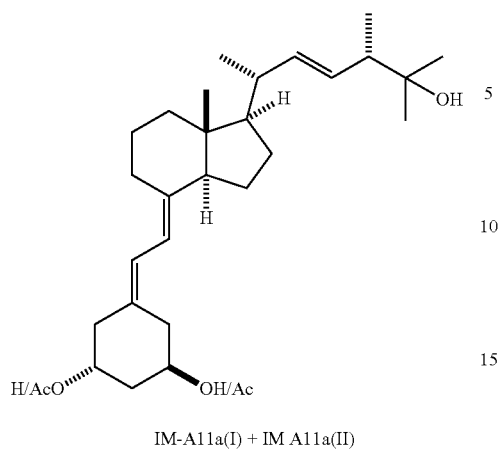

IM-A11a(I) + IM A11a(II)

A mixture of IM-A10a(I) and IM-A10a(II) (9.6 g, HPLC-purity 87.9%) was dissolved in THF (50 mL), 1M TBAF solution in THF (50 mL) was added and the obtained solution was stirred for 1.5 h at room temperature (TLC monitoring). The reaction mixture was poured into MTBE (300 mL) and a mixture of brine and saturated aqueous $NaHCO_3$ (200 mL, 1:1) were added. The phases were separated and the organic layer was washed with brine (200 mL). The first aqueous phase was extracted with MTBE (200 mL) and the solvent of the combined organic phases was removed in vacuo. The crude product was purified by column chromatography on silica gel (200 g), mobile phase cyclohexane/AcOEt (80:20 to 55:45) giving 3.18 g of a first product fraction. A second impure fraction was obtained, which was purified by column chromatography on silica gel (100 g), mobile phase cyclohexane/AcOEt (75:25 to 60:40) giving 2.06 g additional product. The products were obtained as mixtures consisting of IM-A11a(I) and IM-A11a(II).

Yield of IM-A11a(I) and IM-A11a(II): 5.24 g (56.1% based on IM-A9a, HPLC-purity 94.2%)

Example C7

Process Step 12

Hydrolysis of IM-A11a to Paricalcitol

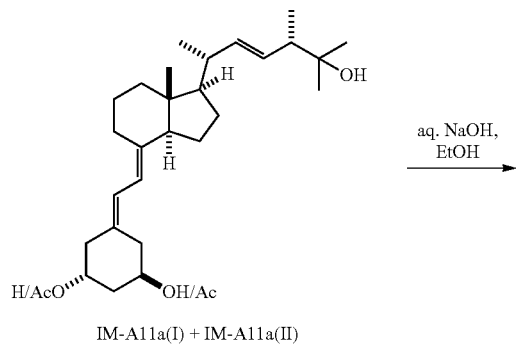

IM-A11a(I) + IM-A11a(II)

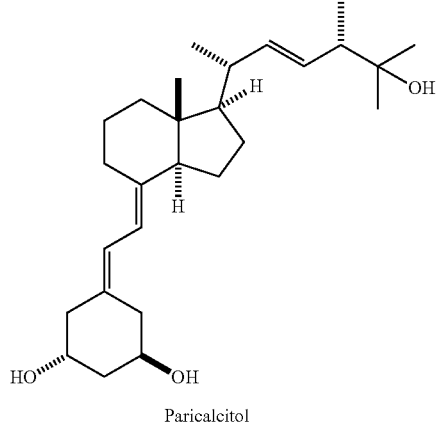

Paricalcitol

To a solution of IM-A11a(I) and IM-A11a(II) (5.24 g, HPLC-purity 94.2%) in EtOH (80 mL) was added at room temperature (20-25° C.) 2M aqueous NaOH solution (8 mL). The reaction mixture was stirred for 1 h 20 min (TLC monitoring), then EtOAc (8 mL) was added and the mixture was concentrated under reduced pressure to a volume of 40 mL whereupon the crystallization started. Water (50 mL) was added to the suspension and after stirring for 75 min at room temperature the solid was isolated by filtration (pH of the mother liquor measured 8-9). The wet product was slurried in $EtOH/H_2O$ (24 g, 1:1) at room temperature, filtered, washed with $EtOH/H_2O$ (5 mL, 1:1) and dried (40° C., 10 mbar). Yield of paricalcitol: 4.26 g (89.5%, HPLC-purity 97.7%).

TABLE I

| Crystallographic Data | |
|---|---|
| Crystallised from | $CH_2Cl_2$/MeOH |
| Empirical formula | $C_{35}H_{60}O_2Si$ |
| Formula weight [g $mol^{-1}$] | 540.94 |
| Crystal colour, habit | colourless, prism |
| Crystal dimensions [min] | 0.15 × 0.20 × 0.25 |
| Temperature [K] | 160(1) |
| Crystal system | orthorhombic |
| Space group | $P2_12_12_1$ (#19) |
| Z | 4 |
| Reflections for cell determination | 97123 |
| 2θ range for cell determination [°] | 4-50 |
| Unit cell parameters a [Å] | 7.1648(1) |
| b [Å] | 19.8120(1) |
| c [Å] | 24.3095(2) |
| α [°] | 90 |
| β [°] | 90 |
| γ [°] | 90 |
| V [Å³] | 3450.71(6) |
| F(000) | 1200 |
| $D_x$[g $cm^{-3}$] | 1.041 |
| μ(Mo Kα) [$mm^{-1}$] | 0.0943 |
| Scan type | φ and ω |
| 2θ(max) [°] | 50 |
| Transmission factors (min; max) | 0.672; 0.989 |
| Total reflections measured | 41124 |
| Symmetry independent reflections | 6062 |
| $R_{int}$ | 0.083 |
| Reflections with I >2σ(I) | 5303 |
| Reflections used in refinement | 6061 |
| Parameters refined | 355 |
| Final R(F) [I > 2σ(I) reflections] | 0.0589 |
| $wR(F^2)$ (all data) | 0.1590 |
| Weights: | $w = [\sigma^2(Fo^2) + (0.0855P)^2 + 1.8535P]^{-1}$ where $P = (F_o^2 + 2F_c^2)/3$ |
| Goodness of fit | 1.050 |
| Secondary extinction coefficient | 0.007(2) |
| Final $\Delta_{max/\sigma}$ | 0.001 |

TABLE I-continued

| Crystallographic Data | |
|---|---|
| $\Delta\rho$ (max; min) [e Å$^{-3}$] | 1.33; −0.39 |
| $\sigma(d(C_{-C}))$ [Å] | 0.004 – 0.007 |

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

The invention claimed is:

1. A process for preparing 19-nor-1α,3β,25-trihydroxy-9,10-secoergosta-5 (Z),7(Z),22(E)-triene (paricalcitol) of the formula

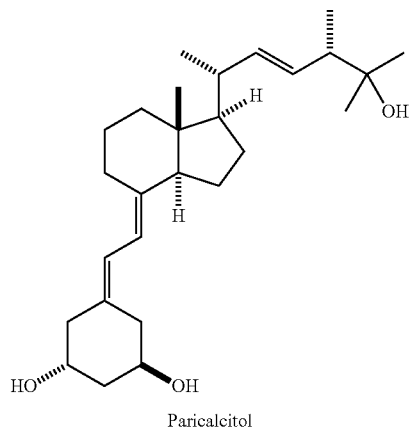 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Paricalcitol wherein vitamin D2 is used as starting material and wherein a compound of the formula

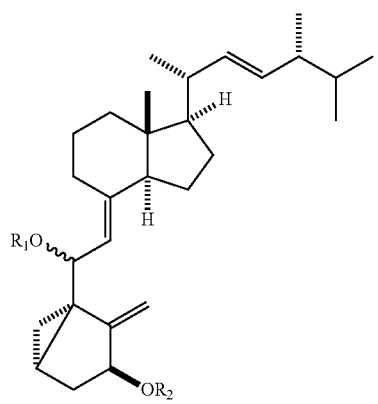

IM-A4 wherein $R_1$ represents a $C_1$-$C_4$ alkyl group and $R_2$ represents a hydroxyl protecting group
is used as an intermediate,
the process comprising synthesizing IM-A4 from vitamin D2 and further comprising the steps of:

(a) subjecting a compound of the formula

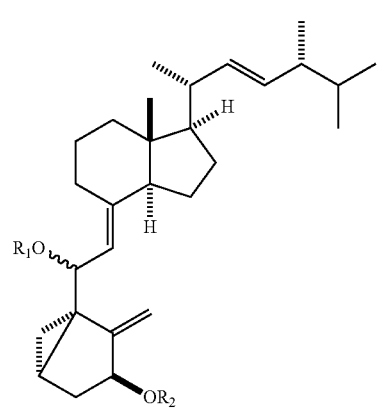

IM-A4 wherein $R_1$ and $R_2$ are as defined above,
to ozonolysis, in an inert solvent and, optionally in the presence of a base,
and wherein upon completion the ozonolysis reaction mixture is quenched with dimethyl sulfide or triphenylphosphine used as reducing agent to obtain a compound of the formula

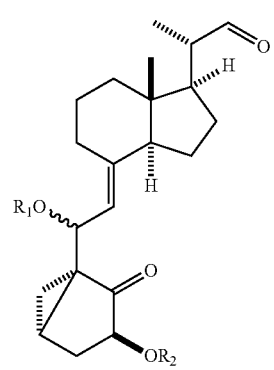

IM-A5 wherein $R_1$ and $R_2$ are defined as above;

(b) reacting a compound of the formula IM-A5 with sodium borohydride used as reducing agent, in ethanol as solvent, to obtain a compound of the formula

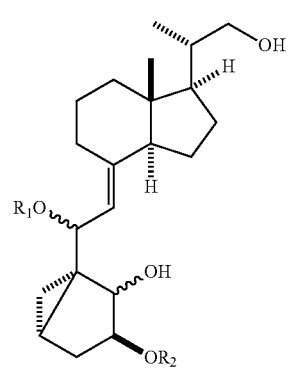

IM-B6 wherein $R_1$ and $R_2$ are defined as above;

(c) protecting the primary hydroxyl group in a compound of the formula IM-B6 with a hydroxyl protecting agent, optionally in an inert solvent, and optionally in the presence of a base to obtain a compound of the formula

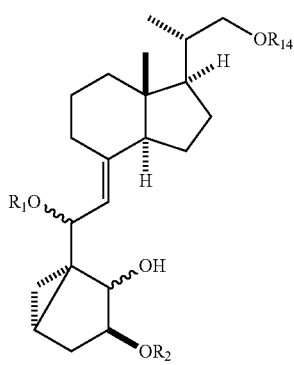

IM-B7 wherein $R_1$ and $R_2$ are defined as above and $R_{14}$ represents a hydroxyl protecting group;

(d) reacting the secondary hydroxyl group in a compound of the formula IM-B7 in the presence of a tertiary aromatic amine with a sulfonylating agent of the formula $(R_{13}SO_2)_2O$, wherein $R_{13}$ represents $C_1$-$C_4$ alkyl, unsubstituted aryl or aryl substituted by $C_1$-$C_2$ alkyl or halogen, optionally in the presence of a solvent, to obtain a compound of the formula

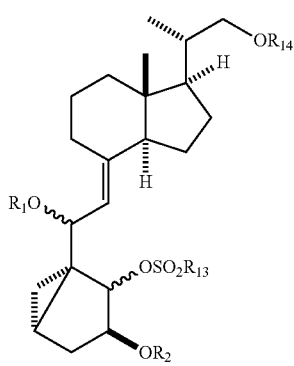

IM-B8 wherein $R_1$, $R_2$, $R_{13}$ and $R_{14}$ are defined as above;

(e) reacting a compound of the formula IM-B8 with lithium aluminium hydride as reducing agent, in an ether as solvent, in order to reduce the sulfonic ester group and reacting the primary hydroxyl group with a deprotecting agent, wherein the primary hydroxyl group is deprotected if present after the reduction to obtain a compound of the formula

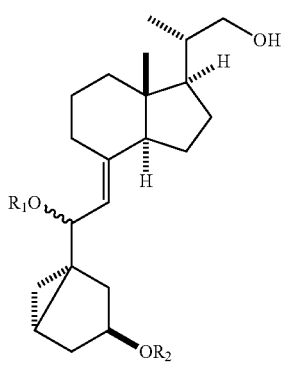

IM-B9 wherein $R_1$ and $R_2$ are defined as above;

(f) reacting a compound of the formula IM-B9 with an oxidizing agent, optionally in a solvent, and optionally in the presence of a base, to obtain a compound of the formula

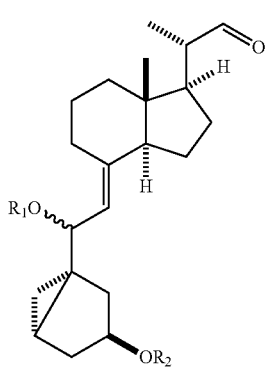

IM-C10 wherein $R_1$ and $R_2$ are defined as above, and wherein the oxidizing agent is NCS/DMS, Dess-Martin periodinane or DMSO/oxalylchloride;

(g) reacting a compound of the formula IM-C10 with a compound of the formula

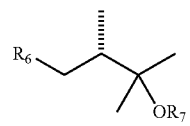

IM-II wherein $R_6$ represents $Ph_3P^+$ or $R_9SO_2$, wherein $R_9$ represents benzothiazol-2-yl, pyrid-2-yl, 1-phenyl-1H-tetrazol-5-yl, 1-tert.-butyl-1H-tetrazol-5-yl or 3,5-bistrifluoromethylphenyl with the proviso that if $R_6$ is $Ph_3P^+$ that $R_7$ is hydrogen and $R_7$ represents hydrogen or $R_8$ and wherein $R_8$ represents a hydroxyl protecting group and wherein the compound of the formula IM-II is deprotonated with a base, optionally in a solvent, prior to reaction with a compound of the formula IM-C10 to obtain a compound of the formula

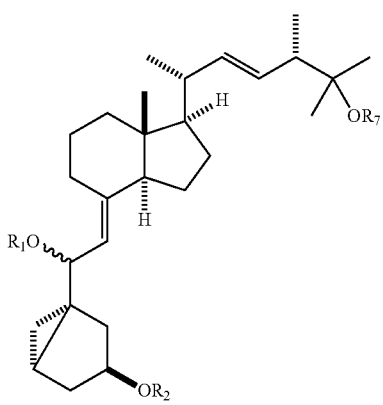

IM-A9 wherein $R_1$, $R_2$ and $R_7$ are defined as above;
(h) optionally to step (g), reacting a compound of the formula IM-C10 as defined in step (f) with a compound of the formula

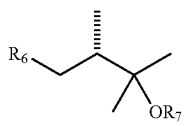

IM-II wherein $R_6$ represents $PhSO_2$ and
$R_7$ represents a hydroxyl protecting group and
wherein the compound of the formula IM-II is deprotonated with a base, optionally in a solvent, prior to reaction with a compound of the formula IM-C10
to obtain a compound of the formula

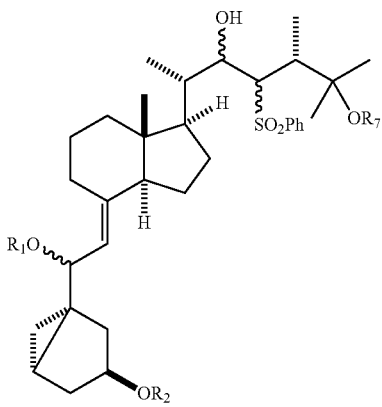

IM-C11 wherein $R_1$, $R_2$ and $R_7$ are defined as above and
wherein a compound of the formula IM-C11 is then subjected to a reductive desulfonylation, optionally after acylation of the C(22) hydroxy group, to obtain a compound of the formula IM-A9 wherein $R_1$, $R_2$ and $R_7$ are defined as above;
(i) subjecting a compound of the formula IM-A9 to solvolysis with a $C_1$-$C_4$ carboxylic acid or a mixture consisting of DMSO and a $C_1$-$C_4$ carboxylic acid to obtain a mixture of the compounds of the formulae IM-A10 (I/II)

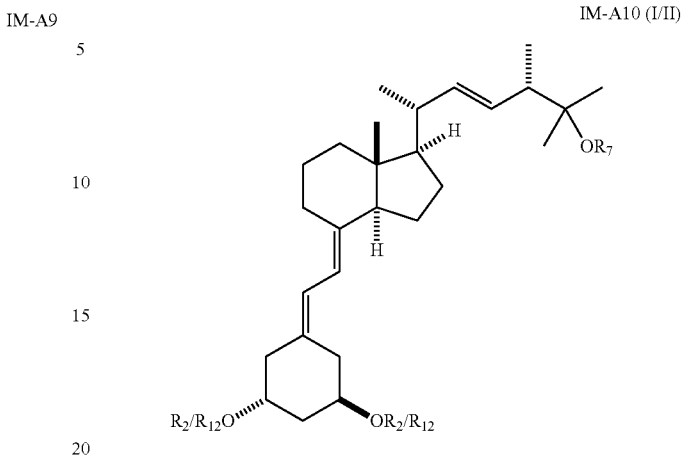

IM-A10 (I/II)

wherein $R_1$, $R_2$ and $R_7$ are defined as above and $R_{12}$ represents hydrogen or a $C_1$-$C_4$ acyl group; and
(j) reacting the mixture of the compounds of the formulae IM-A10 (I/II) with a deprotecting agent, optionally in a solvent, to obtain paricalcitol.

2. A process for preparing 19-nor-1α,3β,25-trihydroxy-9,10-secoergosta-5(Z), 7(Z), 22(E)-triene (paricalcitol) of the formula

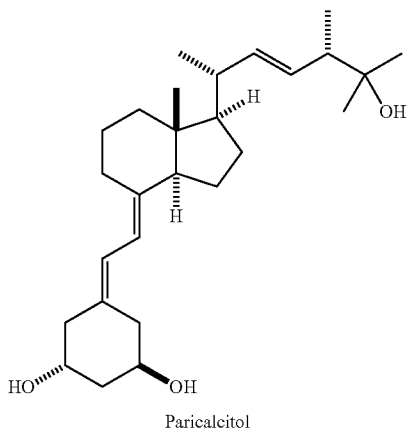 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Paricalcitol wherein vitamin D2 is used as starting material and wherein a compound of the formula

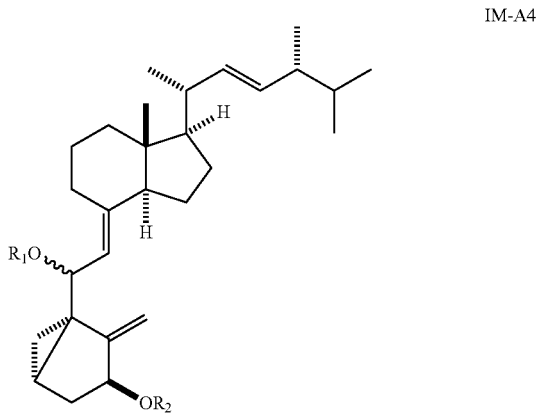

IM-A4 wherein Group R1 is methyl and R2 is tert.-butyldimethylsilyl group (TBS),
is used as an intermediate,
the process comprising synthesizing IM-A4 from vitamin D2 and further comprising the steps of:
(a) subjecting a compound of the formula

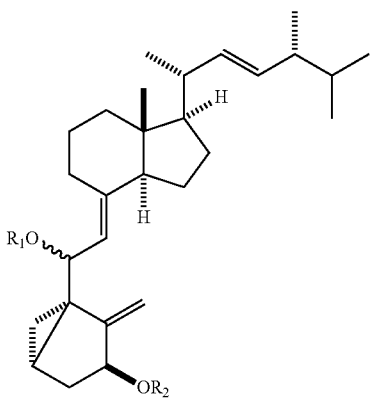

IM-A4 wherein
R$_1$ and R$_2$ are defined as in claim 1
to ozonolysis, in an inert solvent and, optionally in the presence of a base,
(b) treating the ozonolysis reaction mixture of step (a) with sodium borohydride used as reducing agent to obtain a compound of the formula

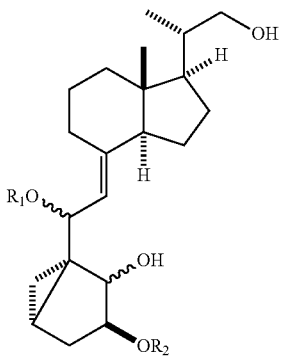

IM-B6 wherein R$_1$ and R$_2$ are defined as above;
(c) protecting the primary hydroxyl group in a compound of the formula IM-B6 with a hydroxyl protecting agent, optionally in an inert solvent, and optionally in the presence of a base, to obtain a compound of the formula

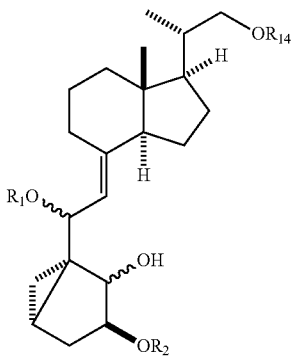

IM-B7 wherein R$_1$ and R$_2$ are defined as above and
R$_{14}$ represents a hydroxyl protecting group;
(d) reacting the secondary hydroxyl group in a compound of the formula IM-B7 in the presence of a tertiary aromatic amine with a sulfonylating agent of the formula (R$_{13}$SO$_2$)$_2$O, wherein R$_{13}$ represents C$_1$-C$_4$ alkyl, unsubstituted aryl or aryl substituted by C$_1$-C$_2$ alkyl or halogen, optionally in the presence of a solvent, to obtain a compound of the formula

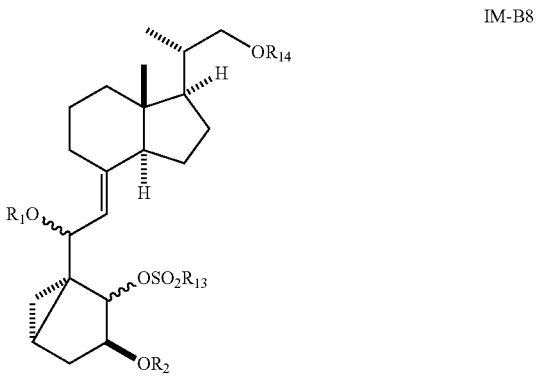

IM-B8 wherein R$_1$, R$_2$, R$_{13}$ and R$_{14}$ are defined as above;
(e) reacting a compound of the formula IM-B8 with lithium aluminium hydride as reducing agent, in an ether as solvent, in order to reduce the sulfonic ester group and reacting the primary hydroxyl group with a deprotecting agent, wherein the primary hydroxyl group is deprotected if present after the reduction to obtain a compound of the formula

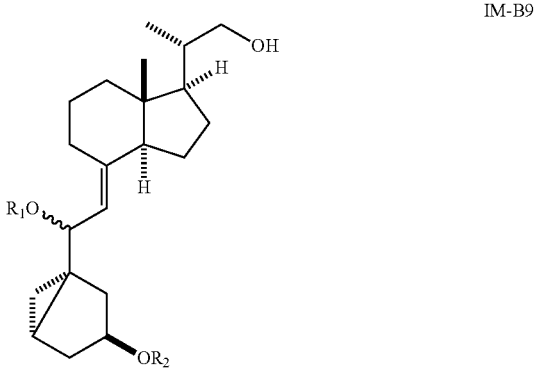

IM-B9 wherein R$_1$ and R$_2$ are defined as above;
(f) reacting a compound of the formula IM-B9 with an oxidizing agent, optionally in a solvent, and optionally in the presence of a base, to obtain a compound of the formula

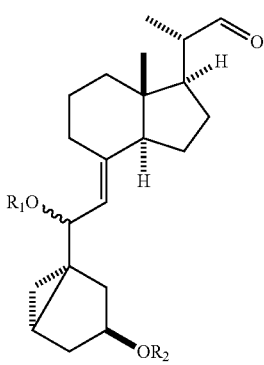

IM-C10 wherein $R_1$ and $R_2$ are defined as above, and wherein the oxidizing agent is NCS/DMS, Dess-Martin periodinane or DMSO/oxalylchloride;

(g) reacting a compound of the formula IM-C10 with a compound of the formula

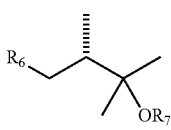

IM-II wherein $R_6$ represents $Ph_3P^+$ or $R_9SO_2$, wherein $R_9$ represents benzothiazol-2-yl, pyrid-2-yl, 1-phenyl-1H-tetrazol-5-yl, 1-tert.-butyl-1H-tetrazol-5-yl or 3,5-bistrifluoromethylphenyl with the proviso that if $R_6$ is $Ph_3P^+$ that $R_7$ is hydrogen and $R_7$ represents hydrogen or $R_8$ and wherein $R_8$ represents a hydroxyl protecting group and wherein the compound of the formula IM-II is deprotonated with a base, optionally in a solvent, prior to reaction with a compound of the formula IM-C10 to obtain a compound of the formula

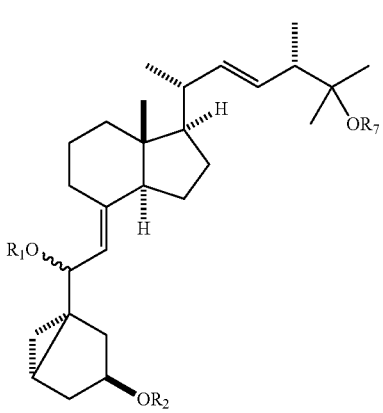

IM-A9 wherein $R_1$, $R_2$ and $R_7$ are defined as above;

(h) optionally to step (g), reacting a compound of the formula IM-C10 as defined in step (f)

with a compound of the formula

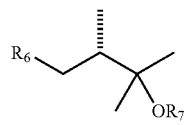

IM-II wherein $R_6$ represents $PhSO_2$ and $R_7$ represents a hydroxyl protecting group and wherein the compound of the formula IM-II is deprotonated with a base, optionally in a solvent, prior to reaction with a compound of the formula IM-C10 to obtain a compound of the formula

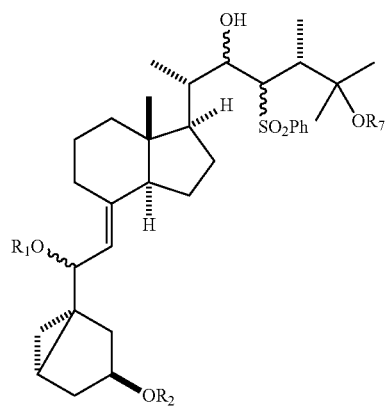

IM-C11 wherein $R_1$, $R_2$ and $R_7$ are defined as above and wherein a compound of the formula IM-C11 is then subjected to a reductive desulfonylation, optionally after acylation of the C(22) hydroxy group, to obtain a compound of the formula IM-A9 wherein $R_1$, $R_2$ and $R_7$ are defined as above;

(i) subjecting a compound of the formula IM-A9 to solvolysis with a $C_1$-$C_4$ carboxylic acid or a mixture consisting of DMSO and a $C_1$-$C_4$ carboxylic acid to obtain a mixture of the compounds of the formulae IM-A10 (I/II)

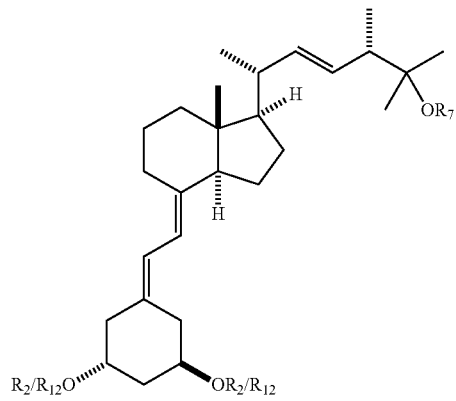

IM-A10 (I/II)

wherein $R_1$, $R_2$ and $R_7$ are defined as above and $R_{12}$ represents hydrogen or a $C_1$-$C_4$ acyl group; and (j) reacting the mixture of the compounds of the formulae IM-A10 (I/II) with a deprotecting agent, optionally in a solvent, to obtain paricalcitol.

3. The process according to claim 1, wherein the compound of the formula IM-A4 is the compound of the formula IM-A4e IM-A4e

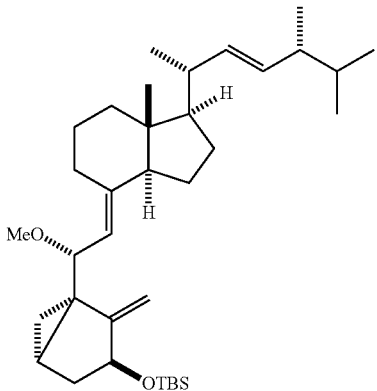

wherein Group R1 is methyl and R2 is tert.-butyldimethylsilyl group (TBS) of the formula IM-A4.

4. The process according to claim 1, wherein $R_1$ is a methyl group and $R_2$ is a silyl group, specifically wherein $R_2$ is a tert.-butyldimethylsilyl group (TBS) group.

5. The process according to claim 4, wherein the compound of the formula IM-A4 is obtained by reacting a compound of the formula

IM-A3

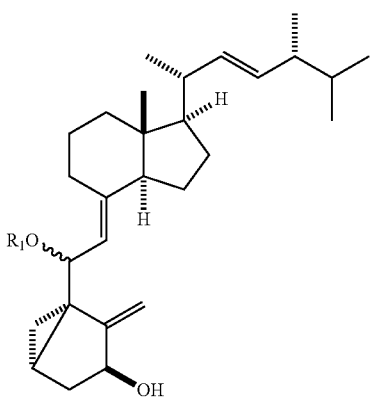

wherein $R_1$ is a $C_1$-$C_4$ alkyl group (specifically R1 is a methyl group)
with a silylating agent (specifically tert.-butyldimethylsilyl chloride (TBSCl), optionally in a solvent.

6. The process according to claim 1, wherein in step (a) the compound of the formula IM-A4e IM-A4e

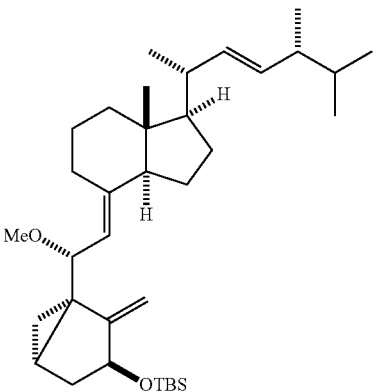

is subjected to ozonolysis to obtain compound of the formula IM-A5e

IM-A5e

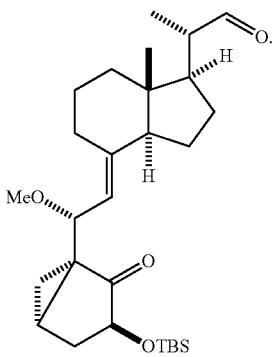

7. The process according to claim 1, wherein in step (a) the inert solvent is methylene chloride, a $C_1$-$C_4$ alcohol or a mixture thereof.

8. The process according to claim 1, wherein in step (a) pyridine is used as the base.

9. The process according to claim 1, wherein in step (b) the compound of the formula IM-A5e is reacted with sodium borohydride to obtain a compound of the formula IM-B6a IM-B6a

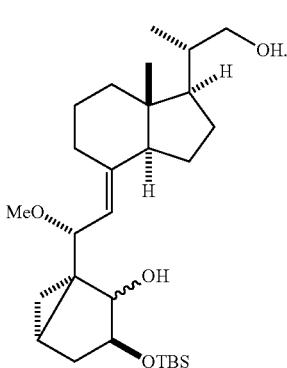

10. The process according to claim 1, wherein in step (c) the primary hydroxyl group is protected by an acyl group.

11. The process according to claim 10, wherein the primary hydroxyl group is protected by an acetyl group or a benzoyl group.

12. The process according to claim 11, wherein acetyl chloride or benzoyl chloride are used as hydroxyl protecting agent and wherein the acylation is carried out in methylene chloride as solvent at a temperature range from −5° C. to room temperature and in presence of pyridine as base.

13. The process according to claim 1, wherein in step (d) methane sulfonic acid anhydride or p-toluenesulfonic acid anhydride are reacted with a compound of the formula IM-B7 for the conversion of the secondary hydroxyl group to the corresponding sulfonic acid ester.

14. The process according to claim 13, wherein methane sulfonic acid anhydride is used.

15. The process according to claim 1, wherein in step (d) the solvent is methylene chloride or THF.

16. The process according to claim 1, wherein in step (d) the tertiary aromatic amine is pyridine.

17. The process according to claim 1, wherein in step (e) the solvent is diethyl ether.

18. The process according to claim 1, wherein in step (e) the primary hydroxyl group in a compound of the formula IM-B8 is protected by an acyl group which is simultaneously cleaved during the reduction of the sulfonic ester group.

19. The process according to claim 18, wherein the acyl group is acetyl or benzoyl.

20. The process according to claim 1, wherein in step (f) DMSO and oxalylchloride are used as oxidizing agents.

21. The process according to claim 20, wherein a compound of the formula IM-B9 is added to a mixture of DMSO and oxalylchloride in a solvent (preferentially methylene chloride) and in the presence of a tertiary aromatic amine as a base at a temperature range from −80° C. to −50° C., followed by addition of a tertiary alkyl amine as a base.

22. The process according to claim 21, wherein the tertiary alkyl amine is triethylamine and wherein the tertiary aromatic amine is pyridine.

23. The process according to claim 1, wherein in step (g) a compound of the formula IM-C10 is reacted with a compound of the formula

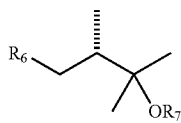

IM-II wherein $R_6$ represents $Ph_3P^+$ and $R_7$ represents hydrogen (compound IM-WR5).

24. The process according to claim 23, wherein the compound of the formula IM-WR5 is deprotonated first by using MeLi in diethyl ether as solvent at a temperature range from 0° C. to room temperature before the reaction with a compound of the formula IM-C10 is carried out.

25. The process according to claim 24, wherein the deprotonated IM-WR5 is reacted with a compound of the formula IM-C10 at a temperature from −25° C. to −15° C.

26. The process according to claim 24, wherein additionally a $C_2$-$C_4$-carboxylic acid $C_1$-$C_2$-ester is added to the deprotonated IM-WR5 mixture prior to its reaction with IM-C10.

27. The process according to claim 26, wherein ethyl acetate is added.

28. The process according to claim 1, wherein in step (i) the solvolysis is carried out with acetic acid and wherein the amount of acetic acid employed for the solvolysis ranges from about 5 mL to about 20 mL per gram IM-A9.

29. The process according to claim 1, wherein in step (j) the cleavage of $R_2$, $R_7$=$R_8$ and $R_{12}$ is carried out in a one pot process.

30. The process according to claim 1, wherein in step (j) in the mixture of the compounds of the formulae IM-A10 (I/II) $R_2$ represents a silyl group, $R_{12}$ represents an acyl group and $R_7$ represents hydrogen or a silyl group and wherein the deprotection is carried out by desilylation and by saponification, optionally as one pot process.

31. The process according to claim 30, wherein $R_2$ represents a tert.-butyldimethylsilyl group (TBS) group, $R_7$ represents hydrogen or triethylsilyl (TES) group and $R_{12}$ represents an acetyl group.

32. The process according to claim 31, wherein the TBS group and TES group is cleaved by treatment with TBAF in THF at room temperature.

33. The process according to claim 31, wherein the acetyl group is cleaved with sodium hydroxide carried out in methanol, ethanol or a mixture consisting of methanol or ethanol and THF as solvent.

* * * * *